US011464846B2

(12) United States Patent
Li et al.

(10) Patent No.: US 11,464,846 B2
(45) Date of Patent: Oct. 11, 2022

(54) MUTANT OF L1 PROTEIN OF HUMAN PAPILLOMAVIRUS TYPE 66

(71) Applicants: Xiamen University, Fujian (CN); Xiamen Innovax Biotech Co., Ltd., Fujian (CN)

(72) Inventors: Shaowei Li, Fujian (CN); Xinlin Liu, Fujian (CN); Yurou Yang, Fujian (CN); Jie Chen, Fujian (CN); Daning Wang, Fujian (CN); Ningshao Xia, Fujian (CN)

(73) Assignees: XIAMEN UNIVERSITY, Fujian (CN); XIAMEN INNOVAX BIOTECH, CO., LTD., Fujian (CN)

( * ) Notice: Subject to any disclaimer, the term of this patent is extended or adjusted under 35 U.S.C. 154(b) by 0 days.

(21) Appl. No.: 15/734,750

(22) PCT Filed: Jun. 4, 2019

(86) PCT No.: PCT/CN2019/089940
§ 371 (c)(1),
(2) Date: Dec. 3, 2020

(87) PCT Pub. No.: WO2019/233400
PCT Pub. Date: Dec. 12, 2019

(65) Prior Publication Data
US 2021/0236618 A1    Aug. 5, 2021

(30) Foreign Application Priority Data
Jun. 4, 2018    (CN) .......................... 201810563504.2

(51) Int. Cl.
| | |
|---|---|
| *A61K 39/12* | (2006.01) |
| *C07K 14/025* | (2006.01) |
| *C12N 7/00* | (2006.01) |
| *A61K 39/00* | (2006.01) |

(52) U.S. Cl.
CPC ............ *A61K 39/12* (2013.01); *C07K 14/025* (2013.01); *C12N 7/00* (2013.01); *A61K 2039/5258* (2013.01); *C12N 2710/20034* (2013.01)

(58) Field of Classification Search
None
See application file for complete search history.

(56) References Cited

U.S. PATENT DOCUMENTS 6,551,597 B1 * 4/2003 Harrison ................. A61P 31/12
435/69.3

FOREIGN PATENT DOCUMENTS

CN         101914139 B     11/2021

OTHER PUBLICATIONS

International Search Report, issued in PCT/CN2019/089940, dated Aug. 22, 2019.
Varsani et al., "Chimeric Human Papillomavirus Type 16 (HPV-16) L1 Particles Presenting the Common Neutralizing Epitope for the L2 Minor Capsid Protein of HPV-6 and HPV-16," Journal of Virology, vol. 77, No. 15, (2003), pp. 8386-8393.
Extended European Search Report issued in European Application No. 19815012.0, dated Mar. 4, 2022.
Herd et al., "Recombinant Kunjin Virus Replicon Vaccines Induce Protective T-cell Immunity Against Human Papillomavirus 16 E7-Expressing Tumour," Virology, Elsevier, Amsterdam, NL, vol. 319, No. 2 (Feb. 20, 2004), pp. 237-348.
Bogers et al., "Potent Immune Responses in Rhesus Macaques Induced by Nonviral Delivery of a Self-amplifying RNA Vaccine Expressing HIV Type 1 Envelope With a Cationic Nanoemulsion," The Journal of Infectious Diseases, Infectious Diseases Society of America, US, vol. 211, No. 6, (Mar. 15, 2015), pp. 947-955.

* cited by examiner

*Primary Examiner* — Nianxiang Zou
(74) *Attorney, Agent, or Firm* — Barnes & Thornburg LLP

(57) ABSTRACT

The invention relates to a mutated HPV66 L1 protein (or a variant thereof), a sequence encoding the same, a method for preparing the same, and a virus-like particle comprising the same, wherein the protein (or a variant thereof) and the virus-like particle can induce the generation of neutralizing antibodies against at least two HPV types (e.g. HPV66 and HPV56, or HPV66, HPV56 and HPV53), and therefore can be used to prevent infection by said at least two HPV types, and a disease caused by said infection, such as cervical cancer and condyloma acuminatum. The invention further relates to the use of the protein and the virus-like particle in the manufacture of a pharmaceutical composition or a vaccine for preventing infection by said at least two HPV types, and a disease caused by said infection, such as cervical cancer and condyloma acuminatum.

20 Claims, 10 Drawing Sheets

Specification includes a Sequence Listing.

```
                         SEQUENCE LISTING

<160> NUMBER OF SEQ ID NOS: 65

<210> SEQ ID NO 1
<211> LENGTH: 502
<212> TYPE: PRT
<213> ORGANISM: Human papillomavirus type 66

<400> SEQUENCE: 1

Met Ala Met Trp Arg Pro Ser Asp Asn Lys Val Tyr Leu Pro Pro Thr
1               5                   10                  15

Pro Val Ser Lys Val Val Ala Thr Asp Thr Tyr Val Lys Arg Thr Ser
            20                  25                  30

Ile Phe Tyr His Ala Gly Ser Ser Arg Leu Leu Ala Val Gly His Pro
        35                  40                  45

Tyr Tyr Ser Val Ser Lys Ser Gly Thr Lys Thr Asn Ile Pro Lys Val
    50                  55                  60

Ser Ala Tyr Gln Tyr Arg Val Phe Arg Val Arg Leu Pro Asp Pro Asn
65                  70                  75                  80

Lys Phe Gly Leu Pro Asp Pro Ser Phe Tyr Asn Pro Asp Gln Glu Arg
                85                  90                  95

Leu Val Trp Ala Cys Val Gly Leu Glu Val Gly Arg Gly Gln Pro Leu
            100                 105                 110

Gly Ala Gly Leu Ser Gly His Pro Leu Phe Asn Arg Leu Asp Asp Thr
        115                 120                 125

Glu Val Ser Asn Leu Ala Gly Asn Asn Val Ile Glu Asp Ser Arg Asp
    130                 135                 140

Asn Ile Ser Val Asp Cys Lys Gln Thr Gln Leu Cys Ile Val Gly Cys
145                 150                 155                 160

Ala Pro Ala Leu Gly Glu His Trp Thr Lys Gly Ala Val Cys Lys Ser
                165                 170                 175

Thr Pro Gly Asn Thr Gly Asp Cys Pro Pro Leu Ala Leu Val Asn Thr
            180                 185                 190

Pro Ile Glu Asp Gly Asp Met Val Asp Thr Gly Phe Gly Ala Met Asp
        195                 200                 205

Phe Lys Leu Leu Gln Glu Ser Lys Ala Glu Val Pro Leu Asp Ile Val
    210                 215                 220
```

Gln Ser Thr Cys Lys Tyr Pro Asp Tyr Leu Lys Met Ser Ala Asp Ala
225                 230                 235                 240

Tyr Gly Asp Ser Met Trp Phe Tyr Leu Arg Arg Glu Gln Leu Phe Ala
            245                 250                 255

Arg His Tyr Phe Asn Arg Ala Gly Asn Val Gly Glu Ala Ile Pro Thr
                260                 265                 270

Asp Leu Tyr Trp Lys Gly Gly Asn Gly Arg Asp Pro Pro Ser Ser
            275                 280                 285

Val Tyr Val Ala Thr Pro Ser Gly Ser Met Ile Thr Ser Glu Ala Gln
    290                 295                 300

Leu Phe Asn Lys Pro Tyr Trp Leu Gln Arg Ala Gln Gly His Asn Asn
305                 310                 315                 320

Gly Ile Cys Trp Gly Asn Gln Val Phe Val Thr Val Asp Thr Thr
                325                 330                 335

Arg Ser Thr Asn Met Thr Ile Asn Ala Ala Lys Ser Thr Leu Thr Lys
                340                 345                 350

Tyr Asp Ala Arg Glu Ile Asn Gln Tyr Leu Arg His Val Glu Glu Tyr
            355                 360                 365

Glu Leu Gln Phe Val Phe Gln Leu Cys Lys Ile Thr Leu Thr Ala Glu
370                 375                 380

Val Met Ala Tyr Leu His Asn Met Asn Asn Thr Leu Leu Asp Asp Trp
385                 390                 395                 400

Asn Ile Gly Leu Ser Pro Pro Val Ala Thr Ser Leu Glu Asp Lys Tyr
                405                 410                 415

Arg Tyr Ile Lys Ser Thr Ala Ile Thr Cys Gln Arg Glu Gln Pro Pro
            420                 425                 430

Ala Glu Lys Gln Asp Pro Leu Ala Lys Tyr Lys Phe Trp Glu Val Asn
            435                 440                 445

Leu Gln Asp Ser Phe Ser Ala Asp Leu Asp Gln Phe Pro Leu Gly Arg
    450                 455                 460

Lys Phe Leu Met Gln Leu Gly Pro Arg Pro Arg Pro Lys Ala Ser
465                 470                 475                 480

Val Ser Ala Ser Lys Arg Arg Ala Ala Pro Thr Ser Ser Ser Ser
                485                 490                 495

Pro Ala Lys Arg Lys Lys
            500

<210> SEQ ID NO 2
<211> LENGTH: 499
<212> TYPE: PRT
<213> ORGANISM: Human papillomavirus type 56

<400> SEQUENCE: 2

Met Ala Thr Trp Arg Pro Ser Glu Asn Lys Val Tyr Leu Pro Pro Thr
1               5                   10                  15

Pro Val Ser Lys Val Val Ala Thr Asp Ser Tyr Val Lys Arg Thr Ser
                20                  25                  30

Ile Phe Tyr His Ala Gly Ser Ser Arg Leu Leu Ala Val Gly His Pro
            35                  40                  45

Tyr Tyr Ser Val Thr Lys Asp Asn Thr Lys Thr Asn Ile Pro Lys Val
        50                  55                  60

Ser Ala Tyr Gln Tyr Arg Val Phe Arg Val Arg Leu Pro Asp Pro Asn
65                  70                  75                  80

Lys Phe Gly Leu Pro Asp Thr Asn Ile Tyr Asn Pro Asp Gln Glu Arg
                85                  90                  95

```
Leu Val Trp Ala Cys Val Gly Leu Glu Val Gly Arg Gly Gln Pro Leu
            100                 105                 110

Gly Ala Gly Leu Ser Gly His Pro Leu Phe Asn Arg Leu Asp Asp Thr
            115                 120                 125

Glu Ser Ser Asn Leu Ala Asn Asn Val Ile Glu Asp Ser Arg Asp
        130                 135                 140

Asn Ile Ser Val Asp Gly Lys Gln Thr Gln Leu Cys Ile Val Gly Cys
145                 150                 155                 160

Thr Pro Ala Met Gly Glu His Trp Thr Lys Gly Ala Val Cys Lys Ser
                165                 170                 175

Thr Gln Val Thr Thr Gly Asp Cys Pro Pro Leu Ala Leu Ile Asn Thr
            180                 185                 190

Pro Ile Glu Asp Gly Asp Met Ile Asp Thr Gly Phe Gly Ala Met Asp
            195                 200                 205

Phe Lys Val Leu Gln Glu Ser Lys Ala Glu Val Pro Leu Asp Ile Val
        210                 215                 220

Gln Ser Thr Cys Lys Tyr Pro Asp Tyr Leu Lys Met Ser Ala Asp Ala
225                 230                 235                 240

Tyr Gly Asp Ser Met Trp Phe Tyr Leu Arg Arg Glu Gln Leu Phe Ala
                245                 250                 255

Arg His Tyr Phe Asn Arg Ala Gly Lys Val Gly Glu Thr Ile Pro Ala
                260                 265                 270

Glu Leu Tyr Leu Lys Gly Ser Asn Gly Arg Glu Pro Pro Ser Ser
        275                 280                 285

Val Tyr Val Ala Thr Pro Ser Gly Ser Met Ile Thr Ser Glu Ala Gln
        290                 295                 300

Leu Phe Asn Lys Pro Tyr Trp Leu Gln Arg Ala Gln Gly His Asn Asn
305                 310                 315                 320

Gly Ile Cys Trp Gly Asn Gln Leu Phe Val Thr Val Val Asp Thr Thr
                325                 330                 335

Arg Ser Thr Asn Met Thr Ile Ser Thr Ala Thr Glu Gln Leu Ser Lys
                340                 345                 350

Tyr Asp Ala Arg Lys Ile Asn Gln Tyr Leu Arg His Val Glu Glu Tyr
            355                 360                 365

Glu Leu Gln Phe Val Phe Gln Leu Cys Lys Ile Thr Leu Ser Ala Glu
        370                 375                 380

Val Met Ala Tyr Leu His Asn Met Asn Ala Asn Leu Leu Glu Asp Trp
385                 390                 395                 400

Asn Ile Gly Leu Ser Pro Pro Val Ala Thr Ser Leu Glu Asp Lys Tyr
                405                 410                 415

Arg Tyr Val Arg Ser Thr Ala Ile Thr Cys Gln Arg Glu Gln Pro Pro
            420                 425                 430

Thr Glu Lys Gln Asp Pro Leu Ala Lys Tyr Lys Phe Trp Asp Val Asn
        435                 440                 445

Leu Gln Asp Ser Phe Ser Thr Asp Leu Asp Gln Phe Pro Leu Gly Arg
            450                 455                 460

Lys Phe Leu Met Gln Leu Gly Thr Arg Ser Lys Pro Ala Val Ala Thr
465                 470                 475                 480

Ser Lys Lys Arg Ser Ala Pro Thr Ser Thr Ser Thr Pro Ala Lys Arg
                485                 490                 495

Lys Arg Arg
```

```
<210> SEQ ID NO 3
<211> LENGTH: 499
<212> TYPE: PRT
<213> ORGANISM: Human papillomavirus type 53

<400> SEQUENCE: 3
```

| | | | | | | | | | | | | | | |
|---|---|---|---|---|---|---|---|---|---|---|---|---|---|---|
| Met | Ala | Val | Trp | Arg | Pro | Ser | Asp | Ser | Lys | Val | Tyr | Leu | Pro | Thr |
| 1 | | | | 5 | | | | | 10 | | | | | 15 |
| Pro | Val | Ser | Lys | Val | Ile | Thr | Thr | Asp | Ala | Tyr | Val | Lys | Arg | Thr |
| | | | 20 | | | | | 25 | | | | | 30 | |
| Ile | Phe | Tyr | His | Ala | Gly | Ser | Ser | Arg | Leu | Leu | Thr | Val | Gly | His | Pro |

Met Ala Val Trp Arg Pro Ser Asp Ser Lys Val Tyr Leu Pro Thr
1               5                   10                  15

Pro Val Ser Lys Val Ile Thr Thr Asp Ala Tyr Val Lys Arg Thr
            20              25                  30

Ile Phe Tyr His Ala Gly Ser Ser Arg Leu Leu Thr Val Gly His Pro
            35              40                  45

Tyr Tyr Pro Ile Ser Lys Ser Gly Lys Ala Asp Ile Pro Lys Val Ser
50                  55                  60

Ala Phe Gln Tyr Arg Val Phe Arg Val Arg Leu Pro Asp Pro Asn Lys
65              70                  75                  80

Phe Gly Leu Pro Asp Thr Asn Ile Phe Asn Pro Asp Gln Glu Arg Leu
            85                  90                  95

Val Trp Ala Cys Val Gly Leu Glu Ile Gly Arg Gly Gln Pro Leu Gly
            100                 105                 110

Val Gly Val Ser Gly His Pro Leu Phe Asn Arg Leu Asp Asp Thr Glu
            115                 120                 125

Ser Ser Ser Ile Ala Ile Gln Asp Thr Ala Pro Asp Ser Arg Asp Asn
130                 135                 140

Val Ser Val Asp Pro Lys Gln Thr Gln Leu Cys Ile Ile Gly Cys Ala
145                 150                 155                 160

Pro Ala Ile Gly Glu His Trp Thr Lys Gly Thr Ala Cys Arg Ser Thr
                165                 170                 175

Pro Thr Thr Ala Gly Asp Cys Pro Pro Leu Glu Leu Ile Asn Ser Pro
            180                 185                 190

Ile Glu Asp Gly Asp Met Val Asp Thr Gly Phe Gly Ala Leu Asn Phe
            195                 200                 205

Lys Ala Leu Gln Glu Ser Lys Ser Asp Val Pro Leu Asp Ile Val Gln
210                 215                 220

Ser Thr Cys Lys Tyr Pro Asp Tyr Leu Lys Met Ser Ala Asp Ala Tyr
225                 230                 235                 240

Gly Asp Ser Met Trp Phe Tyr Leu Arg Arg Glu Gln Leu Phe Thr Arg
                245                 250                 255

His Phe Phe Asn Arg Ala Gly Val Ile Gly Glu Glu Ile Pro Asn Asp
                260                 265                 270

Leu Tyr Ile Lys Gly Ser Asn Gly Arg Asp Pro Pro Ser Ser Val
            275                 280                 285

Tyr Val Ala Thr Pro Ser Gly Ser Met Ile Thr Ser Glu Ala Gln Leu
            290                 295                 300

Phe Asn Lys Pro Tyr Trp Leu Gln Arg Ala Gln Gly His Asn Asn Gly
305                 310                 315                 320

Ile Cys Trp Asn Asn Gln Leu Phe Val Thr Val Asp Thr Thr Arg
            325                 330                 335

Asn Thr Asn Met Thr Leu Ser Ala Thr Thr Gln Ser Met Ser Thr Tyr
            340                 345                 350

Asn Ser Lys Gln Ile Lys Gln Tyr Val Arg His Ala Glu Glu Tyr Glu
            355                 360                 365

Leu Gln Phe Val Phe Gln Leu Cys Lys Ile Ser Leu Ser Ala Glu Val
            370                 375                 380

```
Met Ala Tyr Leu His Thr Met Asn Ser Thr Leu Glu Asp Trp Asn
385                 390                 395                 400

Ile Gly Leu Ser Pro Val Ala Thr Ser Leu Glu Asp Lys Tyr Arg
            405                 410                 415

Tyr Val Lys Ser Ala Ala Ile Thr Cys Gln Lys Asp Gln Pro Pro
        420                 425                 430

Glu Lys Gln Asp Pro Leu Ser Lys Tyr Lys Phe Trp Glu Val Asn Leu
    435                 440                 445

Gln Asn Ser Phe Ser Ala Asp Leu Asp Gln Phe Pro Leu Gly Arg Lys
    450                 455                 460

Phe Leu Met Gln Val Gly Val Arg Thr Lys Pro Pro Val Ser Ser Lys
465                 470                 475                 480

Lys Arg Ser Ala Ser Thr Thr Ser Thr Ser Ala Pro Ser Ser Lys Arg
                485                 490                 495

Lys Arg Lys

<210> SEQ ID NO 4
<211> LENGTH: 498
<212> TYPE: PRT
<213> ORGANISM: Artificial Sequence
<220> FEATURE:
<223> OTHER INFORMATION: Synthesized Sequence

<400> SEQUENCE: 4

Met Pro Ser Asp Asn Lys Val Tyr Leu Pro Thr Pro Val Ser Lys
1               5                  10                   15

Val Val Ala Thr Asp Thr Tyr Val Lys Arg Thr Ser Ile Phe Tyr His
            20                   25                   30

Ala Gly Ser Ser Arg Leu Leu Ala Val Gly His Pro Tyr Tyr Ser Val
        35                   40                   45

Thr Lys Asp Asn Thr Lys Thr Asn Ile Pro Lys Val Ser Ala Tyr Gln
    50                   55                   60

Tyr Arg Val Phe Arg Val Arg Leu Pro Asp Pro Asn Lys Phe Gly Leu
65                   70                   75                   80

Pro Asp Pro Ser Phe Tyr Asn Pro Asp Gln Glu Arg Leu Val Trp Ala
                85                   90                   95

Cys Val Gly Leu Glu Val Gly Arg Gly Gln Pro Leu Gly Ala Gly Leu
            100                  105                  110

Ser Gly His Pro Leu Phe Asn Arg Leu Asp Asp Thr Glu Val Ser Asn
        115                  120                  125

Leu Ala Gly Asn Asn Val Ile Glu Asp Ser Arg Asp Asn Ile Ser Val
    130                  135                  140

Asp Cys Lys Gln Thr Gln Leu Cys Ile Val Gly Cys Ala Pro Ala Leu
145                  150                  155                  160

Gly Glu His Trp Thr Lys Gly Ala Val Cys Lys Ser Thr Pro Gly Asn
                165                  170                  175

Thr Gly Asp Cys Pro Pro Leu Ala Leu Val Asn Thr Pro Ile Glu Asp
            180                  185                  190

Gly Asp Met Val Asp Thr Gly Phe Gly Ala Met Asp Phe Lys Leu Leu
        195                  200                  205

Gln Glu Ser Lys Ala Glu Val Pro Leu Asp Ile Val Gln Ser Thr Cys
    210                  215                  220

Lys Tyr Pro Asp Tyr Leu Lys Met Ser Ala Asp Ala Tyr Gly Asp Ser
225                  230                  235                  240

Met Trp Phe Tyr Leu Arg Arg Glu Gln Leu Phe Ala Arg His Tyr Phe
```

```
                    245                 250                 255
Asn Arg Ala Gly Asn Val Gly Glu Ala Ile Pro Thr Asp Leu Tyr Trp
            260                 265                 270

Lys Gly Gly Asn Gly Arg Asp Pro Pro Ser Ser Val Tyr Val Ala
        275                 280                 285

Thr Pro Ser Gly Ser Met Ile Thr Ser Glu Ala Gln Leu Phe Asn Lys
    290                 295                 300

Pro Tyr Trp Leu Gln Arg Ala Gln Gly His Asn Asn Gly Ile Cys Trp
305                 310                 315                 320

Gly Asn Gln Val Phe Val Thr Val Asp Thr Thr Arg Ser Thr Asn
                325                 330                 335

Met Thr Ile Asn Ala Ala Lys Ser Thr Leu Thr Lys Tyr Asp Ala Arg
                340                 345                 350

Glu Ile Asn Gln Tyr Leu Arg His Val Glu Glu Tyr Glu Leu Gln Phe
            355                 360                 365

Val Phe Gln Leu Cys Lys Ile Thr Leu Thr Ala Glu Val Met Ala Tyr
        370                 375                 380

Leu His Asn Met Asn Asn Thr Leu Leu Asp Asp Trp Asn Ile Gly Leu
385                 390                 395                 400

Ser Pro Pro Val Ala Thr Ser Leu Glu Asp Lys Tyr Arg Tyr Ile Lys
                405                 410                 415

Ser Thr Ala Ile Thr Cys Gln Arg Glu Gln Pro Pro Ala Glu Lys Gln
                420                 425                 430

Asp Pro Leu Ala Lys Tyr Lys Phe Trp Glu Val Asn Leu Gln Asp Ser
            435                 440                 445

Phe Ser Ala Asp Leu Asp Gln Phe Pro Leu Gly Arg Lys Phe Leu Met
    450                 455                 460

Gln Leu Gly Pro Arg Pro Pro Arg Pro Lys Ala Ser Val Ser Ala Ser
465                 470                 475                 480

Lys Arg Arg Ala Ala Pro Thr Ser Ser Ser Ser Pro Ala Lys Arg
                485                 490                 495

Lys Lys

<210> SEQ ID NO 5
<211> LENGTH: 498
<212> TYPE: PRT
<213> ORGANISM: Artificial Sequence
<220> FEATURE:
<223> OTHER INFORMATION: Synthesized Sequence

<400> SEQUENCE: 5

Met Pro Ser Asp Asn Lys Val Tyr Leu Pro Pro Thr Pro Val Ser Lys
1               5                   10                  15

Val Val Ala Thr Asp Thr Tyr Val Lys Arg Thr Ser Ile Phe Tyr His
                20                  25                  30

Ala Gly Ser Ser Arg Leu Leu Ala Val Gly His Pro Tyr Tyr Ser Val
            35                  40                  45

Ser Lys Ser Gly Thr Lys Thr Asn Ile Pro Lys Val Ser Ala Tyr Gln
        50                  55                  60

Tyr Arg Val Phe Arg Val Arg Leu Pro Asp Pro Asn Lys Phe Gly Leu
65                  70                  75                  80

Pro Asp Pro Ser Phe Tyr Asn Pro Asp Gln Glu Arg Leu Val Trp Ala
                85                  90                  95

Cys Val Gly Leu Glu Val Gly Arg Gly Gln Pro Leu Gly Ala Gly Leu
            100                 105                 110
```

```
Ser Gly His Pro Leu Phe Asn Arg Leu Asp Asp Thr Glu Ser Ser Asn
        115                 120                 125

Leu Ala Asn Asn Val Ile Glu Asp Ser Arg Asp Asn Ile Ser Val
130                 135                 140

Asp Gly Lys Gln Thr Gln Leu Cys Ile Val Gly Cys Ala Pro Ala Leu
145                 150                 155                 160

Gly Glu His Trp Thr Lys Gly Ala Val Cys Lys Ser Thr Pro Gly Asn
                165                 170                 175

Thr Gly Asp Cys Pro Pro Leu Ala Leu Val Asn Thr Pro Ile Glu Asp
                180                 185                 190

Gly Asp Met Val Asp Thr Gly Phe Gly Ala Met Asp Phe Lys Leu Leu
                195                 200                 205

Gln Glu Ser Lys Ala Glu Val Pro Leu Asp Ile Val Gln Ser Thr Cys
        210                 215                 220

Lys Tyr Pro Asp Tyr Leu Lys Met Ser Ala Asp Ala Tyr Gly Asp Ser
225                 230                 235                 240

Met Trp Phe Tyr Leu Arg Arg Glu Gln Leu Phe Ala Arg His Tyr Phe
                245                 250                 255

Asn Arg Ala Gly Asn Val Gly Glu Ala Ile Pro Thr Asp Leu Tyr Trp
                260                 265                 270

Lys Gly Gly Asn Gly Arg Asp Pro Pro Ser Ser Val Tyr Val Ala
                275                 280                 285

Thr Pro Ser Gly Ser Met Ile Thr Ser Glu Ala Gln Leu Phe Asn Lys
        290                 295                 300

Pro Tyr Trp Leu Gln Arg Ala Gln Gly His Asn Gly Ile Cys Trp
305                 310                 315                 320

Gly Asn Gln Val Phe Val Thr Val Val Asp Thr Thr Arg Ser Thr Asn
                325                 330                 335

Met Thr Ile Asn Ala Ala Lys Ser Thr Leu Thr Lys Tyr Asp Ala Arg
                340                 345                 350

Glu Ile Asn Gln Tyr Leu Arg His Val Glu Glu Tyr Glu Leu Gln Phe
        355                 360                 365

Val Phe Gln Leu Cys Lys Ile Thr Leu Thr Ala Glu Val Met Ala Tyr
370                 375                 380

Leu His Asn Met Asn Asn Thr Leu Leu Asp Asp Trp Asn Ile Gly Leu
385                 390                 395                 400

Ser Pro Pro Val Ala Thr Ser Leu Glu Asp Lys Tyr Arg Tyr Ile Lys
                405                 410                 415

Ser Thr Ala Ile Thr Cys Gln Arg Glu Gln Pro Pro Ala Glu Lys Gln
                420                 425                 430

Asp Pro Leu Ala Lys Tyr Lys Phe Trp Glu Val Asn Leu Gln Asp Ser
        435                 440                 445

Phe Ser Ala Asp Leu Asp Gln Phe Pro Leu Gly Arg Lys Phe Leu Met
450                 455                 460

Gln Leu Gly Pro Arg Pro Arg Pro Lys Ala Ser Val Ser Ala Ser
465                 470                 475                 480

Lys Arg Arg Ala Ala Pro Thr Ser Ser Ser Ser Pro Ala Lys Arg
                485                 490                 495

Lys Lys

<210> SEQ ID NO 6
<211> LENGTH: 498
<212> TYPE: PRT
```

<213> ORGANISM: Artificial Sequence
<220> FEATURE:
<223> OTHER INFORMATION: Synthesized Sequence

<400> SEQUENCE: 6

```
Met Pro Ser Asp Asn Lys Val Tyr Leu Pro Thr Pro Val Ser Lys
1               5                   10                  15

Val Val Ala Thr Asp Thr Tyr Val Lys Arg Thr Ser Ile Phe Tyr His
            20                  25                  30

Ala Gly Ser Ser Arg Leu Leu Ala Val Gly His Pro Tyr Tyr Ser Val
        35                  40                  45

Ser Lys Ser Gly Thr Lys Thr Asn Ile Pro Lys Val Ser Ala Tyr Gln
    50                  55                  60

Tyr Arg Val Phe Arg Val Arg Leu Pro Asp Pro Asn Lys Phe Gly Leu
65              70                  75                  80

Pro Asp Pro Ser Phe Tyr Asn Pro Asp Gln Glu Arg Leu Val Trp Ala
                85                  90                  95

Cys Val Gly Leu Glu Val Gly Arg Gly Gln Pro Leu Gly Ala Gly Leu
            100                 105                 110

Ser Gly His Pro Leu Phe Asn Arg Leu Asp Asp Thr Glu Val Ser Asn
        115                 120                 125

Leu Ala Gly Asn Asn Val Ile Glu Asp Ser Arg Asp Asn Ile Ser Val
    130                 135                 140

Asp Cys Lys Gln Thr Gln Leu Cys Ile Val Gly Cys Ala Pro Ala Leu
145                 150                 155                 160

Gly Glu His Trp Thr Lys Gly Ala Val Cys Lys Ser Thr Gln Val Thr
                165                 170                 175

Thr Gly Asp Cys Pro Pro Leu Ala Leu Val Asn Thr Pro Ile Glu Asp
            180                 185                 190

Gly Asp Met Val Asp Thr Gly Phe Gly Ala Met Asp Phe Lys Leu Leu
        195                 200                 205

Gln Glu Ser Lys Ala Glu Val Pro Leu Asp Ile Val Gln Ser Thr Cys
    210                 215                 220

Lys Tyr Pro Asp Tyr Leu Lys Met Ser Ala Asp Ala Tyr Gly Asp Ser
225                 230                 235                 240

Met Trp Phe Tyr Leu Arg Arg Glu Gln Leu Phe Ala Arg His Tyr Phe
                245                 250                 255

Asn Arg Ala Gly Asn Val Gly Glu Ala Ile Pro Thr Asp Leu Tyr Trp
            260                 265                 270

Lys Gly Gly Asn Gly Arg Asp Pro Pro Ser Ser Val Tyr Val Ala
        275                 280                 285

Thr Pro Ser Gly Ser Met Ile Thr Ser Glu Ala Gln Leu Phe Asn Lys
    290                 295                 300

Pro Tyr Trp Leu Gln Arg Ala Gln Gly His Asn Asn Gly Ile Cys Trp
305                 310                 315                 320

Gly Asn Gln Val Phe Val Thr Val Val Asp Thr Thr Arg Ser Thr Asn
                325                 330                 335

Met Thr Ile Asn Ala Ala Lys Ser Thr Leu Thr Lys Tyr Asp Ala Arg
            340                 345                 350

Glu Ile Asn Gln Tyr Leu Arg His Val Glu Glu Tyr Glu Leu Gln Phe
        355                 360                 365

Val Phe Gln Leu Cys Lys Ile Thr Leu Thr Ala Glu Val Met Ala Tyr
    370                 375                 380

Leu His Asn Met Asn Asn Thr Leu Leu Asp Asp Trp Asn Ile Gly Leu
```

-continued

```
                385                 390                 395                 400
        Ser Pro Pro Val Ala Thr Ser Leu Glu Asp Lys Tyr Arg Tyr Ile Lys
                        405                 410                 415

Ser Thr Ala Ile Thr Cys Gln Arg Glu Gln Pro Ala Glu Lys Gln
                        420                 425                 430

Asp Pro Leu Ala Lys Tyr Lys Phe Trp Glu Val Asn Leu Gln Asp Ser
                        435                 440                 445

Phe Ser Ala Asp Leu Asp Gln Phe Pro Leu Gly Arg Lys Phe Leu Met
        450                 455                 460

Gln Leu Gly Pro Arg Pro Arg Pro Lys Ala Ser Val Ser Ala Ser
        465                 470                 475                 480

Lys Arg Arg Ala Ala Pro Thr Ser Ser Ser Ser Pro Ala Lys Arg
                        485                 490                 495

Lys Lys

<210> SEQ ID NO 7
<211> LENGTH: 498
<212> TYPE: PRT
<213> ORGANISM: Artificial Sequence
<220> FEATURE:
<223> OTHER INFORMATION: Synthesized Sequence

<400> SEQUENCE: 7

Met Pro Ser Asp Asn Lys Val Tyr Leu Pro Pro Thr Pro Val Ser Lys
        1               5                   10                  15

Val Val Ala Thr Asp Thr Tyr Val Lys Arg Thr Ser Ile Phe Tyr His
                        20                  25                  30

Ala Gly Ser Ser Arg Leu Leu Ala Val Gly His Pro Tyr Tyr Ser Val
                        35                  40                  45

Ser Lys Ser Gly Thr Lys Thr Asn Ile Pro Lys Val Ser Ala Tyr Gln
        50                  55                  60

Tyr Arg Val Phe Arg Val Arg Leu Pro Asp Pro Asn Lys Phe Gly Leu
        65                  70                  75                  80

Pro Asp Pro Ser Phe Tyr Asn Pro Asp Gln Glu Arg Leu Val Trp Ala
                        85                  90                  95

Cys Val Gly Leu Glu Val Gly Arg Gly Gln Pro Leu Gly Ala Gly Leu
                        100                 105                 110

Ser Gly His Pro Leu Phe Asn Arg Leu Asp Asp Thr Glu Val Ser Asn
                        115                 120                 125

Leu Ala Gly Asn Asn Val Ile Glu Asp Ser Arg Asp Asn Ile Ser Val
        130                 135                 140

Asp Cys Lys Gln Thr Gln Leu Cys Ile Val Gly Cys Ala Pro Ala Leu
        145                 150                 155                 160

Gly Glu His Trp Thr Lys Gly Ala Val Cys Lys Ser Thr Pro Gly Asn
                        165                 170                 175

Thr Gly Asp Cys Pro Pro Leu Ala Leu Val Asn Thr Pro Ile Glu Asp
                        180                 185                 190

Gly Asp Met Val Asp Thr Gly Phe Gly Ala Met Asp Phe Lys Leu Leu
                        195                 200                 205

Gln Glu Ser Lys Ala Glu Val Pro Leu Asp Ile Val Gln Ser Thr Cys
        210                 215                 220

Lys Tyr Pro Asp Tyr Leu Lys Met Ser Ala Asp Ala Tyr Gly Asp Ser
        225                 230                 235                 240

Met Trp Phe Tyr Leu Arg Arg Glu Gln Leu Phe Ala Arg His Tyr Phe
                        245                 250                 255
```

```
Asn Arg Ala Gly Lys Val Gly Glu Thr Ile Pro Ala Glu Leu Tyr Leu
            260                 265                 270

Lys Gly Ser Asn Gly Arg Glu Pro Pro Ser Ser Val Tyr Val Ala
        275                 280                 285

Thr Pro Ser Gly Ser Met Ile Thr Ser Glu Ala Gln Leu Phe Asn Lys
290                 295                 300

Pro Tyr Trp Leu Gln Arg Ala Gln Gly His Asn Asn Gly Ile Cys Trp
305                 310                 315                 320

Gly Asn Gln Val Phe Val Thr Val Val Asp Thr Thr Arg Ser Thr Asn
                325                 330                 335

Met Thr Ile Asn Ala Ala Lys Ser Thr Leu Thr Lys Tyr Asp Ala Arg
            340                 345                 350

Glu Ile Asn Gln Tyr Leu Arg His Val Glu Glu Tyr Glu Leu Gln Phe
        355                 360                 365

Val Phe Gln Leu Cys Lys Ile Thr Leu Thr Ala Glu Val Met Ala Tyr
370                 375                 380

Leu His Asn Met Asn Asn Thr Leu Leu Asp Asp Trp Asn Ile Gly Leu
385                 390                 395                 400

Ser Pro Pro Val Ala Thr Ser Leu Glu Asp Lys Tyr Arg Tyr Ile Lys
                405                 410                 415

Ser Thr Ala Ile Thr Cys Gln Arg Glu Gln Pro Pro Ala Glu Lys Gln
            420                 425                 430

Asp Pro Leu Ala Lys Tyr Lys Phe Trp Glu Val Asn Leu Gln Asp Ser
        435                 440                 445

Phe Ser Ala Asp Leu Asp Gln Phe Pro Leu Gly Arg Lys Phe Leu Met
450                 455                 460

Gln Leu Gly Pro Arg Pro Pro Arg Pro Lys Ala Ser Val Ser Ala Ser
465                 470                 475                 480

Lys Arg Arg Ala Ala Pro Thr Ser Ser Ser Ser Pro Ala Lys Arg
                485                 490                 495

Lys Lys

<210> SEQ ID NO 8
<211> LENGTH: 498
<212> TYPE: PRT
<213> ORGANISM: Artificial Sequence
<220> FEATURE:
<223> OTHER INFORMATION: Synthesized Sequence

<400> SEQUENCE: 8

Met Pro Ser Asp Asn Lys Val Tyr Leu Pro Thr Pro Val Ser Lys
1               5                   10                  15

Val Val Ala Thr Asp Thr Tyr Val Lys Arg Thr Ser Ile Phe Tyr His
            20                  25                  30

Ala Gly Ser Ser Arg Leu Leu Ala Val Gly His Pro Tyr Tyr Ser Val
        35                  40                  45

Ser Lys Ser Gly Thr Lys Thr Asn Ile Pro Lys Val Ser Ala Tyr Gln
    50                  55                  60

Tyr Arg Val Phe Arg Val Arg Leu Pro Asp Pro Asn Lys Phe Gly Leu
65                  70                  75                  80

Pro Asp Pro Ser Phe Tyr Asn Pro Asp Gln Glu Arg Leu Val Trp Ala
                85                  90                  95

Cys Val Gly Leu Glu Val Gly Arg Gly Gln Pro Leu Gly Ala Gly Leu
            100                 105                 110
```

Ser Gly His Pro Leu Phe Asn Arg Leu Asp Asp Thr Glu Val Ser Asn
115                 120                 125

Leu Ala Gly Asn Asn Val Ile Glu Asp Ser Arg Asp Asn Ile Ser Val
130                 135                 140

Asp Cys Lys Gln Thr Gln Leu Cys Ile Val Gly Cys Ala Pro Ala Leu
145                 150                 155                 160

Gly Glu His Trp Thr Lys Gly Ala Val Cys Lys Ser Thr Pro Gly Asn
            165                 170                 175

Thr Gly Asp Cys Pro Pro Leu Ala Leu Val Asn Thr Pro Ile Glu Asp
        180                 185                 190

Gly Asp Met Val Asp Thr Gly Phe Gly Ala Met Asp Phe Lys Leu Leu
    195                 200                 205

Gln Glu Ser Lys Ala Glu Val Pro Leu Asp Ile Val Gln Ser Thr Cys
210                 215                 220

Lys Tyr Pro Asp Tyr Leu Lys Met Ser Ala Asp Ala Tyr Gly Asp Ser
225                 230                 235                 240

Met Trp Phe Tyr Leu Arg Arg Glu Gln Leu Phe Ala Arg His Tyr Phe
            245                 250                 255

Asn Arg Ala Gly Asn Val Gly Glu Ala Ile Pro Thr Asp Leu Tyr Trp
        260                 265                 270

Lys Gly Gly Asn Gly Arg Asp Pro Pro Ser Ser Val Tyr Val Ala
    275                 280                 285

Thr Pro Ser Gly Ser Met Ile Thr Ser Glu Ala Gln Leu Phe Asn Lys
290                 295                 300

Pro Tyr Trp Leu Gln Arg Ala Gln Gly His Asn Asn Gly Ile Cys Trp
305                 310                 315                 320

Gly Asn Gln Val Phe Val Thr Val Val Asp Thr Thr Arg Ser Thr Asn
            325                 330                 335

Met Thr Ile Asn Ala Ala Thr Glu Gln Leu Ser Lys Tyr Asp Ala Arg
        340                 345                 350

Lys Ile Asn Gln Tyr Leu Arg His Val Glu Glu Tyr Glu Leu Gln Phe
    355                 360                 365

Val Phe Gln Leu Cys Lys Ile Thr Leu Thr Ala Glu Val Met Ala Tyr
370                 375                 380

Leu His Asn Met Asn Asn Thr Leu Leu Asp Asp Trp Asn Ile Gly Leu
385                 390                 395                 400

Ser Pro Pro Val Ala Thr Ser Leu Glu Asp Lys Tyr Arg Tyr Ile Lys
            405                 410                 415

Ser Thr Ala Ile Thr Cys Gln Arg Glu Gln Pro Pro Ala Glu Lys Gln
        420                 425                 430

Asp Pro Leu Ala Lys Tyr Lys Phe Trp Glu Val Asn Leu Gln Asp Ser
    435                 440                 445

Phe Ser Ala Asp Leu Asp Gln Phe Pro Leu Gly Arg Lys Phe Leu Met
450                 455                 460

Gln Leu Gly Pro Arg Pro Pro Arg Pro Lys Ala Ser Val Ser Ala Ser
465                 470                 475                 480

Lys Arg Arg Ala Ala Pro Thr Ser Ser Ser Ser Pro Ala Lys Arg
            485                 490                 495

Lys Lys

<210> SEQ ID NO 9
<211> LENGTH: 498
<212> TYPE: PRT
<213> ORGANISM: Artificial Sequence
<220> FEATURE:
<223> OTHER INFORMATION: Synthesized Sequence

<400> SEQUENCE: 9

```
Met Pro Ser Asp Asn Lys Val Tyr Leu Pro Pro Thr Pro Val Ser Lys
1               5                   10                  15

Val Val Ala Thr Asp Thr Tyr Val Lys Arg Thr Ser Ile Phe Tyr His
                20                  25                  30

Ala Gly Ser Ser Arg Leu Leu Ala Val Gly His Pro Tyr Tyr Ser Val
            35                  40                  45

Ser Lys Ser Gly Thr Lys Thr Asn Ile Pro Lys Val Ser Ala Tyr Gln
        50                  55                  60

Tyr Arg Val Phe Arg Val Arg Leu Pro Asp Pro Asn Lys Phe Gly Leu
65                  70                  75                  80

Pro Asp Pro Ser Phe Tyr Asn Pro Asp Gln Glu Arg Leu Val Trp Ala
                85                  90                  95

Cys Val Gly Leu Glu Val Gly Arg Gly Gln Pro Leu Gly Ala Gly Leu
            100                 105                 110

Ser Gly His Pro Leu Phe Asn Arg Leu Asp Asp Thr Glu Val Ser Asn
        115                 120                 125

Leu Ala Gly Asn Asn Val Ile Glu Asp Ser Arg Asp Asn Ile Ser Val
130                 135                 140

Asp Cys Lys Gln Thr Gln Leu Cys Ile Val Gly Cys Ala Pro Ala Leu
145                 150                 155                 160

Gly Glu His Trp Thr Lys Gly Ala Val Cys Lys Ser Thr Pro Gly Asn
                165                 170                 175

Thr Gly Asp Cys Pro Pro Leu Ala Leu Val Asn Thr Pro Ile Glu Asp
            180                 185                 190

Gly Asp Met Val Asp Thr Gly Phe Gly Ala Met Asp Phe Lys Leu Leu
        195                 200                 205

Gln Glu Ser Lys Ala Glu Val Pro Leu Asp Ile Val Gln Ser Thr Cys
210                 215                 220

Lys Tyr Pro Asp Tyr Leu Lys Met Ser Ala Asp Ala Tyr Gly Asp Ser
225                 230                 235                 240

Met Trp Phe Tyr Leu Arg Arg Glu Gln Leu Phe Ala Arg His Tyr Phe
                245                 250                 255

Asn Arg Ala Gly Asn Val Gly Glu Ala Ile Pro Thr Asp Leu Tyr Trp
            260                 265                 270

Lys Gly Gly Asn Gly Arg Asp Pro Pro Ser Ser Val Tyr Val Ala
        275                 280                 285

Thr Pro Ser Gly Ser Met Ile Thr Ser Glu Ala Gln Leu Phe Asn Lys
290                 295                 300

Pro Tyr Trp Leu Gln Arg Ala Gln Gly His Asn Asn Gly Ile Cys Trp
305                 310                 315                 320

Gly Asn Gln Val Phe Val Thr Val Val Asp Thr Thr Arg Ser Thr Asn
                325                 330                 335

Met Thr Ile Asn Ala Ala Thr Glu Gln Leu Ser Lys Tyr Asp Ala Arg
            340                 345                 350

Lys Ile Asn Gln Tyr Leu Arg His Val Glu Glu Tyr Glu Leu Gln Phe
        355                 360                 365

Val Phe Gln Leu Cys Lys Ile Thr Leu Thr Ala Glu Val Met Ala Tyr
370                 375                 380

Leu His Asn Met Asn Asn Thr Leu Leu Asp Asp Trp Asn Ile Gly Leu
385                 390                 395                 400
```

```
Ser Pro Pro Val Ala Thr Ser Leu Glu Asp Lys Tyr Arg Tyr Ile Lys
                405                 410                 415

Ser Thr Ala Ile Thr Cys Gln Arg Glu Gln Pro Ala Glu Lys Gln
        420                 425                 430

Asp Pro Leu Ala Lys Tyr Lys Phe Trp Glu Val Asn Leu Gln Asp Ser
            435                 440                 445

Phe Ser Ala Asp Leu Asp Gln Phe Pro Leu Gly Arg Lys Phe Leu Met
    450                 455                 460

Gln Leu Gly Pro Arg Pro Arg Pro Lys Ala Ser Val Ser Ala Ser
465                 470                 475                 480

Lys Arg Arg Ala Ala Pro Thr Ser Ser Ser Ser Pro Ala Lys Arg
                485                 490                 495

Lys Lys

<210> SEQ ID NO 10
<211> LENGTH: 498
<212> TYPE: PRT
<213> ORGANISM: Artificial Sequence
<220> FEATURE:
<223> OTHER INFORMATION: Synthesized Sequence

<400> SEQUENCE: 10

Met Pro Ser Asp Asn Lys Val Tyr Leu Pro Pro Thr Pro Val Ser Lys
1               5                   10                  15

Val Val Ala Thr Asp Thr Tyr Val Lys Arg Thr Ser Ile Phe Tyr His
                20                  25                  30

Ala Gly Ser Ser Arg Leu Leu Ala Val Gly His Pro Tyr Tyr Ser Val
            35                  40                  45

Ser Lys Ser Gly Thr Lys Thr Asn Ile Pro Lys Val Ser Ala Tyr Gln
    50                  55                  60

Tyr Arg Val Phe Arg Val Arg Leu Pro Asp Pro Asn Lys Phe Gly Leu
65                  70                  75                  80

Pro Asp Pro Ser Phe Tyr Asn Pro Asp Gln Glu Arg Leu Val Trp Ala
                85                  90                  95

Cys Val Gly Leu Glu Val Gly Arg Gly Gln Pro Leu Gly Val Gly Val
                100                 105                 110

Ser Gly His Pro Leu Phe Asn Arg Leu Asp Asp Thr Glu Ser Ser Ser
            115                 120                 125

Ile Ala Ile Gln Asp Thr Ala Pro Asp Ser Arg Asp Asn Val Ser Val
    130                 135                 140

Asp Pro Lys Gln Thr Gln Leu Cys Ile Val Gly Cys Ala Pro Ala Leu
145                 150                 155                 160

Gly Glu His Trp Thr Lys Gly Ala Val Cys Lys Ser Thr Pro Gly Asn
                165                 170                 175

Thr Gly Asp Cys Pro Pro Leu Ala Leu Val Asn Thr Pro Ile Glu Asp
            180                 185                 190

Gly Asp Met Val Asp Thr Gly Phe Gly Ala Met Asp Phe Lys Leu Leu
        195                 200                 205

Gln Glu Ser Lys Ala Glu Val Pro Leu Asp Ile Val Gln Ser Thr Cys
    210                 215                 220

Lys Tyr Pro Asp Tyr Leu Lys Met Ser Ala Asp Ala Tyr Gly Asp Ser
225                 230                 235                 240

Met Trp Phe Tyr Leu Arg Arg Glu Gln Leu Phe Ala Arg His Tyr Phe
                245                 250                 255
```

Asn Arg Ala Gly Asn Val Gly Glu Ala Ile Pro Thr Asp Leu Tyr Trp
                260                 265                 270

Lys Gly Gly Asn Gly Arg Asp Pro Pro Ser Ser Val Tyr Val Ala
            275                 280                 285

Thr Pro Ser Gly Ser Met Ile Thr Ser Glu Ala Gln Leu Phe Asn Lys
        290                 295                 300

Pro Tyr Trp Leu Gln Arg Ala Gln Gly His Asn Asn Gly Ile Cys Trp
305                 310                 315                 320

Gly Asn Gln Val Phe Val Thr Val Val Asp Thr Thr Arg Ser Thr Asn
                325                 330                 335

Met Thr Ile Asn Ala Ala Thr Glu Gln Leu Ser Lys Tyr Asp Ala Arg
            340                 345                 350

Lys Ile Asn Gln Tyr Leu Arg His Val Glu Glu Tyr Glu Leu Gln Phe
        355                 360                 365

Val Phe Gln Leu Cys Lys Ile Thr Leu Thr Ala Glu Val Met Ala Tyr
370                 375                 380

Leu His Asn Met Asn Asn Thr Leu Leu Asp Asp Trp Asn Ile Gly Leu
385                 390                 395                 400

Ser Pro Pro Val Ala Thr Ser Leu Glu Asp Lys Tyr Arg Tyr Ile Lys
                405                 410                 415

Ser Thr Ala Ile Thr Cys Gln Arg Glu Gln Pro Pro Ala Glu Lys Gln
            420                 425                 430

Asp Pro Leu Ala Lys Tyr Lys Phe Trp Glu Val Asn Leu Gln Asp Ser
        435                 440                 445

Phe Ser Ala Asp Leu Asp Gln Phe Pro Leu Gly Arg Lys Phe Leu Met
450                 455                 460

Gln Leu Gly Pro Arg Pro Arg Pro Lys Ala Ser Val Ser Ala Ser
465                 470                 475                 480

Lys Arg Arg Ala Ala Pro Thr Ser Ser Ser Ser Pro Ala Lys Arg
                485                 490                 495

Lys Lys

<210> SEQ ID NO 11
<211> LENGTH: 498
<212> TYPE: PRT
<213> ORGANISM: Artificial Sequence
<220> FEATURE:
<223> OTHER INFORMATION: Synthesized Sequence

<400> SEQUENCE: 11

Met Pro Ser Asp Asn Lys Val Tyr Leu Pro Thr Pro Val Ser Lys
1               5                   10                  15

Val Val Ala Thr Asp Thr Tyr Val Lys Arg Thr Ser Ile Phe Tyr His
            20                  25                  30

Ala Gly Ser Ser Arg Leu Leu Ala Val Gly His Pro Tyr Tyr Ser Val
        35                  40                  45

Ser Lys Ser Gly Thr Lys Thr Asn Ile Pro Lys Val Ser Ala Tyr Gln
    50                  55                  60

Tyr Arg Val Phe Arg Val Arg Leu Pro Asp Pro Asn Lys Phe Gly Leu
65                  70                  75                  80

Pro Asp Pro Ser Phe Tyr Asn Pro Asp Gln Glu Arg Leu Val Trp Ala
                85                  90                  95

Cys Val Gly Leu Glu Val Gly Arg Gly Gln Pro Leu Gly Ala Gly Leu
            100                 105                 110

Ser Gly His Pro Leu Phe Asn Arg Leu Asp Asp Thr Glu Val Ser Asn

```
                115                 120                 125
Leu Ala Gly Asn Asn Val Ile Glu Asp Ser Arg Asp Asn Ile Ser Val
130                 135                 140
Asp Cys Lys Gln Thr Gln Leu Cys Ile Val Gly Cys Ala Pro Ala Leu
145                 150                 155                 160
Gly Glu His Trp Thr Lys Gly Ala Val Cys Lys Ser Thr Pro Gly Asn
                165                 170                 175
Thr Gly Asp Cys Pro Pro Leu Ala Leu Val Asn Thr Pro Ile Glu Asp
                180                 185                 190
Gly Asp Met Val Asp Thr Gly Phe Gly Ala Met Asp Phe Lys Leu Leu
                195                 200                 205
Gln Glu Ser Lys Ala Glu Val Pro Leu Asp Ile Val Gln Ser Thr Cys
210                 215                 220
Lys Tyr Pro Asp Tyr Leu Lys Met Ser Ala Asp Ala Tyr Gly Asp Ser
225                 230                 235                 240
Met Trp Phe Tyr Leu Arg Arg Glu Gln Leu Phe Ala Arg His Phe Phe
                245                 250                 255
Asn Arg Ala Gly Val Ile Gly Glu Glu Ile Pro Asn Asp Leu Tyr Ile
                260                 265                 270
Lys Gly Ser Asn Gly Arg Asp Pro Pro Ser Ser Val Tyr Val Ala
                275                 280                 285
Thr Pro Ser Gly Ser Met Ile Thr Ser Glu Ala Gln Leu Phe Asn Lys
                290                 295                 300
Pro Tyr Trp Leu Gln Arg Ala Gln Gly His Asn Asn Gly Ile Cys Trp
305                 310                 315                 320
Gly Asn Gln Val Phe Val Thr Val Val Asp Thr Thr Arg Ser Thr Asn
                325                 330                 335
Met Thr Ile Asn Ala Ala Thr Glu Gln Leu Ser Lys Tyr Asp Ala Arg
                340                 345                 350
Lys Ile Asn Gln Tyr Leu Arg His Val Glu Glu Tyr Glu Leu Gln Phe
                355                 360                 365
Val Phe Gln Leu Cys Lys Ile Thr Leu Thr Ala Glu Val Met Ala Tyr
                370                 375                 380
Leu His Asn Met Asn Asn Thr Leu Leu Asp Asp Trp Asn Ile Gly Leu
385                 390                 395                 400
Ser Pro Pro Val Ala Thr Ser Leu Glu Asp Lys Tyr Arg Tyr Ile Lys
                405                 410                 415
Ser Thr Ala Ile Thr Cys Gln Arg Glu Gln Pro Pro Ala Glu Lys Gln
                420                 425                 430
Asp Pro Leu Ala Lys Tyr Lys Phe Trp Glu Val Asn Leu Gln Asp Ser
                435                 440                 445
Phe Ser Ala Asp Leu Asp Gln Phe Pro Leu Gly Arg Lys Phe Leu Met
                450                 455                 460
Gln Leu Gly Pro Arg Pro Arg Pro Lys Ala Ser Val Ser Ala Ser
465                 470                 475                 480
Lys Arg Arg Ala Ala Pro Thr Ser Ser Ser Ser Pro Ala Lys Arg
                485                 490                 495
Lys Lys

<210> SEQ ID NO 12
<211> LENGTH: 1509
<212> TYPE: DNA
<213> ORGANISM: Human papillomavirus type 66
```

<400> SEQUENCE: 12

```
atggccatgt ggaggcccag cgacaacaag gtgtacctgc cccccacccc cgtgagcaag    60
gtggtggcca ccgacaccta cgtgaagagg accagcatct tctaccacgc cggcagcagc   120
aggctgctgg ccgtgggcca cccctactac agcgtgagca agagcggcac caagaccaac   180
atccccaagg tgagcgccta ccagtacagg gtgttcaggg tgaggctccc cgaccccaac   240
aagttcggcc tgcccgaccc cagcttctac aaccccgacc aggagaggct ggtgtgggcc   300
tgcgtgggcc tggaggtggg caggggccag cccctgggcg ccggcctgag cggccacccc   360
ctgttcaaca ggctggacga caccgaggtg agcaacctgg ccggcaacaa cgtgatcgag   420
gacagcaggg acaacatcag cgtggactgc aagcagaccc agctgtgcat cgtgggctgc   480
gcccccgccc tgggcgagca ctggaccaag ggcgccgtgt gcaagagcac ccccggcaac   540
accggcgact gcccccccct ggccctggtg aacaccccca tcgaggacgg cgacatggtg   600
gacaccggct tcggcgccat ggacttcaag ctgctgcagg agagcaaggc cgaggtgccc   660
ctggacatcg tgcagagcac ctgcaagtac cccgactacc tgaagatgag cgccgacgcc   720
tacggcgaca gcatgtggtt ctacctgagg agggagcagc tgttcgccag gcactacttc   780
aacagggccg gcaacgtggg cgaggccatc cccaccgacc tgtactggaa gggcggcaac   840
ggcagggacc ccccccccag cagcgtgtac gtggccaccc ccagcggcag catgatcacc   900
agcgaggccc agctgttcaa caagccctac tggctgcaga gggcccaggg ccacaacaac   960
ggcatctgct ggggcaacca ggtgttcgtg accgtggtgg acaccaccag gagcaccaac  1020
atgaccatca cgccgccaa gagccacctg accaagtacg acgccaggga gatcaaccag  1080
tacctgaggc acgtggagga gtacgagctg cagttcgtgt tccagctgtg caagatcacc  1140
ctgaccgccg aggtgatggc ctacctgcac aacatgaaca cacccctgct ggacgactgg  1200
aacatcggcc tgagcccccc cgtggccacc agcctggagg acaagtacag gtacatcaag  1260
agcaccgcca tcacctgcca gagggagcag ccccccgccg agaagcagga ccccctggcc  1320
aagtacaagt tctgggaggt gaacctgcag gacagcttca gcgccgacct ggaccagttc  1380
ccccctgggca ggaagttcct gatgcagctg ggccccaggc cccccaggcc aaggccagc  1440
gtgagcgcca gcaagaggag ggccgccccc accagcagca gcagcagccc cgccaagagg  1500
aagaagtaa                                                          1509
```

<210> SEQ ID NO 13
<211> LENGTH: 1500
<212> TYPE: DNA
<213> ORGANISM: Human papillomavirus type 56

<400> SEQUENCE: 13

```
atggccacct ggcggcccag cgagaacaag gtgtacctgc cccccacccc cgtgtccaag    60
gtggtggcca ccgacagcta cgtgaagcgg accagcatct tctaccacgc cggcagcagc   120
agactgctgg ccgtgggcca cccctactac agcgtgacca aggacaacac caagaccaac   180
atccccaagg tgtccgccta ccagtaccgg gtgttcagag tgcggctgcc tgaccctaac   240
aagttcggcc tgcccgacac caatatctac aaccccgacc aggaacggct ggtctgggcc   300
tgcgtgggcc tggaagtggg cagaggccag cctctgggag ctggcctgag cggccacccc   360
ctgttcaacc ggctggacga caccgagagc agcaacctgg ccaacaacaa cgtgatcgag   420
gacagccggg acaacatcag cgtggacggc aagcagaccc agctgtgcat cgtgggctgc   480
acacccgcca tgggcgagca ctggaccaag ggcgccgtgt gcaagagcac ccaggtcacc   540
```

```
accggcgact gccccctct ggccctgatc aacacccca tcgaggacgg cgacatgatc      600
gacaccggct tcggcgccat ggacttcaag gtgctgcagg aaagcaaggc cgaggtcccc      660
ctggacatcg tgcagagcac ctgcaagtac cccgactacc tgaagatgag cgccgacgcc      720
tacgccgaca gcatgtggtt ctacctgcgg cgggagcagc tgttcgcccg cactacttc       780 aacagagccg gcaaagtggg cgagacaatc cccgccgagc tgtacctgaa gggcagcaac      840
ggacgggagc ctcctcccag cagcgtgtac gtggccaccc ccagcggcag catgatcacc      900
agcgaggccc agctgttcaa caagccctac tggctgcagc gggcccaggg ccacaacaac      960
ggcatctgct ggggcaacca gctgttcgtg accgtcgtgg acactacccg gtccaccaac     1020
atgaccatca gcaccgccac cgagcagctg tccaagtacg acgcccggaa gatcaaccag     1080
tacctgcggc acgtggagga atatgagctg cagttcgtct ttcagctgtg caagatcacc     1140
ctgagcgccg aagtgatggc ctacctgcac aacatgaacg ccaacctgct ggaagattgg     1200
aacatcggcc tgagcccccc tgtggctacc tctctggaag ataagtacag atacgtgcgg     1260
agcaccgcca tcacctgcca gagagagcag cccccaccg agaagcagga cccctggcc      1320 aagtacaagt tctgggacgt gaacctgcag gacagcttca gcaccgacct ggaccagttc     1380
cccctgggcc ggaagttcct gatgcagctg gcaccagat ccaagcccgc cgtggccaca     1440
agcaagaagc ggagcgcccc cacaagcacc agcacccccg ccaagcggaa gcggagatga     1500

<210> SEQ ID NO 14
<211> LENGTH: 1500
<212> TYPE: DNA
<213> ORGANISM: Human papillomavirus type 53

<400> SEQUENCE: 14
atggccgtgt ggaggcccag cgacagcaag gtgtacctgc cccccacccc cgtgagcaag       60
gtgatcacca ccgacgccta cgtgaagagg accaccatct tctaccgcg cggcagcagc       120 aggctgctga ccgtgggcca ccctactac cccatcagca gagcggcaa ggccgacatc        180 cccaaggtga cgccttcca gtacagggtg ttcagggtga gctgcccga ccccaacaag       240 ttcggcctgc ccgacaccaa catcttcaac cccgaccagg agaggctggt gtgggcctgc      300
gtgggcctgg agatcggcag gggccagccc ctgggcgtgg cgtgagcgg ccacccctg      360 ttcaacaggc tggacgacac cgagagcagc agcatcgcca tccaggacac cgcccccgac      420
agcagggaca cgtgagcgt ggaccccaag cagacccagc tgtgcatcat cggctgcgcc      480
cccgccatcg cgagcactg accaagggc accgcctgca ggagcacccc caccaccgcc      540
ggcgactgcc cccccctgga gctgatcaac agccccatcg aggacggcga catggtggac      600
accggcttcg cgccctgaa cttcaaggcc ctgcaggaga gcaagagcga cgtgcccctg      660
gacatcgtgc agagcaccctg caagtacccc gactacctga gatgagcgc cgacgcctac      720 ggcgacagca tgtggttcta cctgaggagg agcagctgt tcaccaggca cttcttcaac      780
agggccggcg tgatcggcga ggagatcccc aacgacctgt acatcaaggg cagcaacggc      840 agggacccccc ccccagcag cgtgtacgtg ccaccccca gcggcagcat gatcaccagc      900
gaggcccagc tgttcaacaa gccctactgg ctgcagaggg cccagggcca acaacggc      960 atctgctgga caaccagct gttcgtgacc gtggtggaca ccaccaggaa caccaacatg     1020
accctgagcg ccaccaccca gagcatgagc cctacaaca gcaagcagat caagcagtac     1080
gtgaggcacg ccgaggagta cgagctgcag ttcgtgttcc agctgtgcaa gatcagcctg     1140
```

```
agcgccgagg tgatggccta cctgcacacc atgaacagca ccctgctgga ggactggaac      1200
atcggcctga gccccccgt ggccaccagc ctggaggaca agtacaggta cgtgaagagc       1260
gccgccatca cctgccagaa ggaccagccc cccccgaga agcaggaccc cctgagcaag       1320
tacaagttct gggaggtgaa cctgcagaac agcttcagcg ccgacctgga ccagttcccc     1380
ctgggcagga agttcctgat gcaggtgggc gtgaggacca agcccccgt gagcagcaag      1440 aagaggagcg ccagcaccac cagcaccagc gcccccagca gcaagaggaa gaggaagtaa    1500
```

<210> SEQ ID NO 15
<211> LENGTH: 1497
<212> TYPE: DNA
<213> ORGANISM: Artificial Sequence
<220> FEATURE:
<223> OTHER INFORMATION: Synthesized Sequence

<400> SEQUENCE: 15

```
atgcccagcg acaacaaggt gtacctgccc cccaccccg tgagcaaggt ggtggccacc        60
gacacctacg tgaagaggac cagcatcttc taccacgccg gcagcagcag gctgctggcc     120
gtgggccacc cctactacag cgtgaccaag acaacacca agaccaacat ccccaaggtg     180
tccgcctacc agtacagggt gttcagggtg aggctcccg accccaacaa gttcggcctg      240
cccgacccca gcttctacaa cccgaccag gagaggctgg tgtgggcctg cgtgggcctg       300
gaggtgggca ggggccagcc cctgggcgcc ggcctgagcg ccacccct gttcaacagg      360 ctggacgaca ccgaggtgag caacctggcc ggcaacaacg tgatcgagga cagcagggac     420
aacatcagcg tggactgcaa gcagaccag ctgtgcatcg tgggctgcgc ccccgccctg      480
ggcgagcact ggaccaaggg cgccgtgtgc aagagcaccc ccggcaacac cggcgactgc     540 cccccctgg ccctggtgaa cacccccatc gaggacggcg acatggtgga caccggcttc     600
ggcgccatgg acttcaagct gctgcaggag agcaaggccg aggtgccct ggacatcgtg      660 cagagcacct gcaagtaccc cgactacctg aagatgagcg ccgacgccta cggcgacagc     720
atgtggttct acctgaggag ggagcagctg ttcgccaggc actacttcaa cagggccggc     780
aacgtgggcg aggccatccc caccgacctg tactggaagg cggcaacgg cagggacccc    840 ccccccagca gcgtgtacgt ggccaccccc agcggcagca tgatcaccag cgaggcccag     900
ctgttcaaca gccctactg gctgcagagg gcccagggcc acaacaacgg catctgctgg       960
ggcaaccagg tgttcgtgac cgtggtggac accaccagga gcaccaacat gaccatcaac    1020
gccgccaaga gcaccctgac caagtacgac gccaggagga tcaaccagta cctgaggcac   1080
gtggaggagt acgagctgca gttcgtgttc cagctgtgca agatcaccct gaccgccgag    1140
gtgatggcct acctgcacaa catgaacaac ccctgctgg acgactggaa catcggcctg     1200
agcccccccg tggccaccag cctggaggac aagtacaggt acatcaagag caccgccatc     1260
acctgccaga gggagcagcc cccgccgag aagcaggacc ccctggccaa gtacaagttc     1320
tgggaggtga acctgcagga cagcttcagc gccgacctgg accagttccc cctgggcagg    1380
aagttcctga tgcagctggg ccccaggccc ccaggccca aggccagcgt gagcgccagc    1440
aagaggaggg ccgcccccac cagcagcagc agcagcccg ccaagaggaa gaagtaa         1497
```

<210> SEQ ID NO 16
<211> LENGTH: 1497
<212> TYPE: DNA
<213> ORGANISM: Artificial Sequence
<220> FEATURE:
<223> OTHER INFORMATION: Synthesized Sequence

<400> SEQUENCE: 16

```
atgcccagcg acaacaaggt gtacctgccc cccacccccg tgagcaaggt ggtggccacc    60
gacacctacg tgaagaggac cagcatcttc taccacgccg gcagcagcag gctgctggcc   120
gtgggccacc cctactacag cgtgagcaag agcggcacca agaccaacat ccccaaggtg   180
agcgcctacc agtacagggt gttcagggtg aggctccccg accccaacaa gttcggcctg   240
cccgacccca gcttctacaa ccccgaccag gagaggctgg tgtgggcctg cgtgggcctg   300
gaggtgggca gaggccagcc tctgggagct ggcctgagcg ccacccccct gttcaaccgg   360
ctggacgaca ccgagagcag caacctggcc aacaacaacg tgatcgagga cagccgggac   420
aacatcagcg tggacggcaa gcagacccag ctgtgcatcg tgggctgcgc ccccgccctg   480
ggcgagcact ggaccaaggg cgccgtgtgc aagagcaccc ccggcaacac cggcgactgc   540
ccccccctgg ccctggtgaa cacccccatc gaggacggcg acatggtgga caccggcttc   600
ggcgccatgg acttcaagct gctgcaggag agcaaggccg aggtgccct ggacatcgtg    660
cagagcacct gcaagtaccc cgactacctg aagatgagcg ccgacgccta cggcgacagc   720
atgtggttct acctgaggag ggagcagctg ttcgccaggc actacttcaa cagggccggc   780
aacgtgggcg aggccatccc caccgacctg tactggaagg gcggcaacgg cagggacccc   840
cccccccagca gcgtgtacgt ggccaccccc agcggcagca tgatcaccag cgaggcccag   900
ctgttcaaca gccctactg gctgcagagg gcccagggcc acaacaacgg catctgctgg   960
ggcaaccagg tgttcgtgac cgtggtggac accaccagga gcaccaacat gaccatcaac  1020
gccgccaaga gcaccctgac caagtacgac gccagggaga tcaaccagta cctgaggcac  1080
gtggaggagt acgagctgca gttcgtgttc cagctgtgca agatcaccct gaccgccgag  1140
gtgatggcct acctgcacaa catgaacaac accctgctgg acgactggaa catcggcctg  1200
agccccccg tggccaccag cctggaggac aagtacaggt acatcaagag caccgccatc  1260
acctgccaga gggagcagcc ccccgccgag aagcaggacc ccctggccaa gtacaagttc  1320
tgggaggtga acctgcagga cagcttcagc gccgacctgg accagttccc cctgggcagg  1380
aagttcctga tgcagctggg ccccaggccc ccaggccca aggccagcgt gagcgccagc  1440
aagaggaggg ccgcccccac cagcagcagc agcagccccg ccaagaggaa gaagtaa    1497
```

<210> SEQ ID NO 17
<211> LENGTH: 1497
<212> TYPE: DNA
<213> ORGANISM: Artificial Sequence
<220> FEATURE:
<223> OTHER INFORMATION: Synthesized Sequence

<400> SEQUENCE: 17

```
atgcccagcg acaacaaggt gtacctgccc cccacccccg tgagcaaggt ggtggccacc    60
gacacctacg tgaagaggac cagcatcttc taccacgccg gcagcagcag gctgctggcc   120
gtgggccacc cctactacag cgtgagcaag agcggcacca agaccaacat ccccaaggtg   180
agcgcctacc agtacagggt gttcagggtg aggctccccg accccaacaa gttcggcctg   240
cccgacccca gcttctacaa ccccgaccag gagaggctgg tgtgggcctg cgtgggcctg   300
gaggtgggca ggggccagcc cctgggcgcc ggcctgagcg ccacccccct gttcaacagg   360
ctggacgaca ccgaggtgag caacctggcc ggcaacaacg tgatcgagga cagcagggac   420
aacatcagcg tggactgcaa gcagacccag ctgtgcatcg tgggctgcgc ccccgccctg   480
```

```
ggcgagcact ggaccaaggg cgccgtgtgc aagagcaccc aggtcaccac cggcgactgc      540 cccctctgg ccctggtgaa cccccatc gaggacggcg acatggtgga caccggcttc         600
ggcgccatgg acttcaagct gctgcaggag agcaaggccg aggtgcccct ggacatcgtg      660
cagagcacct gcaagtaccc cgactacctg aagatgagcg ccgacgccta cggcgacagc      720
atgtggttct acctgaggag ggagcagctg ttcgccaggc actacttcaa cagggccggc      780
aacgtgggcg aggccatccc caccgacctg tactggaagg cggcaacgg cagggacccc       840 ccccccagca gcgtgtacgt ggccaccccc agcggcagca tgatcaccag cgaggcccag      900
ctgttcaaca agccctactg gctgcagagg gcccagggcc acaacaacgg catctgctgg      960
ggcaaccagg tgttcgtgac cgtggtggac accaccagga gcaccaacat gaccatcaac     1020
gccgccaaga gcaccctgac caagtacgac gccagggaga tcaaccagta cctgaggcac     1080
gtggaggagt acgagctgca gttcgtgttc cagctgtgca agatcaccct gaccgccgag     1140
gtgatggcct acctgcacaa catgaacaac accctgctgg acgactggaa catcggcctg     1200
agcccccccg tggccaccag cctggaggac aagtacaggt acatcaagag caccgccatc     1260
acctgccaga gggagcagcc ccccgccgag aagcaggacc ccctggccaa gtacaagttc     1320
tgggaggtga acctgcagga cagcttcagc gccgacctgg accagttccc cctgggcagg     1380
aagttcctga tgcagctggg ccccaggccc ccaggccca aggccagcgt gagcgccagc      1440
aagaggaggg ccgcccccac cagcagcagc agcagccccg ccaagaggaa gaagtaa       1497
```

<210> SEQ ID NO 18
<211> LENGTH: 1497
<212> TYPE: DNA
<213> ORGANISM: Artificial Sequence
<220> FEATURE:
<223> OTHER INFORMATION: Synthesized Sequence

<400> SEQUENCE: 18

```
atgcccagcg acaacaaggt gtacctgccc cccaccccg tgagcaaggt ggtggccacc        60
gacacctacg tgaagaggac cagcatcttc taccacgccg gcagcagcag gctgctggcc      120
gtgggccacc cctactacag cgtgagcaag agcggcacca agaccaacat ccccaaggtg      180
agcgcctacc agtacagggt gttcagggtg aggctccccg accccaacaa gttcggcctg      240
cccgacccca gcttctacaa ccccgaccag gagaggctgg tgtgggcctg cgtgggcctg      300
gaggtgggca gggccagcc cctgggcgcc ggcctgagcg gccaccccct gttcaacagg      360
ctggacgaca ccgaggtgag caacctggcc ggcaacaacg tgatcgagga cagcagggac      420
aacatcagcg tggactgcaa gcagacccag ctgtgcatcg tgggctgcgc ccccgccctg      480
ggcgagcact ggaccaaggg cgccgtgtgc aagagcaccc ccggcaacac cggcgactgc      540 cccccctgg ccctggtgaa cccccatc gaggacggcg acatggtgga caccggcttc         600
ggcgccatgg acttcaagct gctgcaggag agcaaggccg aggtgcccct ggacatcgtg      660
cagagcacct gcaagtaccc cgactacctg aagatgagcg ccgacgccta cggcgacagc      720
atgtggttct acctgaggag ggagcagctg ttcgccaggc actacttcaa cagagccggc      780
aaagtgggcg agacaatccc cgccgagctg tacctgaagg cagcaacgg acgggagcct      840 cctcccagca gcgtgtacgt ggccaccccc agcggcagca tgatcaccag cgaggcccag      900
ctgttcaaca agccctactg gctgcagagg gcccagggcc acaacaacgg catctgctgg      960
ggcaaccagg tgttcgtgac cgtggtggac accaccagga gcaccaacat gaccatcaac     1020
gccgccaaga gcaccctgac caagtacgac gccagggaga tcaaccagta cctgaggcac     1080
```

```
gtggaggagt acgagctgca gttcgtgttc cagctgtgca agatcaccct gaccgccgag    1140
gtgatggcct acctgcacaa catgaacaac accctgctgg acgactggaa catcggcctg    1200 agccccccg tggccaccag cctggaggac aagtacaggt acatcaagag caccgccatc     1260
acctgccaga gggagcagcc ccccgccgag aagcaggacc ccctggccaa gtacaagttc    1320
tgggaggtga acctgcagga cagcttcagc gccgacctgg accagttccc cctgggcagg    1380
aagttcctga tgcagctggg ccccaggccc ccaggcccag gccagcgt gagcgccagc      1440 aagaggaggg ccgcccccac cagcagcagc agcagccccg ccaagaggaa gaagtaa       1497
```

<210> SEQ ID NO 19
<211> LENGTH: 1497
<212> TYPE: DNA
<213> ORGANISM: Artificial Sequence
<220> FEATURE:
<223> OTHER INFORMATION: Synthesized Sequence

<400> SEQUENCE: 19

```
atgcccagcg acaacaaggt gtacctgccc ccaccccg tgagcaaggt ggtggccacc       60
gacacctacg tgaagaggac cagcatcttc taccacgccg gcagcagcag gctgctggcc    120
gtgggccacc cctactacag cgtgagcaag agcggcacca agaccaacat ccccaaggtg    180
agcgcctacc agtacaggt gttcaggtg aggctccccg accccaacaa gttcggcctg     240
cccgacccca gcttctacaa ccccgaccag gagaggctgg tgtgggcctg cgtgggcctg    300
gaggtgggca ggggccagcc cctgggcgcc ggcctgagcg ccaccccct gttcaacagg     360 ctggacgaca ccgaggtgag caacctggcc ggcaacaacg tgatcgagga cagcagggac    420
aacatcagcg tggactgcaa gcagacccag ctgtgcatcg tgggctgcgc ccccgccctg    480
ggcgagcact ggaccaaggg cgccgtgtgc aagagcaccc ccggcaacac cggcgactgc    540
ccccccctgg ccctggtgaa cacccccatc gaggacggcg acatggtgga caccggcttc    600
ggcgccatgg acttcaagct gctgcaggag agcaaggccg aggtgcccct ggacatcgtg    660
cagagcacct gcaagtaccc cgactacctg aagatgagcg ccgacgccta cggcgacagc    720
atgtggttct acctgaggag ggagcagctg ttcgccaggc actacttcaa cagggccggc    780
aacgtgggcg aggccatccc caccgacctg tactggaagg gcggcaacgg cagggacccc    840 cccccagca gcgtgtacgt ggccaccccc agcggcagca tgatcaccag cgaggcccag    900
ctgttcaaca gcccctactg gctgcagagg gcccagggcc acaacaacgg catctgctgg    960
ggcaaccagg tgttcgtgac cgtggtggac accaccagga gcaccaacat gaccatcaac    1020
gccgccaccg agcagctgtc caagtacgac gcccggaaga tcaaccagta cctgaggcac    1080
gtggaggagt acgagctgca gttcgtgttc cagctgtgca agatcaccct gaccgccgag    1140
gtgatggcct acctgcacaa catgaacaac accctgctgg acgactggaa catcggcctg    1200 agccccccg tggccaccag cctggaggac aagtacaggt acatcaagag caccgccatc     1260
acctgccaga gggagcagcc ccccgccgag aagcaggacc ccctggccaa gtacaagttc    1320
tgggaggtga acctgcagga cagcttcagc gccgacctgg accagttccc cctgggcagg    1380
aagttcctga tgcagctggg ccccaggccc ccaggcccag gccagcgt gagcgccagc      1440 aagaggaggg ccgcccccac cagcagcagc agcagccccg ccaagaggaa gaagtaa       1497
```

<210> SEQ ID NO 20
<211> LENGTH: 1494
<212> TYPE: DNA

<213> ORGANISM: Artificial Sequence
<220> FEATURE:
<223> OTHER INFORMATION: Synthesized Sequence

<400> SEQUENCE: 20

```
atgcccagcg acaacaaggt gtacctgccc cccaccccg tgagcaaggt ggtggccacc     60
gacacctacg tgaagaggac cagcatcttc taccacgccg gcagcagcag gctgctggcc    120
gtgggccacc cctactaccc catcagcaag agcggcaagg ccgacatccc caaggtgagc    180
gcctaccagt acagggtgtt cagggtgagg ctccccgacc caacaagtt cggcctgccc     240
gaccccagct tctacaaccc cgaccaggag aggctggtgt gggcctgcgt gggcctggag    300
gtgggcaggg gccagcccct gggcgccggc ctgagcggcc accccctgtt caacaggctg    360
gacgacaccg aggtgagcaa cctggccggc aacaacgtga tcgaggacag cagggacaac    420
atcagcgtgg actgcaagca gacccagctg tgcatcgtgg gctgcgcccc cgccctgggc    480
gagcactgga ccaagggcgc cgtgtgcaag agcaccccg caacaccgg cgactgcccc     540
cccctggccc tggtgaacac ccccatcgag gacggcgaca tggtggacac cggcttcggc    600
gccatggact tcaagctgct gcaggagagc aaggccgagg tgcccctgga catcgtgcag    660
agcacctgca agtaccccga ctacctgaag atgagcgccg acgcctacgg cgacagcatg    720
tggttctacc tgaggaggga gcagctgttc gccaggcact acttcaacag gccggcaac    780
gtgggcgagg ccatccccac cgacctgtac tggaagggcg caacggcag gaccccccc     840
cccagcagcg tgtacgtggc caccccagc ggcagcatga tcaccagcga ggcccagctg    900
ttcaacaagc cctactggct gcagagggcc caggccaca caacggcat ctgctggggc    960
aaccaggtgt tcgtgaccgt ggtggacacc accaggagca ccaacatgac catcaacgcc   1020
gccaccgagc agctgtccaa gtacgacgcc cggaagatca ccagtacct gaggcacgtg   1080
gaggagtacg agctgcagtt cgtgttccag ctgtgcaaga tcaccctgac cgccgaggtg   1140
atggcctacc tgcacaacat gaacaacacc ctgctggacg actggaacat cggcctgagc   1200
cccccgtgg ccaccagcct ggaggacaag tacaggtaca tcaagagcac cgccatcacc   1260
tgccagaggg agcagccccc cgccgagaag caggaccccc tggccaagta caagttctgg   1320
gaggtgaacc tgcaggacag cttcagcgcc gacctggacc agttcccct gggcaggaag    1380
ttcctgatgc agctgggccc caggcccccc aggcccaagg ccagcgtgag cgccagcaag   1440
aggagggccg ccccaccag cagcagcagc agccccgcca gaggaagaa gtaa           1494
```

<210> SEQ ID NO 21
<211> LENGTH: 1497
<212> TYPE: DNA
<213> ORGANISM: Artificial Sequence
<220> FEATURE:
<223> OTHER INFORMATION: Synthesized Sequence

<400> SEQUENCE: 21

```
atgcccagcg acaacaaggt gtacctgccc cccaccccg tgagcaaggt ggtggccacc     60
gacacctacg tgaagaggac cagcatcttc taccacgccg gcagcagcag gctgctggcc    120
gtgggccacc cctactacag cgtgagcaag agcggcacca agaccaacat ccccaaggtg    180
agcgcctacc agtacagggt gttcagggtg aggctccccg accccaacaa gttcggcctg    240
cccgacccca gcttctacaa ccccgaccag gagaggctgg tgtgggcctg cgtgggcctg    300
gaggtgggca gggccagcc cctgggcgtg ggcgtgagcg ccacccct gttcaacagg      360
ctggacgaca ccgagagcag cagcatcgcc atccaggaca ccgcccccga cagcagggac    420
```

| | |
|---|---|
| aacgtgagcg tggaccccaa gcagacccag ctgtgcatcg tgggctgcgc ccccgccctg | 480 |
| ggcgagcact ggaccaaggg cgccgtgtgc aagagcaccc ccggcaacac cggcgactgc | 540 |
| ccccccctgg ccctggtgaa caccccatc gaggacggcg acatggtgga caccggcttc | 600 |
| ggcgccatgg acttcaagct gctgcaggag agcaaggccg aggtgcccct ggacatcgtg | 660 |
| cagagcacct gcaagtaccc cgactacctg aagatgagcg ccgacgccta cggcgacagc | 720 |
| atgtggttct acctgaggag ggagcagctg ttcgccaggc actacttcaa cagggccggc | 780 |
| aacgtgggcg aggccatccc caccgacctg tactggaagg gcggcaacgg cagggacccc | 840 |
| cccccccagca gcgtgtacgt ggccaccccc agcggcagca tgatcaccag cgaggcccag | 900 |
| ctgttcaaca agccctactg gctgcagagg gcccagggcc acaacaacgg catctgctgg | 960 |
| ggcaaccagg tgttcgtgac cgtggtggac accaccagga gcaccaacat gaccatcaac | 1020 |
| gccgccaccg agcagctgtc caagtacgac gcccggaaga tcaaccagta cctgaggcac | 1080 |
| gtggaggagt acgagctgca gttcgtgttc cagctgtgca agatcacccct gaccgccgag | 1140 |
| gtgatggcct acctgcacaa catgaacaac accctgctgg acgactggaa catcggcctg | 1200 |
| agccccccg tggccaccag cctggaggac aagtacaggt acatcaagag caccgccatc | 1260 |
| acctgccaga gggagcagcc ccccgccgag aagcaggacc ccctggccaa gtacaagttc | 1320 |
| tgggaggtga acctgcagga cagcttcagc gccgacctgg accagttccc cctgggcagg | 1380 |
| aagttcctga tgcagctggg ccccaggccc ccaggccca aggccagcgt gagcgccagc | 1440 |
| aagaggaggg ccgcccccac cagcagcagc agcagccccg ccaagaggaa gaagtaa | 1497 |

<210> SEQ ID NO 22
<211> LENGTH: 1497
<212> TYPE: DNA
<213> ORGANISM: Artificial Sequence
<220> FEATURE:
<223> OTHER INFORMATION: Synthesized Sequence

<400> SEQUENCE: 22

| | |
|---|---|
| atgcccagcg acaacaaggt gtacctgccc ccaccccg tgagcaaggt ggtggccacc | 60 |
| gacacctacg tgaagaggac cagcatcttc taccacgccg cagcagcag gctgctggcc | 120 |
| gtgggccacc cctactacag cgtgagcaag agcggcacca agaccaacat ccccaaggtg | 180 |
| agcgcctacc agtacagggt gttcagggtg aggctccccg accccaacaa gttcggcctg | 240 |
| cccgacccca gcttctacaa ccccgaccag gagaggctgg tgtgggcctg cgtgggcctg | 300 |
| gaggtgggca ggggccagcc cctgggcgcc ggcctgagcg ccacccccct gttcaacagg | 360 |
| ctggacgaca ccgaggtgag caacctggcc ggcaacaacg tgatcgagga cagcagggac | 420 |
| aacatcagcg tggactgcaa gcagacccag ctgtgcatcg tgggctgcgc ccccgccctg | 480 |
| ggcgagcact ggaccaaggg cgccgtgtgc aagagcaccc ccggcaacac cggcgactgc | 540 |
| ccccccctgg ccctggtgaa caccccatc gaggacggcg acatggtgga caccggcttc | 600 |
| ggcgccatgg acttcaagct gctgcaggag agcaaggccg aggtgcccct ggacatcgtg | 660 |
| cagagcacct gcaagtaccc cgactacctg aagatgagcg ccgacgccta cggcgacagc | 720 |
| atgtggttct acctgaggag ggagcagctg ttcgccaggc acttcttcaa cagggccggc | 780 |
| gtgatcggcg aggagatccc caacgacctg tacatcaagg gcagcaacgg cagggacccc | 840 |
| cccccccagca gcgtgtacgt ggccaccccc agcggcagca tgatcaccag cgaggcccag | 900 |
| ctgttcaaca agccctactg gctgcagagg gcccagggcc acaacaacgg catctgctgg | 960 |

```
ggcaaccagg tgttcgtgac cgtggtggac accaccagga gcaccaacat gaccatcaac    1020
gccgccaccg agcagctgtc caagtacgac gcccggaaga tcaaccagta cctgaggcac    1080
gtggaggagt acgagctgca gttcgtgttc cagctgtgca agatcaccct gaccgccgag    1140
gtgatggcct acctgcacaa catgaacaac ccctgctgg acgactggaa catcggcctg     1200 agccccccg tggccaccag cctggaggac aagtacaggt acatcaagag caccgccatc    1260
acctgccaga gggagcagcc ccccgccgag aagcaggacc ccctggccaa gtacaagttc    1320
tgggaggtga acctgcagga cagcttcagc gccgacctgg accagttccc cctgggcagg    1380
aagttcctga tgcagctggg ccccaggccc cccaggccca aggccagcgt gagcgccagc    1440
aagaggaggg ccgcccccac cagcagcagc agcagccccg ccaagaggaa gaagtaa      1497
```

<210> SEQ ID NO 23
<211> LENGTH: 11
<212> TYPE: PRT
<213> ORGANISM: Human papillomavirus type 56

<400> SEQUENCE: 23

Thr Glu Gln Leu Ser Lys Tyr Asp Ala Arg Lys
1               5                   10

<210> SEQ ID NO 24
<211> LENGTH: 9
<212> TYPE: PRT
<213> ORGANISM: Human papillomavirus type 53

<400> SEQUENCE: 24

Pro Ile Ser Lys Ser Gly Lys Ala Asp
1               5

<210> SEQ ID NO 25
<211> LENGTH: 37
<212> TYPE: PRT
<213> ORGANISM: Human papillomavirus type 53

<400> SEQUENCE: 25

Val Gly Val Ser Gly His Pro Leu Phe Asn Arg Leu Asp Asp Thr Glu
1               5                   10                  15

Ser Ser Ser Ile Ala Ile Gln Asp Thr Ala Pro Asp Ser Arg Asp Asn
            20                  25                  30

Val Ser Val Asp Pro
        35

<210> SEQ ID NO 26
<211> LENGTH: 25
<212> TYPE: PRT
<213> ORGANISM: Human papillomavirus type 53

<400> SEQUENCE: 26

Phe Phe Asn Arg Ala Gly Val Ile Gly Glu Glu Ile Pro Asn Asp Leu
1               5                   10                  15

Tyr Ile Lys Gly Ser Asn Gly Arg Asp
            20                  25

<210> SEQ ID NO 27
<211> LENGTH: 4
<212> TYPE: PRT
<213> ORGANISM: Human papillomavirus type 56

<400> SEQUENCE: 27

Thr Lys Asp Asn
1

<210> SEQ ID NO 28
<211> LENGTH: 498
<212> TYPE: PRT
<213> ORGANISM: Human papillomavirus type 66

<400> SEQUENCE: 28

Met Pro Ser Asp Asn Lys Val Tyr Leu Pro Pro Thr Pro Val Ser Lys
1               5                   10                  15

Val Val Ala Thr Asp Thr Tyr Val Lys Arg Thr Ser Ile Phe Tyr His
            20                  25                  30

Ala Gly Ser Ser Arg Leu Leu Ala Val Gly His Pro Tyr Tyr Ser Val
        35                  40                  45

Ser Lys Ser Gly Thr Lys Thr Asn Ile Pro Lys Val Ser Ala Tyr Gln
    50                  55                  60

Tyr Arg Val Phe Arg Val Arg Leu Pro Asp Pro Asn Lys Phe Gly Leu
65                  70                  75                  80

Pro Asp Pro Ser Phe Tyr Asn Pro Asp Gln Glu Arg Leu Val Trp Ala
                85                  90                  95

Cys Val Gly Leu Glu Val Gly Arg Gly Gln Pro Leu Gly Ala Gly Leu
            100                 105                 110

Ser Gly His Pro Leu Phe Asn Arg Leu Asp Asp Thr Glu Val Ser Asn
        115                 120                 125

Leu Ala Gly Asn Asn Val Ile Glu Asp Ser Arg Asp Asn Ile Ser Val
    130                 135                 140

Asp Cys Lys Gln Thr Gln Leu Cys Ile Val Gly Cys Ala Pro Ala Leu
145                 150                 155                 160

Gly Glu His Trp Thr Lys Gly Ala Val Cys Lys Ser Thr Pro Gly Asn
                165                 170                 175

Thr Gly Asp Cys Pro Pro Leu Ala Leu Val Asn Thr Pro Ile Glu Asp
            180                 185                 190

Gly Asp Met Val Asp Thr Gly Phe Gly Ala Met Asp Phe Lys Leu Leu
        195                 200                 205

Gln Glu Ser Lys Ala Glu Val Pro Leu Asp Ile Val Gln Ser Thr Cys
    210                 215                 220

Lys Tyr Pro Asp Tyr Leu Lys Met Ser Ala Asp Ala Tyr Gly Asp Ser
225                 230                 235                 240

Met Trp Phe Tyr Leu Arg Arg Glu Gln Leu Phe Ala Arg His Tyr Phe
                245                 250                 255

Asn Arg Ala Gly Asn Val Gly Glu Ala Ile Pro Thr Asp Leu Tyr Trp
            260                 265                 270

Lys Gly Gly Asn Gly Arg Asp Pro Pro Ser Ser Val Tyr Val Ala
        275                 280                 285

Thr Pro Ser Gly Ser Met Ile Thr Ser Glu Ala Gln Leu Phe Asn Lys
    290                 295                 300

Pro Tyr Trp Leu Gln Arg Ala Gln Gly His Asn Asn Gly Ile Cys Trp
305                 310                 315                 320

Gly Asn Gln Val Phe Val Thr Val Asp Thr Thr Arg Ser Thr Asn
                325                 330                 335

Met Thr Ile Asn Ala Ala Lys Ser Thr Leu Thr Lys Tyr Asp Ala Arg
            340                 345                 350

Glu Ile Asn Gln Tyr Leu Arg His Val Glu Glu Tyr Glu Leu Gln Phe
        355                 360                 365

```
Val Phe Gln Leu Cys Lys Ile Thr Leu Thr Ala Glu Val Met Ala Tyr
        370                 375                 380

Leu His Asn Met Asn Asn Thr Leu Leu Asp Asp Trp Asn Ile Gly Leu
385                 390                 395                 400

Ser Pro Pro Val Ala Thr Ser Leu Glu Asp Lys Tyr Arg Tyr Ile Lys
                405                 410                 415

Ser Thr Ala Ile Thr Cys Gln Arg Glu Gln Pro Ala Glu Lys Gln
        420                 425                 430

Asp Pro Leu Ala Lys Tyr Lys Phe Trp Glu Val Asn Leu Gln Asp Ser
            435                 440                 445

Phe Ser Ala Asp Leu Asp Gln Phe Pro Leu Gly Arg Lys Phe Leu Met
        450                 455                 460

Gln Leu Gly Pro Arg Pro Pro Arg Pro Lys Ala Ser Val Ser Ala Ser
465                 470                 475                 480

Lys Arg Arg Ala Ala Pro Thr Ser Ser Ser Ser Pro Ala Lys Arg
                485                 490                 495

Lys Lys

<210> SEQ ID NO 29
<211> LENGTH: 1497
<212> TYPE: DNA
<213> ORGANISM: Human papillomavirus type 66

<400> SEQUENCE: 29
atgcccagcg acaacaaggt gtacctgccc cccaccccg tgagcaaggt ggtggccacc      60
gacacctacg tgaagaggac cagcatcttc taccacgccg cagcagcag gctgctggcc    120 gtgggccacc cctactacag cgtgagcaag agcggcacca agaccaacat ccccaaggtg    180
agcgcctacc agtacagggt gttcagggtg aggctccccg accccaacaa gttcggcctg    240
cccgacccca gcttctacaa ccccgaccag gagaggctgg tgtgggcctg cgtgggcctg    300
gaggtgggca ggggccagcc cctgggcgcc ggcctgagcg gccaccccct gttcaacagg    360
ctggacgaca ccgaggtgag caacctggcc ggcaacaacg tgatcgagga cagcagggac    420
aacatcagcg tggactgcaa gcagacccag ctgtgcatcg tgggctgcgc ccccgccctg    480
ggcgagcact ggaccaaggg cgccgtgtgc aagagcaccc ccggcaacac cggcgactgc    540 cccccctgg ccctggtgaa cacccccatc gaggacggcg acatggtgga caccggcttc    600
ggcgccatgg acttcaagct gctgcaggag agcaaggccg aggtgccccT ggacatcgtg    660
cagagcacct gcaagtaccc cgactacctg aagatgagcg ccgacgccta cggcgacagc    720
atgtggttct acctgaggag ggagcagctg ttcgccaggc actacttcaa cagggccggc    780
aacgtgggcg aggccatccc caccgacctg tactggaagg cggcaacgg cagggacccc    840 cccccagca gcgtgtacgt ggccacccc agcggcagca tgatcaccag cgaggcccag    900
ctgttcaaca gccctactg gctgcagagg gccagggcc acaacaacgg catctgctgg    960
ggcaaccagg tgttcgtgac cgtggtggac accaccagga gcaccaacat gaccatcaac   1020
gccgccaaga gcaccctgac caagtacgac gccagggaga tcaaccagta cctgaggcac   1080
gtggaggagt acgagctgca gttcgtgttc cagctgtgca agatcaccct gaccgccgag   1140
gtgatggcct acctgcacaa catgaacaac accctgctgg acgactggaa catcggcctg   1200
agcccccccg tggccaccag cctggaggac aagtacaggt acatcaagag caccgccatc   1260
acctgccaga gggagcagcc ccccgccgag aagcaggacc ccctggccaa gtacaagttc   1320
```

-continued

```
tgggaggtga acctgcagga cagcttcagc gccgacctgg accagttccc cctgggcagg    1380
aagttcctga tgcagctggg ccccaggccc cccaggccca aggccagcgt gagcgccagc    1440
aagaggaggg ccgccccac cagcagcagc agcagcccg ccaagaggaa gaagtaa        1497
```

<210> SEQ ID NO 30
<211> LENGTH: 3
<212> TYPE: PRT
<213> ORGANISM: Human papillomavirus type 56

<400> SEQUENCE: 30

Gln Val Thr
1

<210> SEQ ID NO 31
<211> LENGTH: 495
<212> TYPE: PRT
<213> ORGANISM: Human papillomavirus type 53

<400> SEQUENCE: 31

```
Met Pro Ser Asp Ser Lys Val Tyr Leu Pro Pro Thr Pro Val Ser Lys
1               5                   10                  15

Val Ile Thr Thr Asp Ala Tyr Val Lys Arg Thr Thr Ile Phe Tyr His
            20                  25                  30

Ala Gly Ser Ser Arg Leu Leu Thr Val Gly His Pro Tyr Tyr Pro Ile
        35                  40                  45

Ser Lys Ser Gly Lys Ala Asp Ile Pro Lys Val Ser Ala Phe Gln Tyr
    50                  55                  60

Arg Val Phe Arg Val Arg Leu Pro Asp Pro Asn Lys Phe Gly Leu Pro
65                  70                  75                  80

Asp Thr Asn Ile Phe Asn Pro Asp Gln Glu Arg Leu Val Trp Ala Cys
                85                  90                  95

Val Gly Leu Glu Ile Gly Arg Gly Gln Pro Leu Gly Val Gly Val Ser
            100                 105                 110

Gly His Pro Leu Phe Asn Arg Leu Asp Asp Thr Glu Ser Ser Ser Ile
        115                 120                 125

Ala Ile Gln Asp Thr Ala Pro Asp Ser Arg Asp Asn Val Ser Val Asp
    130                 135                 140

Pro Lys Gln Thr Gln Leu Cys Ile Ile Gly Cys Ala Pro Ala Ile Gly
145                 150                 155                 160

Glu His Trp Thr Lys Gly Thr Ala Cys Arg Ser Thr Pro Thr Thr Ala
                165                 170                 175

Gly Asp Cys Pro Pro Leu Glu Leu Ile Asn Ser Pro Ile Glu Asp Gly
            180                 185                 190

Asp Met Val Asp Thr Gly Phe Gly Ala Leu Asn Phe Lys Ala Leu Gln
        195                 200                 205

Glu Ser Lys Ser Asp Val Pro Leu Asp Ile Val Gln Ser Thr Cys Lys
    210                 215                 220

Tyr Pro Asp Tyr Leu Lys Met Ser Ala Asp Ala Tyr Gly Asp Ser Met
225                 230                 235                 240

Trp Phe Tyr Leu Arg Arg Glu Gln Leu Phe Thr Arg His Phe Phe Asn
                245                 250                 255

Arg Ala Gly Val Ile Gly Glu Glu Ile Pro Asn Asp Leu Tyr Ile Lys
            260                 265                 270

Gly Ser Asn Gly Arg Asp Pro Pro Ser Ser Val Tyr Val Ala Thr
        275                 280                 285
```

| Pro | Ser | Gly | Ser | Met | Ile | Thr | Ser | Glu | Ala | Gln | Leu | Phe | Asn | Lys | Pro |
| | 290 | | | | | 295 | | | | 300 | | | | | |

| Tyr | Trp | Leu | Gln | Arg | Ala | Gln | Gly | His | Asn | Asn | Gly | Ile | Cys | Trp | Asn |
| 305 | | | | | 310 | | | | | 315 | | | | | 320 |

| Asn | Gln | Leu | Phe | Val | Thr | Val | Val | Asp | Thr | Thr | Arg | Asn | Thr | Asn | Met |
| | | | | 325 | | | | | 330 | | | | | 335 | |

| Thr | Leu | Ser | Ala | Thr | Thr | Gln | Ser | Met | Ser | Thr | Tyr | Asn | Ser | Lys | Gln |
| | | | 340 | | | | | 345 | | | | | 350 | | |

| Ile | Lys | Gln | Tyr | Val | Arg | His | Ala | Glu | Glu | Tyr | Glu | Leu | Gln | Phe | Val |
| | | | 355 | | | | 360 | | | | | 365 | | | |

| Phe | Gln | Leu | Cys | Lys | Ile | Ser | Leu | Ser | Ala | Glu | Val | Met | Ala | Tyr | Leu |
| | 370 | | | | | 375 | | | | 380 | | | | | |

| His | Thr | Met | Asn | Ser | Thr | Leu | Leu | Glu | Asp | Trp | Asn | Ile | Gly | Leu | Ser |
| 385 | | | | | 390 | | | | | 395 | | | | | 400 |

| Pro | Pro | Val | Ala | Thr | Ser | Leu | Glu | Asp | Lys | Tyr | Arg | Tyr | Val | Lys | Ser |
| | | | | 405 | | | | | 410 | | | | | 415 | |

| Ala | Ala | Ile | Thr | Cys | Gln | Lys | Asp | Gln | Pro | Pro | Glu | Lys | Gln | Asp |
| | | | 420 | | | | | 425 | | | | | 430 | |

| Pro | Leu | Ser | Lys | Tyr | Lys | Phe | Trp | Glu | Val | Asn | Leu | Gln | Asn | Ser | Phe |
| | | | 435 | | | | | 440 | | | | | 445 | | |

| Ser | Ala | Asp | Leu | Asp | Gln | Phe | Pro | Leu | Gly | Arg | Lys | Phe | Leu | Met | Gln |
| | 450 | | | | | 455 | | | | 460 | | | | | |

| Val | Gly | Val | Arg | Thr | Lys | Pro | Pro | Val | Ser | Ser | Lys | Lys | Arg | Ser | Ala |
| 465 | | | | | 470 | | | | | 475 | | | | | 480 |

| Ser | Thr | Thr | Ser | Thr | Ser | Ala | Pro | Ser | Ser | Lys | Arg | Lys | Arg | Lys |
| | | | | 485 | | | | | 490 | | | | | 495 |

<210> SEQ ID NO 32
<211> LENGTH: 1488
<212> TYPE: DNA
<213> ORGANISM: Human papillomavirus type 53

<400> SEQUENCE: 32

| atgcccagcg | acagcaaggt | gtacctgccc | cccacccccg | tgagcaaggt | gatcaccacc | 60 |
| gacgcctacg | tgaagaggac | caccatcttc | taccacgccg | gcagcagcag | gctgctgacc | 120 |
| gtgggccacc | cctactaccc | catcagcaag | agcggcaagg | ccgacatccc | caaggtgagc | 180 |
| gccttccagt | acagggtgtt | cagggtgagg | ctgcccgacc | ccaacaagtt | cggcctgccc | 240 |
| gacaccaaca | tcttcaaccc | cgaccaggag | aggctggtgt | gggcctgcgt | gggcctggag | 300 |
| atcggcaggg | gccagccccc | tgggcgtggg | gtgagcggcc | acccccctgtt | caacaggctg | 360 |
| gacgacaccg | agagcagcag | catcgccatc | caggacaccg | ccccgacag | cagggacaac | 420 |
| gtgagcgtgg | accccaagca | gacccagctg | tgcatcatcg | gctgcgcccc | cgccatcggc | 480 |
| gagcactgga | ccaagggcac | cgcctgcagg | agcaccccca | ccaccgccgg | cgactgcccc | 540 |
| cccctggagc | tgatcaacag | ccccatcgag | gacggcgaca | tggtggacac | cggcttcggc | 600 |
| gccctgaact | tcaaggccct | gcaggagagc | aagagcgacg | tgcccctgga | catcgtgcag | 660 |
| agcacctgca | gtaccccga | ctacctgaag | atgagcgccg | acgcctacgg | cgacagcatg | 720 |
| tggttctacc | tgaggaggga | gcagctgttc | accaggcact | tcttcaacag | ggccggcgtg | 780 |
| atcggcgagg | agatccccaa | cgacctgtac | atcaagggca | gcaacggcag | gacccccccc | 840 |
| cccagcagct | gtacgtggc | cacccccagc | ggcagcatga | tcaccagcga | ggcccagctg | 900 |
| ttcaacaagc | cctactggct | gcagagggcc | cagggccaca | caacggcat | ctgctggaac | 960 |

```
aaccagctgt tcgtgaccgt ggtggacacc accaggaaca ccaacatgac cctgagcgcc    1020
accacccaga gcatgagcac ctacaacagc aagcagatca agcagtacgt gaggcacgcc    1080
gaggagtacg agctgcagtt cgtgttccag ctgtgcaaga tcagcctgag cgccgaggtg    1140
atggcctacc tgcacaccat gaacagcacc ctgctggagg actggaacat cggcctgagc    1200 cccccgtgg ccaccagcct ggaggacaag tacaggtacg tgaagagcgc cgccatcacc    1260
tgccagaagg accagccccc ccccgagaag caggacccc tgagcaagta caagttctgg    1320
gaggtgaacc tgcagaacag cttcagcgcc gacctggacc agttcccct gggcaggaag    1380 ttcctgatgc aggtgggcgt gaggaccaag cccccgtga gcagcaagaa gaggagcgcc    1440
agcaccacca gcaccagcgc ccccagcagc aagaggaaga ggaagtaa                1488
```

<210> SEQ ID NO 33
<211> LENGTH: 21
<212> TYPE: PRT
<213> ORGANISM: Human papillomavirus type 53

<400> SEQUENCE: 33

Ser Ser Asn Leu Ala Asn Asn Asn Val Ile Glu Asp Ser Arg Asp Asn
1               5                   10                  15

Ile Ser Val Asp Gly
            20

<210> SEQ ID NO 34
<211> LENGTH: 19
<212> TYPE: PRT
<213> ORGANISM: Human papillomavirus type 53

<400> SEQUENCE: 34

Lys Val Gly Glu Thr Ile Pro Ala Glu Leu Tyr Leu Lys Gly Ser Asn
1               5                   10                  15

Gly Arg Glu

<210> SEQ ID NO 35
<211> LENGTH: 42
<212> TYPE: DNA
<213> ORGANISM: Artificial Sequence
<220> FEATURE:
<223> OTHER INFORMATION: Synthesized Sequence

<400> SEQUENCE: 35
agcgtgacca aggacaacac caagaccaac atccccaagg tg                         42

<210> SEQ ID NO 36
<211> LENGTH: 42
<212> TYPE: DNA
<213> ORGANISM: Artificial Sequence
<220> FEATURE:
<223> OTHER INFORMATION: Synthesized Sequence

<400> SEQUENCE: 36
cttggtgttg tccttggtca cgctgtagta ggggtggccc ac                         42

<210> SEQ ID NO 37
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 37
cacctccagg cccacgcagg c                                              21

<210> SEQ ID NO 38
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 38
aagcagaccc agctgtgcat c                                              21

<210> SEQ ID NO 39
<211> LENGTH: 42
<212> TYPE: DNA
<213> ORGANISM: Artificial Sequence
<220> FEATURE:
<223> OTHER INFORMATION: Synthesized Sequence

<400> SEQUENCE: 39
agcacccagg tcaccaccgg cgactgcccc cctctggccc tg                       42

<210> SEQ ID NO 40
<211> LENGTH: 42
<212> TYPE: DNA
<213> ORGANISM: Artificial Sequence
<220> FEATURE:
<223> OTHER INFORMATION: Synthesized Sequence

<400> SEQUENCE: 40
gccggtggtg acctgggtgc tcttgcacac ggcgcccttg gt                       42

<210> SEQ ID NO 41
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 41
gtgcctggcg aacagctgct c                                              21

<210> SEQ ID NO 42
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 42
gccaccccca gcggcagcat g                                              21

<210> SEQ ID NO 43
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 43
gccaccccca gcggcagcat g                                              21

<210> SEQ ID NO 44
<211> LENGTH: 21
<212> TYPE: DNA
<213> ORGANISM: Artificial Sequence -continued

```
<220> FEATURE:
<223> OTHER INFORMATION: Synthesized Sequence

<400> SEQUENCE: 44
atcaaccagt acctgaggca c                                              21

<210> SEQ ID NO 45
<211> LENGTH: 42
<212> TYPE: DNA
<213> ORGANISM: Artificial Sequence
<220> FEATURE:
<223> OTHER INFORMATION: Synthesized Sequence

<400> SEQUENCE: 45
gcctgcgtgg gcctggaggt gggcagaggc cagcctctgg ga                       42

<210> SEQ ID NO 46
<211> LENGTH: 42
<212> TYPE: DNA
<213> ORGANISM: Artificial Sequence
<220> FEATURE:
<223> OTHER INFORMATION: Synthesized Sequence

<400> SEQUENCE: 46
gatgcacagc tgggtctgct tgccgtccac gctgatgttg tc                       42

<210> SEQ ID NO 47
<211> LENGTH: 42
<212> TYPE: DNA
<213> ORGANISM: Artificial Sequence
<220> FEATURE:
<223> OTHER INFORMATION: Synthesized Sequence

<400> SEQUENCE: 47
gagcagctgt tcgccaggca ctacttcaac agagccggca aa                       42

<210> SEQ ID NO 48
<211> LENGTH: 42
<212> TYPE: DNA
<213> ORGANISM: Artificial Sequence
<220> FEATURE:
<223> OTHER INFORMATION: Synthesized Sequence

<400> SEQUENCE: 48
catgctgccg ctgggggtgg ccacgtacac gctgctggga gg                       42

<210> SEQ ID NO 49
<211> LENGTH: 42
<212> TYPE: DNA
<213> ORGANISM: Artificial Sequence
<220> FEATURE:
<223> OTHER INFORMATION: Synthesized Sequence

<400> SEQUENCE: 49
aacatgacca tcaacgccgc caccgagcag ctgtccaagt ac                       42

<210> SEQ ID NO 50
<211> LENGTH: 42
<212> TYPE: DNA
<213> ORGANISM: Artificial Sequence
<220> FEATURE:
<223> OTHER INFORMATION: Synthesized Sequence

<400> SEQUENCE: 50
gtgcctcagg tactggttga tcttccgggc gtcgtacttg ga                       42
```

<210> SEQ ID NO 51
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 51 gtagggtgg cccacggcca g                                              21

<210> SEQ ID NO 52
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 52
gcctaccagt acagggtgtt c                                              21

<210> SEQ ID NO 53
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 53
cacctccagg cccacgcagg c                                              21

<210> SEQ ID NO 54
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 54
aagcagaccc agctgtgcat c                                              21

<210> SEQ ID NO 55
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 55
gtgcctggcg aacagctgct c                                              21

<210> SEQ ID NO 56
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 56
gccaccccca gcggcagcat g                                              21

<210> SEQ ID NO 57
<211> LENGTH: 42
<212> TYPE: DNA
<213> ORGANISM: Artificial Sequence
<220> FEATURE:
<223> OTHER INFORMATION: Synthesized Sequence

<400> SEQUENCE: 57
ctggccgtgg gccaccccta ctaccccatc agcaagagcg gc     42

<210> SEQ ID NO 58
<211> LENGTH: 42
<212> TYPE: DNA
<213> ORGANISM: Artificial Sequence
<220> FEATURE:
<223> OTHER INFORMATION: Synthesized Sequence

<400> SEQUENCE: 58
gaacaccctg tactggtagg cgctcacctt ggggatgtcg gc     42

<210> SEQ ID NO 59
<211> LENGTH: 42
<212> TYPE: DNA
<213> ORGANISM: Artificial Sequence
<220> FEATURE:
<223> OTHER INFORMATION: Synthesized Sequence

<400> SEQUENCE: 59
gcctgcgtgg gcctggaggt gggcaggggc cagcccctgg gc     42

<210> SEQ ID NO 60
<211> LENGTH: 42
<212> TYPE: DNA
<213> ORGANISM: Artificial Sequence
<220> FEATURE:
<223> OTHER INFORMATION: Synthesized Sequence

<400> SEQUENCE: 60
gatgcacagc tgggtctgct tggggtccac gctcacgttg tc     42

<210> SEQ ID NO 61
<211> LENGTH: 42
<212> TYPE: DNA
<213> ORGANISM: Artificial Sequence
<220> FEATURE:
<223> OTHER INFORMATION: Synthesized Sequence

<400> SEQUENCE: 61
gagcagctgt tcgccaggca cttcttcaac agggccggcg tg     42

<210> SEQ ID NO 62
<211> LENGTH: 42
<212> TYPE: DNA
<213> ORGANISM: Artificial Sequence
<220> FEATURE:
<223> OTHER INFORMATION: Synthesized Sequence

<400> SEQUENCE: 62
catgctgccg ctgggggtgg ccacgtacac gctgctgggg gg     42

<210> SEQ ID NO 63
<211> LENGTH: 492
<212> TYPE: PRT
<213> ORGANISM: Artificial Sequence
<220> FEATURE:
<223> OTHER INFORMATION: Synthesized Sequence

<400> SEQUENCE: 63

Met Ala Met Trp Arg Pro Ser Asp Asn Lys Val Tyr Leu Pro Pro Thr
1               5                   10                  15

Pro Val Ser Lys Val Val Ala Thr Asp Thr Tyr Val Lys Arg Thr Ser

-continued

```
                20                  25                  30
Ile Phe Tyr His Ala Gly Ser Ser Arg Leu Leu Ala Val Gly His Pro
             35                  40                  45
Tyr Tyr Ser Val Ser Lys Ser Gly Thr Lys Thr Asn Ile Pro Lys Val
         50                  55                  60
Ser Ala Tyr Gln Tyr Arg Val Phe Arg Val Arg Leu Pro Asp Pro Asn
 65                  70                  75                  80
Lys Phe Gly Leu Pro Asp Pro Ser Phe Tyr Asn Pro Asp Gln Glu Arg
                 85                  90                  95
Leu Val Trp Ala Cys Val Gly Leu Glu Val Gly Arg Gly Gln Pro Leu
            100                 105                 110
Gly Val Gly Val Ser Gly His Pro Leu Phe Asn Arg Leu Asp Asp Thr
        115                 120                 125
Glu Ser Ser Ser Ile Ala Ile Gln Asp Thr Ala Pro Asp Ser Arg Asp
    130                 135                 140
Asn Val Ser Val Asp Pro Lys Gln Thr Gln Leu Cys Ile Val Gly Cys
145                 150                 155                 160
Ala Pro Ala Leu Gly Glu His Trp Thr Lys Gly Thr Ala Cys Arg Ser
                165                 170                 175
Thr Pro Thr Thr Ala Gly Asp Cys Pro Pro Leu Ala Leu Val Asn Thr
            180                 185                 190
Pro Ile Glu Asp Gly Asp Met Val Asp Thr Gly Phe Gly Ala Met Asp
        195                 200                 205
Phe Lys Leu Leu Gln Glu Ser Lys Ala Glu Val Pro Leu Asp Ile Val
    210                 215                 220
Gln Ser Thr Cys Lys Tyr Pro Asp Tyr Leu Lys Met Ser Ala Asp Ala
225                 230                 235                 240
Tyr Gly Asp Ser Met Trp Phe Tyr Leu Arg Arg Glu Gln Leu Phe Ala
                245                 250                 255
Arg His Tyr Phe Asn Arg Ala Gly Asn Val Gly Glu Ala Ile Pro Thr
            260                 265                 270
Asp Leu Tyr Trp Lys Gly Gly Asn Gly Arg Asp Pro Pro Ser Ser
        275                 280                 285
Val Tyr Val Ala Thr Pro Ser Gly Ser Met Ile Thr Ser Glu Ala Gln
    290                 295                 300
Leu Phe Asn Lys Pro Tyr Trp Leu Gln Arg Ala Gln Gly His Asn Asn
305                 310                 315                 320
Gly Ile Cys Trp Gly Asn Gln Val Phe Val Thr Val Val Asp Thr Thr
                325                 330                 335
Arg Ser Thr Asn Met Thr Ile Asn Ala Ala Thr Ile Asn Gln Tyr Leu
            340                 345                 350
Arg His Val Glu Glu Tyr Glu Leu Gln Phe Val Phe Gln Leu Cys Lys
        355                 360                 365
Ile Thr Leu Thr Ala Glu Val Met Ala Tyr Leu His Asn Met Asn Asn
    370                 375                 380
Thr Leu Leu Asp Asp Trp Asn Ile Gly Leu Ser Pro Pro Val Ala Thr
385                 390                 395                 400
Ser Leu Glu Asp Lys Tyr Arg Tyr Ile Lys Ser Thr Ala Ile Thr Cys
                405                 410                 415
Gln Arg Glu Gln Pro Pro Ala Glu Lys Gln Asp Pro Leu Ala Lys Tyr
            420                 425                 430
Lys Phe Trp Glu Val Asn Leu Gln Asp Ser Phe Ser Ala Asp Leu Asp
        435                 440                 445
```

```
Gln Phe Pro Leu Gly Arg Lys Phe Leu Met Gln Leu Gly Pro Arg Pro
    450                 455                 460

Pro Arg Pro Lys Ala Ser Val Ser Ala Ser Lys Arg Arg Ala Ala Pro
465                 470                 475                 480

Thr Ser Ser Ser Ser Ser Pro Ala Lys Arg Lys Lys
                485                 490
```

<210> SEQ ID NO 64
<211> LENGTH: 1509
<212> TYPE: DNA
<213> ORGANISM: Artificial Sequence
<220> FEATURE:
<223> OTHER INFORMATION: Synthesized Sequence

<400> SEQUENCE: 64

```
atggccatgt ggaggcccag cgacaacaag gtgtacctgc cccccacccc cgtgagcaag      60
gtggtggcca ccgacaccta cgtgaagagg accagcatct tctaccacgc cggcagcagc     120
aggctgctgg ccgtgggcca ccctactac agcgtgagca agagcggcac caagaccaac      180
atccccaagg tgagcgccta ccagtacagg gtgttcaggg tgaggctccc cgaccccaac     240
aagttcggcc tgcccgaccc cagcttctac aaccccgacc aggagaggct ggtgtgggcc     300
tgcgtgggcc tggaggtggg caggggccag cccctgggcg tgggcgtgag cggccacccc     360
ctgttcaaca ggctggacga caccgagagc agcagcatcg ccatccagga caccgccccc     420
gacagcaggg acaacgtgag cgtggacccc aagcagaccc agctgtgcat cgtgggctgc     480
gcccccgccc tgggcgagca ctggaccaag ggcaccgcct gcaggagcac ccccaccacc     540
gccggcgact gcccccccct ggccctggtg aacaccccca tcgaggacgg cgacatggtg     600
gacaccggct tcgcgccat ggacttcaag ctgctgcagg agagcaaggc cgaggtgccc     660
ctggacatcg tgcagagcac ctgcaagtac cccgactacc tgaagatgag cgccgacgcc     720
tacgccgaca catgtggtt ctacctgagg agggagcagc tgttcgccag cactacttc      780 aacagggccg gcaacgtggg cgaggccatc cccaccgacc tgtactggaa gggcggcaac     840
ggcagggacc cccccccag cagcgtgtac gtggccaccc ccagcggcag catgatcacc     900
agcgaggccc agctgttcaa caagccctac tggctgcaga gggcccaggg ccacaacaac     960
ggcatctgct ggggcaacca ggtgttcgtg accgtggtgg acaccaccag gagcaccaac    1020
atgaccatca acgccgccac cgagcagctg tccaagtacg acgcccggaa gatcaaccag    1080
tacctgaggc acgtggagga gtacgagctg cagttcgtgt tccagctgtg caagatcacc    1140
ctgaccgccg aggtgatggc ctacctgcac aacatgaaca cacccctgct ggacgactgg    1200
aacatcggcc tgagcccccc cgtggccacc agcctggagg acaagtacag gtacatcaag    1260
agcaccgcca tcacctgcca gagggagcag cccccgccg agaagcagga ccccctggcc    1320
aagtacaagt tctgggaggt gaacctgcag gacagcttca gcgccgacct ggaccagttc    1380
cccctgggca ggaagttcct gatgcagctg ggccccaggc cccccaggcc caaggccagc    1440
gtgagcgcca gcaagaggag ggccgccccc accagcagca gcagcagccc cgccaagagg    1500
aagaagtaa                                                            1509
```

<210> SEQ ID NO 65
<211> LENGTH: 10
<212> TYPE: PRT
<213> ORGANISM: Human papillomavirus type 53

```
<400> SEQUENCE: 65

Thr Ala Cys Arg Ser Thr Pro Thr Thr Ala
1               5                   10
```

MUTANT OF L1 PROTEIN OF HUMAN PAPILLOMAVIRUS TYPE 66

The present application is a National Stage application of International Application No. PCT/CN2019/089940, filed Jun. 4, 2019, which is based on and claims the benefit of priority from Chinese application No. 201810563504.2, filed on Jun. 4, 2018, the disclosures of both of which are incorporated herein by reference in its entirety.

SEQUENCE LISTING

The instant application contains a Sequence Listing which has been submitted electronically in ASCII format and is hereby incorporated by reference in its entirety. Said ASCII copy, created Dec. 1, 2020, is named IEC180089_seq1_EN and is 98,304 bytes in size.

TECHNICAL FIELD

The invention relates to the field of molecular virology and immunology. In particular, the invention relates to a mutated HPV66 L1 protein (or a variant thereof), a sequence encoding the same, a method for preparing the same, and a virus-like particle comprising the same, wherein the protein (or a variant thereof) and the virus-like particle can induce the generation of neutralizing antibodies against at least two HPV types (e.g. HPV66 and HPV56, or HPV66, HPV56 and HPV53), and therefore can be used to prevent infection by said at least two HPV types, and a disease caused by said infection, such as cervical cancer and condyloma acuminatum. The invention further relates to the use of the protein and the virus-like particle in the manufacture of a pharmaceutical composition or a vaccine for preventing infection by said at least two HPV types, and a disease caused by said infection, such as cervical cancer and condyloma acuminatum.

BACKGROUND ART

Human Papillomavirus (HPV) mainly causes warts in skin and mucosa. HPV types are divided into high-risk types and low-risk types depending on their association with tumorigenesis. Among them, infection by high-risk HPV types has been demonstrated to be the leading cause of genital cancer including cervical cancer in women; and low-risk HPV types mainly cause condyloma acuminatum. The most effective way to prevent and control HPV infection is to vaccinate HPV vaccines, particularly vaccines against high-risk HPV types causing cervical cancer.

Major capsid protein L1 of HPV has the characteristic of self-assembling into hollow Virus-Like Particle (VLP). HPV VLP has a symmetrical icosahedral structure composed of 72 pentamers of major capsid protein L1 (Doorbar, J. and P. H. Gallimore. 1987. J Virol, 61(9): 2793-9). HPV VLP is highly similar to natural HPV in terms of structure, retains most of the neutralizing epitopes of natural virus, and can induce the generation of high-titer neutralizing antibodies (Kirnbauer, R., F. Booy, et al. 1992 Proc Natl Acad Sci USA 89(24): 12180-4).

However, the existing studies show that HPV VLPs mainly induce the generation of neutralizing antibodies against the same HPV type, produce the protective immunity against the same HPV type, and only have low cross-protective effect among a few highly homologous HPV types (Sara L. Bissett, Giada Mattiuzzo, et al. 2014 Vaccine. 32:6548-6555). Therefore, the existing HPV vaccines have a very limited protection range. In general, VLP of one HPV type can only be used to prevent infection by the same HPV type. In this case, if it needs to broaden the protection range of HPV vaccines, the only way is to add VLPs of more HPV types in vaccines. Currently, the commercially available HPV vaccines, including Gardasil® from Merck (which is a quadrivalent vaccine against HPV16, 18, 6 and 11), Cervarix® from GSK (which is a bivalent vaccine against HPV16 and 18), and Gardasil®9 from Merck (which is a 9-valent vaccine against HPV6, 11, 16, 18, 31, 33, 45, 52 and 58), are prepared by combining VLPs of multiple HPV types. However, such a solution would greatly increase the production cost of HPV vaccines, and might cause safety problem due to an increase in immunizing dose.

Therefore, it is urgent in the art to develop HPV virus-like particles capable of inducing the generation of protective neutralizing antibodies against multiple HPV types, so as to prevent infection by multiple HPV types, and a disease caused by the infection, such as cervical cancer and condyloma acuminatum, more economically and effectively.

Contents of Invention

The invention is at least partially based on the inventors' surprising discovery: after substitution of a specific segment of L1 protein of Human Papillomavirus (HPV) Type 66 with the corresponding segment of L1 protein of a second HPV type (such as HPV56), the mutated HPV66 L1 protein thus obtained can induce the generation of high-titer neutralizing antibodies against HPV66 and the second HPV type (such as HPV56) in organisms, and its protection effect is comparable to that of a mixture of HPV66 VLP and VLP of the second HPV type, its protection effect against HPV66 is comparable to that of HPV66 VLP alone, and its protection effect against the second HPV type (such as HPV56) is comparable to that of the VLP of the second HPV type alone.

In addition, based on the substitution above, other one or two specific segments of HPV66 L1 protein can be further substituted with the corresponding segment of L1 protein of a third HPV type (such as HPV53), and the mutated HPV66 L1 protein having double substitutions thus obtained can induce the generation of high-titer neutralizing antibodies against HPV66, the second HPV type (such as HPV56) and the third HPV type (such as HPV53); and its protection effect is comparable to that of a mixture of HPV66 VLP, VLP of the second HPV type and VLP of the third HPV type, its protection effect against HPV66 is comparable to that of HPV66 VLP alone, its protection effect against the second HPV type (such as HPV56) is comparable to that of the VLP of the second HPV type alone, and its protection effect against the third HPV type (such as HPV53) is comparable to that of the VLP of the third HPV type alone.

Therefore, in an aspect, the invention provides a mutated HPV66 L1 protein or a variant thereof, wherein as compared with a wild type HPV66 L1 protein, the mutated HPV66 L1 protein has the following mutations:

(1) N-terminal truncation of 1-20 amino acids, for example, 1-20 amino acids, e.g. 1-5, 3-8, 5-10, 9-13, 10-15, 12-18 or 15-20 amino acids; and (2) (a) substitution of amino acid residues at positions 265-283 of the wild type HPV66 L1 protein with amino acid residues at the corresponding positions of a L1 protein of a second type of wild-type HPV; or (b) substitution of amino acid residues at positions 347-357 of the wild type HPV66 L1 protein with amino acid residues at the corresponding positions of a L1 protein of a second type of wild-type HPV;

and, the variant differs from the mutated HPV66 L1 protein only by substitution (preferably conservative substitution), addition or deletion of one or more (e.g. 1, 2, 3, 4, 5, 6, 7, 8, 9, 10 or 11) amino acids, and retains the function of the mutated HPV66 L1 protein, i.e. capability of inducing generation of neutralizing antibodies against at least two HPV types (e.g. HPV66 and HPV56, or HPV66, HPV56 and HPV53).

In some preferred embodiments, the mutated HPV66 L1 protein has the mutation as defined in (2) (b), and optionally, further has the following mutation:

(3) substitution of amino acid residues at positions 51-60 of the wild type HPV66 L1 protein with amino acid residues at the corresponding positions of a L1 protein of a third type of wild-type HPV, or (4) substitution of amino acid residues at positions 114-150 of the wild type HPV66 L1 protein with amino acid residues at the corresponding positions of a L1 protein of a third type of wild-type HPV, or (5) substitution of amino acid residues at positions 259-283 of the wild type HPV66 L1 protein with amino acid residues at the corresponding positions of a L1 protein of a third type of wild-type HPV.

In some preferred embodiments, the mutated HPV66 L1 protein has the mutations as defined in (2) (b) and (4), and optionally, further has the following mutation:

(6) substitution of amino acid residues at positions 172-181 of the wild type HPV66 L1 protein with amino acid residues at the corresponding positions of a L1 protein of a third type of wild-type HPV.

In some preferred embodiments, the mutated HPV66 L1 protein has 3, 5, 8, 10, 12, 15 or 18 amino acids truncated at N-terminal, as compared with the wild type HPV66 L1 protein.

In some preferred embodiments, the mutated HPV66 L1 protein has 5 amino acids truncated at N-terminal, as compared with the wild type HPV66 L1 protein.

In some preferred embodiments, the second type of wild-type HPV is HPV56. In some preferred embodiments, the amino acid residues at the corresponding positions as described in (2) (a) are amino acid residues at positions 265-283 of a wild type HPV56 L1 protein. In some preferred embodiments, the amino acid residues at the corresponding positions as described in (2) (b) are amino acid residues at positions 347-357 of a wild type HPV56 L1 protein.

In some preferred embodiments, the third type of wild-type HPV is HPV53. In some preferred embodiments, the amino acid residues at the corresponding positions as described in (3) are amino acid residues at positions 51-59 of a wild type HPV53 L1 protein. In some preferred embodiments, the amino acid residues at the corresponding positions as described in (4) are amino acid residues at positions 113-149 of a wild type HPV53 L1 protein. In some preferred embodiments, the amino acid residues at the corresponding positions as described in (5) are amino acid residues at positions 258-282 of a wild type HPV53 L1 protein. In some preferred embodiments, the amino acid residues at the corresponding positions as described in (6) are amino acid residues at positions 171-180 of a wild type HPV53 L1 protein.

In some preferred embodiments, the wild type HPV66 L1 protein has an amino acid sequence as set forth in SEQ ID NO: 1 or 28.

In some preferred embodiments, the wild type HPV56 L1 protein has an amino acid sequence as set forth in SEQ ID NO: 2.

In some preferred embodiments, the wild type HPV53 L1 protein has an amino acid sequence as set forth in SEQ ID NO: 3 or 31.

In some preferred embodiments, the amino acid residues at positions 347-357 of the wild type HPV56 L1 protein have a sequence as set forth in SEQ ID NO: 23.

In some preferred embodiments, the amino acid residues at positions 51-59 of the wild type HPV53 L1 protein have a sequence as set forth in SEQ ID NO: 24.

In some preferred embodiments, the amino acid residues at positions 113-149 of the wild type HPV53 L1 protein have a sequence as set forth in SEQ ID NO: 25.

In some preferred embodiments, the amino acid residues at positions 171-180 of the wild type HPV53 L1 protein have a sequence as set forth in SEQ ID NO: 65.

In some preferred embodiments, the amino acid residues at positions 258-282 of the wild type HPV53 L1 protein have a sequence as set forth in SEQ ID NO: 26.

In some preferred embodiments, the mutated HPV66 L1 protein has an amino acid sequence selected from the group consisting of: SEQ ID NO: 7, 8, 9, 10, 11 and 63.

In another aspect, the invention provides an isolated nucleic acid, encoding the mutated HPV66 L1 protein or a variant thereof as described above. In another aspect, the invention provides a vector comprising the isolated nucleic acid. In some preferred embodiments, the isolated nucleic acid according to the invention has a nucleotide sequence selected from the group consisting of: SEQ ID NO: 18, 19, 20, 21, 22 and 64.

Vectors useful for insertion of a polynucleotide of interest are well known in the art, including, but not limited to cloning vectors and expression vectors. In one embodiment, the vectors are, for example, plasmids, cosmids, phages, etc.

In another aspect, the invention further relates to a host cell comprising the isolated nucleic acid or the vector. The host cell includes, but is not limited to prokaryotic cells such as *E. coli* cells, and eukaryotic cells such as yeast cells, insect cells, plant cells and animal cells (such as mammalian cells, for example, mouse cells, human cells, etc.). The host cell according to the invention may also be a cell line, such as 293T cell.

In another aspect, the invention relates to a HPV virus-like particle, comprising or consisting of the mutated HPV66 L1 protein or a variant thereof according to the invention.

In some preferred embodiments, the HPV virus-like particle according to the invention comprises the mutated HPV66 L1 protein, which has N-terminal truncation of 1-20 amino acids, for example, 1-20 amino acids, e.g. 1-5, 3-8, 5-10, 9-13, 10-15, 12-18 or 15-20 amino acids, as compared to a wild type HPV66 L1 protein, and substitution of the amino acid residues at positions 347-357 of the wild type HPV66 L1 protein with the amino acid residues at positions 347-357 of a wild type HPV56 L1 protein.

In some preferred embodiments, the HPV virus-like particle according to the invention comprises the mutated HPV66 L1 protein, which has N-terminal truncation of 1-20 amino acids, for example, 1-20 amino acids, e.g. 1-5, 3-8, 5-10, 9-13, 10-15, 12-18 or 15-20 amino acids, as compared to a wild type HPV66 L1 protein, and substitution of the amino acid residues at positions 347-357 of the wild type HPV66 L1 protein with the amino acid residues at positions 347-357 of a wild type HPV56 L1 protein, and substitution of the amino acid residues at positions 51-60 of the wild type HPV66 L1 protein with the amino acid residues at positions 51-59 of a wild type HPV53 L1 protein.

In some preferred embodiments, the HPV virus-like particle according to the invention comprises the mutated HPV66 L1 protein, which has N-terminal truncation of 1-20 amino acids, for example, 1-20 amino acids, e.g. 1-5, 3-8, 5-10, 9-13, 10-15, 12-18 or 15-20 amino acids, as compared to a wild type HPV66 L1 protein, and substitution of the amino acid residues at positions 347-357 of the wild type HPV66 L1 protein with the amino acid residues at positions 347-357 of a wild type HPV56 L1 protein, and substitution of the amino acid residues at positions 114-150 of the wild type HPV66 L1 protein with the amino acid residues at positions 113-149 of a wild type HPV53 L1 protein.

In some preferred embodiments, the HPV virus-like particle according to the invention comprises the mutated HPV66 L1 protein, which has N-terminal truncation of 1-20 amino acids, for example, 1-20 amino acids, e.g. 1-5, 3-8, 5-10, 9-13, 10-15, 12-18 or 15-20 amino acids, as compared to a wild type HPV66 L1 protein, and substitution of the amino acid residues at positions 347-357 of the wild type HPV66 L1 protein with the amino acid residues at positions 347-357 of a wild type HPV56 L1 protein, and substitution of the amino acid residues at positions 259-283 of the wild type HPV66 L1 protein with the amino acid residues at positions 258-282 of a wild type HPV53 L1 protein.

In some preferred embodiments, the HPV virus-like particle according to the invention comprises the mutated HPV66 L1 protein, which has N-terminal truncation of 1-20 amino acids, for example, 1-20 amino acids, e.g. 1-5, 3-8, 5-10, 9-13, 10-15, 12-18 or 15-20 amino acids, as compared to a wild type HPV66 L1 protein, and substitution of the amino acid residues at positions 347-357 of the wild type HPV66 L1 protein with the amino acid residues at positions 347-357 of a wild type HPV56 L1 protein, and substitution of the amino acid residues at positions 114-150 of the wild type HPV66 L1 protein with the amino acid residues at positions 113-149 of a wild type HPV53 L1 protein, and substitution of the amino acid residues at positions 172-181 of the wild type HPV66 L1 protein with the amino acid residues at positions 171-180 of a wild type HPV53 L1 protein.

In a particularly preferred embodiment, the HPV virus-like particle according to the invention comprises the mutated HPV66 L1 protein, which has a sequence as set forth in SEQ ID NO: 7, 8, 9, 10, 11 or 63.

In another aspect, the invention further relates to a composition comprising the mutated HPV66 L1 protein or a variant thereof, the isolated nucleic acid, the vector, the host cell, or the HPV virus-like particle. In some preferred embodiments, the composition comprises the mutated HPV66 L1 protein or a variant thereof according to the invention. In some preferred embodiments, the composition comprises the HPV virus-like particle according to the invention.

In another aspect, the invention further relates to a pharmaceutical composition or vaccine, comprising the HPV virus-like particle according to the invention, and optionally a pharmaceutically acceptable carrier and/or excipient. The pharmaceutical composition or vaccine according to the invention can be used for preventing HPV infection, or a disease caused by HPV infection, such as cervical cancer and condyloma acuminatum.

In some preferred embodiments, the HPV virus-like particle is present in an amount effective for preventing HPV infection or a disease caused by HPV infection. In some preferred embodiments, the HPV infection is infection by one or more HPV types (e.g. HPV56 infection, HPV66 infection and/or HPV53 infection). In some preferred embodiments, the disease caused by HPV infection is selected from the group consisting of cervical cancer and condyloma acuminatum.

The pharmaceutical composition or vaccine according to the invention may be administrated by methods well known in the art, for example, but not limited to, orally or by injection. In the invention, a particularly preferred administration route is injection.

In some preferred embodiments, the pharmaceutical composition or vaccine according to the invention is administrated in a form of a unit dosage. For example, but not for limiting the invention, each unit dosage contains 5 μg-80 μg, preferably 20 μg-40 μg of HPV virus-like particle.

In another aspect, the invention relates to a method for preparing the mutated HPV66 L1 protein or a variant thereof as described above, comprising expressing the mutated HPV66 L1 protein or a variant thereof in a host cell, and then recovering the mutated HPV66 L1 protein or a variant thereof from a culture of the host cell.

In some preferred embodiments, the host cell is *E. coli*.

In some preferred embodiments, the method comprises the steps of: expressing the mutated HPV66 L1 protein or a variant thereof in *E. coli*, and then obtaining the mutated HPV66 L1 protein or a variant thereof by purifying a lysate supernatant of the *E. coli*. In some preferred embodiments, the mutated HPV66 L1 protein or a variant thereof is recovered from the lysate supernatant of the *E. coli* by chromatography (e.g. cation-exchange chromatography, hydroxyapatite chromatography and/or hydrophobic interaction chromatography).

In another aspect, the invention relates to a method for preparing a vaccine, comprising combining the HPV virus-like particle according to the invention with a pharmaceutically acceptable carrier and/or excipient.

In another aspect, the invention relates to a method for preventing HPV infection or a disease caused by HPV infection, comprising administering to a subject a prophylactically effective amount of the HPV virus-like particle or the pharmaceutical composition or vaccine according to the invention. In a preferred embodiment, the HPV infection is infection by one or more HPV types (e.g. HPV66 infection, HPV56 infection and/or HPV53 infection). In another preferred embodiment, the disease caused by HPV infection includes, but is not limited to cervical cancer and condyloma acuminatum. In another preferred embodiment, the subject is mammal, such as human.

In another aspect, the invention further relates to use of the mutated HPV66 L1 protein or a variant thereof or the HPV virus-like particle according to the invention in the manufacture of a pharmaceutical composition or vaccine for preventing HPV infection or a disease caused by HPV infection. In a preferred embodiment, the HPV infection is infection by one or more HPV types (e.g. HPV66 infection, HPV56 infection and/or HPV53 infection). In another preferred embodiment, the disease caused by HPV infection includes, but is not limited to, cervical cancer and condyloma acuminatum.

In another aspect, the invention further relates to the mutated HPV66 L1 protein or a variant thereof or the HPV virus-like particle according to the invention for the prevention of HPV infection or a disease caused by HPV infection. In a preferred embodiment, the HPV infection is infection by one or more HPV types (e.g. HPV66 infection, HPV56 infection and/or HPV53 infection). In another preferred embodiment, the disease caused by HPV infection includes, but is not limited to, cervical cancer and condyloma acuminatum.

Definitions of Terms in Present Invention

In the invention, unless otherwise specified, the scientific and technical terms used herein have the meanings generally understood by a person skilled in the art. Moreover, the laboratory operations of cell culture, molecular genetics, nucleic acid chemistry, and immunology used herein are the routine operations widely used in the corresponding fields. Meanwhile, in order to better understand the invention, the definitions and explanations of the relevant terms are provided as follows.

According to the invention, the term "a second type of wild-type HPV" refers to a wild-type HPV type other than HPV66. In the invention, a second type of wild-type HPV is preferably wild type HPV56.

According to the invention, the term "a third type of wild-type HPV" refers to a wild-type HPV type other than HPV66 and the second type of wild-type HPV. In the invention, a third type of wild-type HPV is preferably wild type HPV53.

According to the invention, the expression "corresponding positions" refers to the equivalent positions of the sequences being compared when the sequences are optimally aligned, i.e. the sequences are aligned to obtain a highest percentage of identity.

According to the invention, the term "wild type HPV66 L1 protein" refers to the naturally-occurring major capsid protein L1 in Human Papillomavirus Type 66 (HPV66). The sequence of wild type HPV66 L1 protein is well known in the art, and can be found in public database (such as Accession No. ABO76865.1, Q80961.1, ABO76858.1 and ALT54961.1 in NCBI database).

In the invention, when an amino acid sequence of wild type HPV66 L1 protein is mentioned, it is described by reference to the sequence as set forth in SEQ ID NO: 1. For example, the expression "amino acid residues at positions 53-56 of a wild type HPV66 L1 protein" refers to the amino acid residues at positions 53-56 of the polypeptide as set forth in SEQ ID NO: 1. However, a person skilled in the art understands that wild type HPV66 may include various isolates, and there might be difference in the amino acid sequence of L1 protein among various isolates. Furthermore, a person skilled in the art understands that although there might be difference in sequence, the amino acid sequences of L1 protein have a very high identity (generally higher than 95%, e.g. higher than 96%, higher than 97%, higher than 98%, or higher than 99%) among different HPV66 isolates, and have substantively the same biological function. Therefore, in the invention, the term "wild type HPV66 L1 protein" includes not only the protein as set forth in SEQ ID NO: 1, but also L1 protein of various HPV66 isolates (such as HPV66 L1 protein as set forth in ABO76865.1, Q80961.1, ABO76858.1 and ALT54961.1). Moreover, when a sequence fragment of a wild type HPV66 L1 protein is described, it includes not only the sequence fragment of SEQ ID NO: 1, but also the corresponding sequence fragment of a L1 protein of various HPV66 isolates. For example, the expression "amino acid residues at positions 53-56 of a wild type HPV66 L1 protein" includes the amino acid residues at positions 53-56 of SEQ ID NO: 1, and the corresponding fragment of a L1 protein of various HPV66 isolates.

According to the invention, the term "wild type HPV56 L1 protein" refers to the naturally-occurring major capsid protein L1 in Human Papillomavirus Type 56 (HPV56). The sequence of wild type HPV56 L1 protein is well known in the art, and can be found in public database (such as Accession No. ALT54892.1, ALT54864.1, P36743.1 and ABO76830.1 in NCBI database).

In the invention, when an amino acid sequence of wild type HPV56 L1 protein is mentioned, it is described by reference to the sequence as set forth in SEQ ID NO: 2. For example, the expression "amino acid residues at positions 347-357 of a wild type HPV56 L1 protein" refers to the amino acid residues at positions 347-357 of the polypeptide as set forth in SEQ ID NO: 2. However, a person skilled in the art understands that wild type HPV56 may include various isolates, and there might be difference in the amino acid sequence of L1 protein among various isolates. Furthermore, a person skilled in the art understands that although there might be difference in sequence, the amino acid sequences of L1 protein have a very high identity (generally higher than 95%, e.g. higher than 96%, higher than 97%, higher than 98%, or higher than 99%) among different HPV56 isolates, and have substantively the same biological function. Therefore, in the invention, the term "wild type HPV56 L1 protein" includes not only the protein as set forth in SEQ ID NO: 2, but also L1 protein of various HPV56 isolates (such as HPV56 L1 protein as set forth in ALT54892.1, ALT54864.1, P36743.1 and ABO76830.1). Moreover, when a sequence fragment of a wild type HPV56 L1 protein is described, it includes not only the sequence fragment of SEQ ID NO: 2, but also the corresponding sequence fragment of a L1 protein of various HPV56 isolates. For example, the expression "amino acid residues at positions 347-357 of a wild type HPV56 L1 protein" includes the amino acid residues at positions 347-357 of SEQ ID NO: 2, and the corresponding fragment of a L1 protein of various HPV56 isolates.

According to the invention, the term "wild type HPV53 L1 protein" refers to the naturally-occurring major capsid protein L1 in Human Papillomavirus Type 53 (HPV53). The sequence of wild type HPV53 L1 protein is well known in the art, and can be found in public database (such as Accession No. NP041848.1, ANY26596.1, ABU54090.1 and ALJ32506.1 in NCBI database).

In the invention, when an amino acid sequence of wild type HPV53 L1 protein is mentioned, it is described by reference to the sequence as set forth in SEQ ID NO: 3. For example, the expression "amino acid residues at positions 51-59 of a wild type HPV53 L1 protein" refers to amino acid residues at positions 51-59 of the polypeptide as set forth in SEQ ID NO: 3. However, a person skilled in the art understands that wild type HPV53 may include various isolates, and there might be difference in the amino acid sequence of L1 protein among various isolates. Furthermore, a person skilled in the art understands that although there might be difference in sequence, the amino acid sequences of L1 protein have a very high identity (generally higher than 95%, e.g. higher than 96%, higher than 97%, higher than 98%, or higher than 99%) among different HPV53 isolates, and have substantively the same biological function. Therefore, in the invention, the term "wild type HPV53 L1 protein" includes not only the protein as set forth in SEQ ID NO: 3, but also L1 protein of various HPV53 isolates (such as HPV53 L1 protein as set forth in NP041848.1, ANY26596.1, ABU54090.1 and ALJ32506.1). Moreover, when a sequence fragment of a wild type HPV53 L1 protein is described, it includes not only the sequence fragment of SEQ ID NO: 3, but also the corresponding sequence fragment of L1 protein of various HPV53 isolates. For example, the expression "amino acid residues at positions 51-59 of a wild type HPV53 L1 protein" includes the amino acid residues at positions 51-59 of SEQ ID NO: 3, and the corresponding fragment of L1 protein of various HPV53 isolates.

According to the invention, the expression "corresponding sequence fragments" or "corresponding fragments"

refers to the fragments that are located at equivalent positions of the sequences being compared when the sequences are optimally aligned, i.e. the sequences are aligned to obtain a highest percentage of identity.

According to the invention, the expression "N-terminal truncation of X amino acids" or "having X amino acids truncated at N-terminal" refers to substitution of the amino acid residues from positions 1 to X at the N-terminal of a protein with methionine residue encoded by an initiator codon (for initiating protein translation). For example, a HPV66 L1 protein having 5 amino acids truncated at N-terminal refers to a protein resulted from substituting the amino acid residues from positions 1 to 5 at the N-terminal of wild type HPV66 L1 protein with methionine residue encoded by an initiator codon.

According to the invention, the term "variant" refers to a protein, whose amino acid sequence has substitution (preferably conservative substitution), addition or deletion of one or more (e.g. 1, 2, 3, 4, 5, 6, 7, 8 or 9) amino acids, or has an identity of at least 90%, 95%, 96%, 97%, 98%, or 99%, as compared with the mutated HPV66 L1 protein according to the invention (for example, the protein as set forth in SEQ ID NO: 7, 8, 9, 10 or 11), and which retains a function of the mutated HPV66 L1 protein according to the invention. In the invention, the term "function of the mutated HPV66 L1 protein" refers to a capability of inducing generation of neutralizing antibodies against at least two HPV types (e.g. HPV66 and HPV56, or HPV66, HPV56 and HPV53). The term "identity" refers to a measure of similarity between nucleotide sequences or amino acid sequences. Generally, sequences were aligned to obtain a maximum matching. "Identity" has well-known meanings in the art and can be calculated by published algorithm (such as BLAST).

According to the invention, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by for example using a computer program such as Align program (DNAstar, Inc.) which is based on the method of Needleman, et al. (J. Mol. Biol. 48:443-453, 1970). The percent identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, and with a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and with a gap weight of 16, 14, 12, 10, 8, 6, or 4 and a length weight of 1, 2, 3, 4, 5, or 6.

As used herein, the term "conservative substitution" refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having basic side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, and tryptophan), amino acids having nonpolar side chains (for example, alanine, valine, leucine, isoleucine, proline, phenylalanine, and methionine), amino acids having β-branched side chains (such as threonine, valine, and isoleucine) and amino acids having aromatic side chains (for example, tyrosine, phenylalanine, tryptophan, and histidine). Therefore, generally a conservative substitution refers to a substitution of a corresponding amino acid residue with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

According to the invention, the term "E. coli expression system" refers to an expression system consisting of E. coli (strain) and a vector, wherein the E. coli (strain) is derived from the commercially available strains, including, but not limited to: ER2566, BL21 (DE3), B834 (DE3), and BLR (DE3).

According to the invention, the term "vector" refers to a nucleic acid carrier tool which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, etc.

According to the invention, the term "a pharmaceutically acceptable carrier and/or excipient" refers to a carrier and/or excipient that is pharmacologically and/or physiologically compatible to a subject and active ingredients, which is well known in the art (see, for example, Remington's Pharmaceutical Sciences. Edited by Gennaro A R, 19th ed. Pennsylvania: Mack Publishing Company, 1995), including, but not limited to: pH regulators, surfactants, adjuvants, and ionic strength enhancers. For example, pH regulators include, but are not limited to, phosphate buffers; surfactants include, but are not limited to: cation surfactants, anion surfactants, or non-ionic surfactants, e.g., Tween-80; adjuvants include, but are not limited to, aluminium adjuvant (e.g., aluminium hydroxide), and Freund's adjuvant (e.g., Freund's complete adjuvant); and ionic strength enhancers include, but are not limited to, NaCl.

According to the invention, the term "an effective amount" refers to an amount that can effectively achieve the intended purpose. For example, an amount effective for preventing a disease (such as HPV infection) refers to an amount effective for preventing, suppressing, or delaying the occurrence of a disease (such as HPV infection). The determination of such an effective amount is within the ability of a person skilled in the art.

According to the invention, the term "chromatography" includes, but is not limited to: ion exchange chromatography (such as cation-exchange chromatography), hydrophobic interaction chromatography, absorbent chromatography (such as hydroxyapatite chromatography), gel filtration chromatography (gel exclusion chromatography), and affinity chromatography.

According to the invention, the term "lysate supernatant" refers to a solution produced by the following steps: host cells (such as E. coli) are disrupted in a lysis buffer, and the insoluble substances are then removed from the lysed solution containing the disrupted host cells. Various lysis buffers are well known in the art, including, but not limited to Tris buffers, phosphate buffers, HEPES buffers, MOPS buffers, etc. In addition, the disrupting of a host cell can be accomplished by methods well known by a person skilled in the art, including, but not limited to homogenizer disrupting, ultrasonic treatment, grinding, high pressure extrusion, lysozyme treatment, etc. Methods for removing insoluble substances are also well known by a person skilled in the art, including, but not limited to filtration and centrifugation.

Beneficial Effects of Invention

Studies show that although there is certain cross-protection between HPV66 and other HPV type(s) (such as HPV56 and HPV53), such cross-protection is very low, generally lower than one percent, even one thousandth of the protection level of VLP of the same HPV type. Therefore, a subject vaccinated with HPV66 vaccine, still has a high risk of being infected by other HPV type(s) (such as HPV56 and HPV53).

The invention provides a mutated HPV66 L1 protein and a HPV virus-like particle formed by the same. The HPV virus-like particle according to the invention can provide significant cross-protection against HPV66 and other HPV type(s) (such as HPV56 and HPV53). Especially, at the same immunizing dose, the HPV virus-like particle according to the invention can induce the generation of high-titer neutralizing antibodies against at least two HPV types (e.g. HPV66 and HPV56, or HPV66, HPV56 and HPV53) in organisms, and its effect is comparable to that of a mixture of VLPs of multiple HPV types (e.g. a mixture of HPV66 VLP and HPV56 VLP, or a mixture of HPV66 VLP, HPV56 VLP and HPV53 VLP). Therefore, the HPV virus-like particle according to the invention can be used to prevent infection by at least two HPV types (e.g. HPV66 and HPV56, or HPV66, HPV56 and HPV53) at the same time as well as diseases associated with the infection, and has significantly beneficial technical effects. This has particularly significant advantages in terms of extending the protection range of HPV vaccines and reducing the production cost of HPV vaccines.

The embodiments of the invention are further described in detail by reference to the drawings and examples. However, a person skilled in the art would understand that the following drawings and examples are intended for illustrating the invention only, rather than defining the scope of the invention. According to the detailed description of the following drawings and preferred embodiments, various purposes and advantages of the invention are apparent for a person skilled in the art.

FIGS. 7A-7L show the transmission electron microscopy (TEM) photographs (taken at 100,000× magnification, Bar=0.1 μm) of various VLP samples. FIG. 7A, VLP assembled by HPV66N5; FIG. 7B, VLP assembled by HPV56N0; FIG. 7C, VLP assembled by H66N5-56T1; FIG. 7D, VLP assembled by H66N5-56T2; FIG. 7E, VLP assembled by H66N5-56T3; FIG. 7F, VLP assembled by H66N5-56T4; FIG. 7G, VLP assembled by H66N5-56T5; FIG. 7H, VLP assembled by HPV53N5; FIG. 7I, VLP assembled by H66N5-56T5-53S1, with a smaller diameter; FIG. 7J, VLP assembled by H66N5-56T5-53S2; FIG. 7K, VLP assembled by H66N5-56T5-53S4; FIG. 7L, VLP assembled by H66N5-56T5-53S2-53S3. The results showed that H66N5-56T1, H66N5-56T2, H66N5-56T3, H66N5-56T4, H66N5-56T5, H66N5-56T5-53S2, H66N5-56T5-53S4 and H66N5-56T5-53S2-53S3 were similar to HPV56N0, HPV66N5 and HPV53N5, and were able to assemble into VLPs with a radius of about 25 nm, however, VLPs formed by H66N5-56T5-53S2 and H66N5-56T5-53S2-53S3 contained small particles with a diameter of about 20 nm; while H66N5-56T5-53S1 was able to assemble into irregular VLP with a radius of about 10-20 nm.

FIGS. 8A-8C show the evaluation result of immune protection of H66N5-56T1 VLP, H66N5-56T2 VLP, H66N5-56T3 VLP, H66N5-56T4 VLP and H66N5-56T5 VLP in mice of the Experimental groups, and of HPV56N0 VLP, HPV66N5 VLP and the mixed HPV56/HPV66 VLP in mice of the Control groups. The result showed that H66N5-56T4 VLP and H66N5-56T5 VLP each could induce the generation of high-titer neutralizing antibodies against HPV66 and HPV56 in mice; and their protective effects against HPV66 were comparable to that of HPV66N5 VLP alone, and were significantly higher than that of HPV56N0VLP alone; and their protective effects against HPV56 were comparable to that of HPV56N0 VLP alone, and were significantly higher than that of HPV66N5 VLP alone. This showed that H66N5-56T4 VLP and H66N5-56T5 VLP could be used as effective vaccines for preventing HPV66 infection and HPV56 infection, and could be used in place of a mixed vaccine comprising HPV66 VLP and HPV56 VLP.

FIGS. 9A-9B show the evaluation result of immune protection of H66N5-56T5-53S1 VLP, H66N5-56T5-53S2 VLP and H66N5-56T5-53S4 VLP in mice of the Experimental groups, and of HPV66N5 VLP, HPV56N0 VLP, HPV53N5 VLP and the mixed HPV66/56/53 VLP in mice of the Control groups. The result showed that H66N5-56T5-53S1 VLP, H66N5-56T5-53S2 VLP and H66N5-56T5-53S4 VLP each could induce the generation of high-titer neutralizing antibodies against HPV66, HPV56 and HPV53 in mice; and their protective effects against HPV66 were comparable to that of HPV66N5 VLP alone and that of the mixed HPV66/56/53 VLP, and were significantly higher than that of HPV56N0 VLP alone and that of HPV53N5 VLP alone; and their protective effects against HPV56 were comparable to that of HPV56N0 VLP alone and that of the mixed HPV66/56/53 VLP, and were significantly higher than that of HPV66N5 VLP alone and that of HPV53N5 VLP alone; and their protective effects against HPV53 were comparable to that of HPV53N5 VLP alone and that of the mixed HPV66/56/53 VLP, and were significantly higher than that of HPV66N5 VLP alone and that of HPV56N0 VLP alone. This showed that H66N5-56T5-53S1 VLP, H66N5-56T5-53S2 VLP and H66N5-56T5-53S4 VLP could be used as effective vaccines for preventing HPV66 infection, HPV56 infection and HPV53 infection, and could be used in place of a mixed vaccine comprising HPV66 VLP, HPV56 VLP and HPV53 VLP.

FIG. 10 shows the evaluation result of immune protection of H66N5-56T5-53S2-53S3 VLP in mice of the Experimental groups, and of HPV66N5 VLP, HPV56N0 VLP, HPV53N5 VLP and the mixed HPV66/56/53 VLP in mice of the Control groups. The result showed that H66N5-56T5-53S2-53S3 VLP could induce the generation of high-titer neutralizing antibodies against HPV66, HPV56 and HPV53 in mice; and its protective effects against HPV66 was comparable to that of HPV66N5 VLP alone and that of the mixed HPV66/56/53 VLP, and was significantly higher than that of HPV56N0 VLP alone and that of HPV53N5 VLP alone; and its protective effects against HPV56 was slightly weaker than that of HPV56N0 VLP alone, that of HPV66N5 VLP alone and that of the mixed HPV66/56/53 VLP, but was significantly higher than that of HPV53N5 VLP alone; and its protective effects against HPV53 was slightly weaker than that of HPV53N5 VLP alone and that of the mixed HPV66/56/53 VLP, but was significantly higher than that of HPV66N5 VLP alone and that of HPV56N0 VLP alone. This showed that H66N5-56T5-53S2-53S3 VLP could be used as effective vaccines for preventing HPV66 infection, HPV56 infection and HPV53 infection, and could be used in place of a mixed vaccine comprising HPV66 VLP, HPV56 VLP and HPV53 VLP.

SEQUENCE INFORMATION

Some of the sequences involved in the invention are provided in the following Table 1.

TABLE 1

| Description of sequences | |
|---|---|
| SEQ ID NO: | Description |
| 1 | wild type HPV66 L1 protein |
| 2 | wild type HPV56 L1 protein |
| 3 | wild type HPV53 L1 protein |
| 4 | the mutated HPV66 L1 protein comprising Segment 1 of HPV56 L1 protein, H66N5-56T1 |
| 5 | the mutated HPV66 L1 protein comprising Segment 2 of HPV56 L1 protein, H66N5-56T2 |

TABLE 1-continued

Description of sequences

Figure 1:
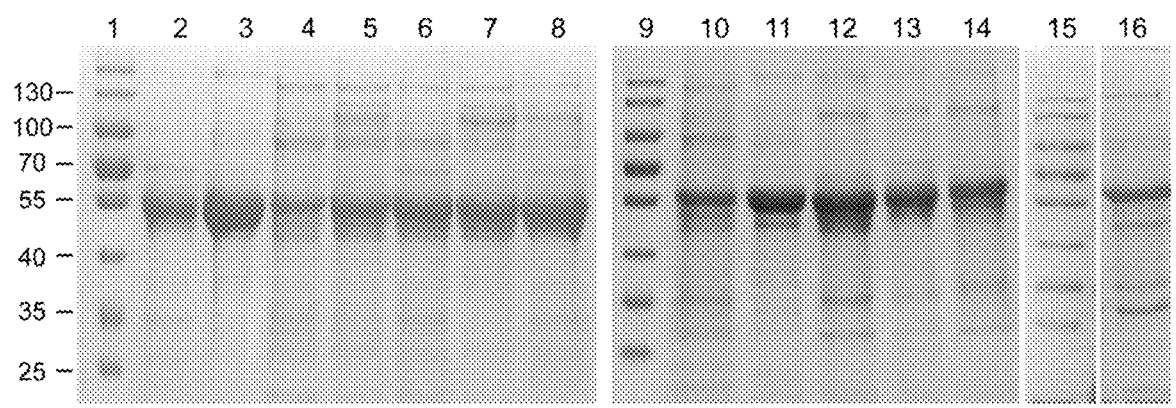
FIG. 1 shows the SDS-PAGE result of the purified mutated proteins in Example 1. Lane 1: protein molecular weight marker; Lane 2: HPV66N5 (HPV66 L1 protein having 5 amino acids truncated at N-terminal); Lane 3: HPV56N0 (full-length HPV56 L1 protein); Lane 4: H66N5-56T1; Lane 5: H66N5-56T2; Lane 6: H66N5-56T3; Lane 7: H66N5-56T4; Lane 8: H66N5-56T5; Lane 9: protein molecular weight marker; Lane 10: H66N5-56T5; Lane 11: HPV53N5 (HPV53 L1 protein having 5 amino acids truncated at N-terminal); Lane 12: H66N5-56T5-53S1; Lane 13: H66N5-56T5-53S2; Lane 14: H66N5- 56T5-53S4; Lane 15: protein molecular weight marker; Lane 16: H66N5-56T5-53S2-53S3. The result showed that after chromatographic purification, H66N5-56T1, H66N5-56T2, H66N5-56T3, H66N5-56T4, H66N5-56T5, H66N5-56T5-53S1, H66N5-56T5-53S2, and H66N5-56T5-53S4 protein had a purity of about 90%, H66N5-56T5-53S2-53S3 protein had a purity of about 75%.

| SEQ ID NO: | Description |
|---|---|
| 6 | the mutated HPV66 L1 protein comprising Segment 3 of HPV56 L1 protein, H66N5-56T3 |
| 7 | the mutated HPV66 L1 protein comprising Segment 4 of HPV56 L1 protein, H66N5-56T4 |
| 8 | the mutated HPV66 L1 protein comprising Segment 5 of HPV56 L1 protein, H66N5-56T5 |
| 9 | the mutated HPV66 L1 protein comprising Segment 5 of HPV56 L1 protein and Segment 1 of HPV53 L1 protein, H66N5-56T5-53S1 |
| 10 | the mutated HPV66 L1 protein comprising Segment 5 of HPV56 L1 protein and Segment 2 of HPV53 L1 protein, H66N5-56T5-53S2 |
| 11 | the mutated HPV66 L1 protein comprising Segment 5 of HPV56 L1 protein and Segment 4 of HPV53 L1 protein, H66N5-56T5-53S4 |
| 12 | the DNA sequence encoding SEQ ID NO: 1 |
| 13 | the DNA sequence encoding SEQ ID NO: 2 |
| 14 | the DNA sequence encoding SEQ ID NO: 3 |
| 15 | the DNA sequence encoding SEQ ID NO: 4 |
| 16 | the DNA sequence encoding SEQ ID NO: 5 |
| 17 | the DNA sequence encoding SEQ ID NO: 6 |
| 18 | the DNA sequence encoding SEQ ID NO: 7 |
| 19 | the DNA sequence encoding SEQ ID NO: 8 |
| 20 | the DNA sequence encoding SEQ ID NO: 9 |
| 21 | the DNA sequence encoding SEQ ID NO: 10 |
| 22 | the DNA sequence encoding SEQ ID NO: 11 |
| 23 | the sequence of the amino acid residues at positions 347-357 of wild type HPV56 L1 protein, Segment 5 of HPV56 L1 protein |
| 24 | the sequence of the amino acid residues at positions 51-59 of wild type HPV53 L1 protein, Segment 1 of HPV53 L1 protein |
| 25 | the sequence of the amino acid residues at positions 113-149 of wild type HPV53 L1 protein, Segment 2 of HPV53 L1 protein |
| 26 | the sequence of the amino acid residues at positions 258-282 of wild type HPV53 L1 protein, Segment 4 of HPV53 L1 protein |
| 27 | the sequence of the amino acid residues at positions 53-56 of wild type HPV56 L1 protein, Segment 1 of HPV56 L1 protein |
| 28 | the HPV66 L1 protein having 5 amino acids truncated at N-terminal, HPV66N5 |
| 29 | the DNA sequence encoding SEQ ID NO: 28 |
| 30 | the sequence of the amino acid residues at positions 178-180 of wild type HPV56 L1 protein, Segment 3 of HPV56 L1 protein |
| 31 | the HPV53 L1 protein having 5 amino acids truncated at N-terminal, HPV53N5 |
| 32 | the DNA sequence encoding SEQ ID NO: 31 |
| 33 | the sequence of the amino acid residues at positions 130-150 of wild type HPV56 L1 protein, Segment 2 of HPV56 L1 protein |
| 34 | the sequence of the amino acid residues at positions 265-283 of wild type HPV56 L1 protein, Segment 4 of HPV56 L1 protein |
| 63 | the mutated HPV66 L1 protein comprising Segment 5 of HPV56 L1 protein and Segment 2 of HPV53 L1 protein and Segment 3 of HPV53 L1 protein, H66N5-56T5-53S2-53S3 |
| 64 | the DNA sequence encoding SEQ ID NO: 63 |
| 65 | the sequence of the amino acid residues at positions 171-180 of wild type HPV53 L1 protein, Segment 3 of HPV53 L1 protein |

```
Sequence 1 (SEQ ID NO: 1):
MAMWRPSDNKVYLPPTPVSKVVATDTYVKRTSIFYHAGSSRLLAVGHPYYSVSKSGTKTNIPKV

SAYQYRVFRVRLPDPNKFGLPDPSFYNPDQERLVWACVGLEVGRGQPLGAGLSGHPLFNRLDDT

EVSNLAGNNVIEDSRDNISVDCKQTQLCIVGCAPALGEHWTKGAVCKSTPGNTGDCPPLALVNT

PIEDGDMVDTGFGAMDFKLLQESKAEVPLDIVQSTCKYPDYLKMSADAYGDSMWFYLRREQLF

ARHYFNRAGNVGLAIPTDLYWKGGNGRDPPPSSVYVATPSGSMITSEAQLFNKPYWLQRAQGH

NNGICWGNQVFVTVVDTTRSTNMTINAAKSTLTKYDAREINQYLRHVELYELQFVFQLCKITLT

AEVMAYLHNMNNTLLDDWNIGLSPPVATSLEDKYRYIKSTAITCQREQPPAEKQDPLAKYKFWE

VNLQDSFSADLDQFPLGRKFLMQLGPRPPRPKASVSASKRRAAPTSSSSPAKRKK.

Sequence 2 (SEQ ID NO: 2):
MATWRPSENKVYLPPTPVSKVVATDSYVKRTSIFYHAGSSRLLAVGHPYYSVTKDNTKTNIPKV
```

-continued

SAYQYRVFRVRLPDPNKFGLPDTNIYNPDQERLVWACVGLEVGRGQPLGAGLSGHPLFNRLDDT

ESSNLANNNVIEDSRDNISVDGKQTQLCIVGCTPAMGEHWTKGAVCKSTQVTTGDCPPLALINTP

IEDGDMIDTGFGAMDFKVLQESKAEVPLDIVQSTCKYPDYLKMSADAYGDSMWFYLRREQLFA

RHYFNRAGKVGETIPAELYLKGSNGREPPPSSVYVATPSGSMITSEAQLFNKPYWLQRAQGHNN

GICWGNQLFVTVVDTTRSTNMTISTATEQLSKYDARKINQYLRHVELYELQFVFQLCKITLSALV

MAYLHNMNANLLEDWNIGLSPPVATSLEDKYRYVRSTAITCQREQPPTEKQDPLAKYKFWDVN

LQDSFSTDLDQFPLGRKFLMQLGTRSKPAVATSKKRSAPTSTSTPAKRKRR.

Sequence 3 (SEQ ID NO: 3):
MAVWRPSDSKVYLPPTPVSKVITTDAYVKRTTIFYHAGSSRLLTVGHPYYPISKSGKADIPKVSAF

QYRVFRVRLPDPNKFGLPDTNIFNPDQERLVWACVGLEIGRGQPLGVGVSGHPLFNRLDDTESSS

IAIQDTAPDSRDNVSVDPKQTQLCIIGCAPAIGEHWTKGTACRSTPTTAGDCPPLELINSPIEDGDM

VDTGFGALNFKALQESKSDVPLDIVQSTCKYPDYLKMSADAYGDSMWFYLRREQLFTRHFFNR

AGVIGEEIPNDLYIKGSNGRDPPPSSVYVATPSGSMITSEAQLFNKPYWLQRAQGHNNGICWNNQ

LFVTVVDTTRNTNMTLSATTQSMSTYNSKQIKQYVRHAEEYELQFVFQLCKISLSAEVMAYLHT

MNSTLLEDWNIGLSPPVATSLEDKYRYVKSAAITCQKDQPPPEKQDPLSKYKFWEVNLQNSFSA

DLDQFPLGRKFLMQVGVRTKPPVSSKKRSASTTSTSAPSSKRKRK.

Sequence 4 (SEQ ID NO: 4):
MPSDNKVYLPPTPVSKVVATDTYVKRTSIFYHAGSSRLLAVGHPYYSVTKDNTKTNIPKVSAYQ

YRVFRVRLPDPNKFGLPDPSFYNPDQERLVWACVGLEVGRGQPLGAGLSGHPLFNRLDDTEVSN

LAGNNVIEDSRDNISVDCKQTQLCIVGCAPALGEHWTKGAVCKSTPGNTGDCPPLALVNTPIEDG

DMVDTGFGAMDFKLLQESKAEVPLDIVQSTCKYPDYLKMSADAYGDSMWFYLRREQLFARHY

FNRAGNVGEAIPTDLYWKGGNGRDPPPSSVYVATPSGSMITSEAQLFNKPYWLQRAQGHNNGIC

WGNQVFVTVVDTTRSTNMTINAAKSTLTKYDAREINQYLRHVEEYELQFVFQLCKITLTAEVMA

YLHNMNMNNTLLDDWNIGLSPPVATSLEDKYRYIKSTAITCQREQPPAEKQDPLAKYKFWEVNLQD

SFSADLDQFPLGRKFLMQLGPRPPRPKASVSASKRRAAPTSSSSSPAKRKK.

Sequence 5 (SEQ ID NO: 5):
MPSDNKVYLPPTPVSKVVATDTYVKRTSIFYHAGSSRLLAVGHPYYSVSKSGTKTNIPKVSAYQY

RVFRVRLPDPNKFGLPDPSFYNPDQERLVWACVGLEVGRGQPLGAGLSGHPLFNRLDDTESSNL

ANNNVIEDSRDNISVDGKQTQLCIVGCAPALGEHWTKGAVCKSTPGNTGDCPPLALVNTPIEDG

DMVDTGFGAMDFKLLQESKAEVPLDIVQSTCKYPDYLKMSADAYGDSMWFYLRREQLFARHY

FNRAGNVGEAIPTDLYWKGGNGRDPPPSSVYVATPSGSMITSEAQLFNKPYWLQRAQGHNNGIC

WGNQVFVTVVDTTRSTNMTINAAKSTLTKYDAREINQYLRHVEEYELQFVFQLCKITLTAEVMA

YLHNMNMNNTLLDDWNIGLSPPVATSLEDKYRYIKSTAITCQREQPPAEKQDPLAKYKFWEVNLQD

SFSADLDQFPLGRKFLMQLGPRPPRPKASVSASKRRAAPTSSSSSPAKRKK.

Sequence 6 (SEQ ID NO: 6):
MPSDNKVYLPPTPVSKVVATDTYVKRTSIFYHAGSSRLLAVGHPYYSVSKSGTKTNIPKVSAYQY

RVFRVRLPDPNKFGLPDPSFYNPDQERLVWACVGLEVGRGQPLGAGLSGHPLFNRLDDTEVSNL

AGNNVIEDSRDNISVDCKQTQLCIVGCAPALGEHWTKGAVCKSTQVTTGDCPPLALVNTPIEDG

DMVDTGFGAMDFKLLQESKAEVPLDIVQSTCKYPDYLKMSADAYGDSMWFYLRREQLFARHY

FNRAGNVGEAIPTDLYWKGGNGRDPPPSSVYVATPSGSMITSEAQLFNKPYWLQRAQGHNNGIC

WGNQVFVTVVDTTRSTNMTINAAKSTLTKYDAREINQYLRHVEEYELQFVFQLCKITLTAEVMA

YLHNMNMNNTLLDDWNIGLSPPVATSLEDKYRYIKSTAITCQREQPPAEKQDPLAKYKFWEVNLQD

SFSADLDQFPLGRKFLMQLGPRPPRPKASVSASKRRAAPTSSSSSPAKRKK.

```
Sequence 7 (SEQ ID NO: 7):
MPSDNKVYLPPTPVSKVVATDTYVKRTSIFYHAGSSRLLAVGHPYYSVSKSGTKTNIPKVSAYQY
RVFRVRLPDPNKFGLPDPSFYNPDQERLVWACVGLEVGRGQPLGAGLSGHPLFNRLDDTEVSNL
AGNNVIEDSRDNISVDCKQTQLCIVGCAPALGEHWTKGAVCKSTPGNTGDCPPLALVNTPIEDGD
MVDTGFGAMDFKLLQESKAEVPLDIVQSTCKYPDYLKMSADAYGDSMWFYLRREQLFARHYF
NRAGKVGETIPAELYLKGSNGREPPPSSVYVATPSGSMITSEAQLFNKPYWLQRAQGHNNGICW
GNQVFVTVVDTTRSTNMTINAAKSTLTKYDAREINQYLRHVEEYELQFVFQLCKITLTAEVMAY
LHNMNNTLLDDWNIGLSPPVATSLEDKYRYIKSTAITCQREQPPAEKQDPLAKYKFWEVNLQDS
FSADLDQFPLGRKFLMQLGPRPPRPKASVSASKRRAAPTSSSSSPAKRKK.

Sequence 8 (SEQ ID NO: 8):
MPSDNKVYLPPTPVSKVVATDTYVKRTSIFYHAGSSRLLAVGHPYYSVSKSGTKTNIPKVSAYQY
RVFRVRLPDPNKFGLPDPSFYNPDQERLVWACVGLEVGRGQPLGAGLSGHPLFNRLDDTEVSNL
AGNNVIEDSRDNISVDCKQTQLCIVGCAPALGEHWTKGAVCKSTPGNTGDCPPLALVNTPIEDGD
MVDTGFGAMDFKLLQESKAEVPLDIVQSTCKYPDYLKMSADAYGDSMWFYLRREQLFARHYF
NRAGNVGEAIPTDLYWKGGNGRDPPPSSVYVATPSGSMITSEAQLFNKPYWLQRAQGHNNGIC
WGNQVFVTVVDTTRSTNMTINAATEQLSKYDARKINQYLRHVEEYELQFVFQLCKITLTAEVMA
YLHNMNNTLLDDWNIGLSPPVATSLEDKYRYIKSTAITCQREQPPAEKQDPLAKYKFWEVNLQD
SFSADLDQFPLGRKFLMQLGPRPPRPKASVSASKRRAAPTSSSSSPAKRKK.

Sequence 9 (SEQ ID NO: 9):
MPSDNKVYLPPTPVSKVVATDTYVKRTSIFYHAGSSRLLAVGHPYYPISKSGKADIPKVSAYQYR
VFRVRLPDPNKFGLPDPSFYNPDQERLVWACVGLEVGRGQPLGAGLSGHPLFNRLDDTEVSNLA
GNNVIEDSRDNISVDCKQTQLCIVGCAPALGEHWTKGAVCKSTPGNTGDCPPLALVNTPIEDGD
MVDTGFGAMDFKLLQESKAEVPLDIVQSTCKYPDYLKMSADAYGDSMWFYLRREQLFARHYF
NRAGNVGEAIPTDLYWKGGNGRDPPPSSVYVATPSGSMITSEAQLFNKPYWLQRAQGHNNGIC
WGNQVFVTVVDTTRSTNMTINAATEQLSKYDARKINQYLRHVEEYELQFVFQLCKITLTAEVMA
YLHNMNNTLLDDWNIGLSPPVATSLEDKYRYIKSTAITCQREQPPAEKQDPLAKYKFWEVNLQD
SFSADLDQFPLGRKFLMQLGPRPPRPKASVSASKRRAAPTSSSSSPAKRKK.

Sequence 10 (SEQ ID NO: 10):
MPSDNKVYLPPTPVSKVVATDTYVKRTSIFYHAGSSRLLAVGHPYYSVSKSGTKTNIPKVSAYQY
RVFRVRLPDPNKFGLPDPSFYNPDQERLVWACVGLEVGRGQPLGVGVSGHPLFNRLDDTESSSIA
IQDTAPDSRDNVSVDPKQTQLCIVGCAPALGEHWTKGAVCKSTPGNTGDCPPLALVNTPIEDGD
MVDTGFGAMDFKLLQESKAEVPLDIVQSTCKYPDYLKMSADAYGDSMWFYLRREQLFARHYF
NRAGNVGEAIPTDLYWKGGNGRDPPPSSVYVATPSGSMITSEAQLFNKPYWLQRAQGHNNGIC
WGNQVFVTVVDTTRSTNMTINAATEQLSKYDARKINQYLRHVEEYELQFVFQLCKITLTAEVMA
YLHNMNNTLLDDWNIGLSPPVATSLEDKYRYIKSTAITCQREQPPAEKQDPLAKYKFWEVNLQD
SFSADLDQFPLGRKFLMQLGPRPPRPKASVSASKRRAAPTSSSSSPAKRKK.

Sequence 11 (SEQ ID NO: 11):
MPSDNKVYLPPTPVSKVVATDTYVKRTSIFYHAGSSRLLAVGHPYYSVSKSGTKTNIPKVSAYQY
RVFRVRLPDPNKFGLPDPSFYNPDQERLVWACVGLEVGRGQPLGAGLSGHPLFNRLDDTEVSNL
AGNNVIEDSRDNISVDCKQTQLCIVGCAPALGEHWTKGAVCKSTPGNTGDCPPLALVNTPIEDGD
MVDTGFGAMDFKLLQESKAEVPLDIVQSTCKYPDYLKMSADAYGDSMWFYLRREQLFARHFFN
RAGVIGEEIPNDLYIKGSNGRDPPPSSVYVATPSGSMITSEAQLFNKPYWLQRAQGHNNGICWGN
QVFVTVVDTTRSTNMTINAATEQLSKYDARKINQYLRHVELYELQFVFQLCKITLTALVMAYLH
```

NMNNTLLDDWNIGLSPPVATSLEDKYRYIKSTAITCQREQPPAEKQDPLAKYKFWEVNLQDSFS

ADLDQFPLGRKFLMQLGPRPPRPKASVSASKRRAAPTSSSSSPAKRKK.

Sequence 12 (SEQ ID NO: 12):
ATGGCCATGTGGAGGCCCAGCGACAACAAGGTGTACCTGCCCCCACCCCCGTGAGCAAGGT

GGTGGCCACCGACACCTACGTGAAGAGGACCAGCATCTTCTACCACGCCGGCAGCAGCAGG

CTGCTGGCCGTGGGCCACCCCTACTACAGCGTGAGCAAGAGCGGCACCAAGACCAACATCCC

CAAGGTGAGCGCCTACCAGTACAGGGTGTTCAGGGTGAGGCTCCCCGACCCCAACAAGTTCG

GCCTGCCCGACCCCAGCTTCTACAACCCCGACCAGGAGAGGCTGGTGTGGGCCTGCGTGGGC

CTGGAGGTGGGCAGGGGCCAGCCCCTGGGCGCCGGCCTGAGCGGCCACCCCCTGTTCAACAG

GCTGGACGACACCGAGGTGAGCAACCTGGCCGGCAACAACGTGATCGAGGACAGCAGGGAC

AACATCAGCGTGGACTGCAAGCAGACCCAGCTGTGCATCGTGGGCTGCGCCCCCGCCCTGGG

CGAGCACTGGACCAAGGGCGCCGTGTGCAAGAGCACCCCCGGCAACACCGGCGACTGCCCC

CCCCTGGCCCTGGTGAACACCCCCATCGAGGACGGCGACATGGTGGACACCGGCTTCGGCGC

CATGGACTTCAAGCTGCTGCAGGAGAGCAAGGCCGAGGTGCCCCTGGACATCGTGCAGAGC

ACCTGCAAGTACCCCGACTACCTGAAGATGAGCGCCGACGCCTACGGCGACAGCATGTGGTT

CTACCTGAGGAGGGAGCAGCTGTTCGCCAGGCACTACTTCAACAGGGCCGGCAACGTGGGC

GAGGCCATCCCCACCGACCTGTACTGGAAGGGCGGCAACGGCAGGGACCCCCCCCCCAGCA

GCGTGTACGTGGCCACCCCCAGCGGCAGCATGATCACCAGCGAGGCCCAGCTGTTCAACAAG

CCCTACTGGCTGCAGAGGGCCCAGGGCCACAACAACGGCATCTGCTGGGGCAACCAGGTGTT

CGTGACCGTGGTGGACACCACCAGGAGCACCAACATGACCATCAACGCCGCCAAGAGCACC

CTGACCAAGTACGACGCCAGGGAGATCAACCAGTACCTGAGGCACGTGGAGGAGTACGAGC

TGCAGTTCGTGTTCCAGCTGTGCAAGATCACCCTGACCGCCGAGGTGATGGCCTACCTGCAC

AACATGAACAACACCCTGCTGGACGACTGGAACATCGGCCTGAGCCCCCCCGTGGCCACCAG

CCTGGAGGACAAGTACAGGTACATCAAGAGCACCGCCATCACCTGCCAGAGGGAGCAGCCC

CCCGCCGAGAAGCAGGACCCCCTGGCCAAGTACAAGTTCTGGGAGGTGAACCTGCAGGACA

GCTTCAGCGCCGACCTGGACCAGTTCCCCCTGGGCAGGAAGTTCCTGATGCAGCTGGGCCCC

AGGCCCCCCAGGCCCAAGGCCAGCGTGAGCGCCAGCAAGAGGAGGGCCGCCCCCACCAGCA

GCAGCAGCAGCCCCGCCAAGAGGAAGAAGTAA

Sequence 13 (SEQ ID NO: 13):
ATGGCCACCTGGCGGCCCAGCGAGAACAAGGTGTACCTGCCCCCCACCCCCGTGTCCAAGGT

GGTGGCCACCGACAGCTACGTGAAGCGGACCAGCATCTTCTACCACGCCGGCAGCAGCAGA

CTGCTGGCCGTGGGCCACCCCTACTACAGCGTGACCAAGGACAACACCAAGACCAACATCCC

CAAGGTGTCCGCCTACCAGTACCGGGTGTTCAGAGTGCGGCTGCCTGACCCTAACAAGTTCG

GCCTGCCCGACACCAATATCTACAACCCCGACCAGGAACGGCTGGTCTGGGCCTGCGTGGGC

CTGGAAGTGGGCAGAGGCCAGCCTCTGGGAGCTGGCCTGAGCGGCCACCCCCTGTTCAACCG

GCTGGACGACACCGAGAGCAGCAACCTGGCCAACAACAACGTGATCGAGGACAGCCGGGAC

AACATCAGCGTGGACGGCAAGCAGACCCAGCTGTGCATCGTGGGCTGCACACCCGCCATGG

GCGAGCACTGGACCAAGGGCGCCGTGTGCAAGAGCACCCAGGTCACCACCGGCGACTGCCC

CCCTCTGGCCCTGATCAACACCCCCATCGAGGACGGCGACATGATCGACACCGGCTTCGGCG

CCATGGACTTCAAGGTGCTGCAGGAAAGCAAGGCCGAGGTCCCCCTGGACATCGTGCAGAG

CACCTGCAAGTACCCCGACTACCTGAAGATGAGCGCCGACGCCTACGGCGACAGCATGTGGT

```
-continued
TCTACCTGCGGCGGGAGCAGCTGTTCGCCCGGCACTACTTCAACAGAGCCGGCAAAGTGGGC

GAGACAATCCCCGCCGAGCTGTACCTGAAGGGCAGCAACGGACGGGAGCCTCCTCCCAGCA

GCGTGTACGTGGCCACCCCCAGCGGCAGCATGATCACCAGCGAGGCCCAGCTGTTCAACAAG

CCCTACTGGCTGCAGCGGGCCCAGGGCCACAACAACGGCATCTGCTGGGGCAACCAGCTGTT

CGTGACCGTCGTGGACACTACCCGGTCCACCAACATGACCATCAGCACCGCCACCGAGCAGC

TGTCCAAGTACGACGCCCGGAAGATCAACCAGTACCTGCGGCACGTGGAGGAATATGAGCT

GCAGTTCGTCTTTCAGCTGTGCAAGATCACCCTGAGCGCCGAAGTGATGGCCTACCTGCACA

ACATGAACGCCAACCTGCTGGAAGATTGGAACATCGGCCTGAGCCCCCCTGTGGCTACCTCT

CTGGAAGATAAGTACAGATACGTGCGGAGCACCGCCATCACCTGCCAGAGAGAGCAGCCCC

CCACCGAGAAGCAGGACCCCCTGGCCAAGTACAAGTTCTGGGACGTGAACCTGCAGGACAG

CTTCAGCACCGACCTGGACCAGTTCCCCCTGGGCCGGAAGTTCCTGATGCAGCTGGGCACCA

GATCCAAGCCCGCCGTGGCCACAAGCAAGAAGCGGAGCGCCCCCACAAGCACCAGCACCCC

CGCCAAGCGGAAGCGGAGATGA
```

Sequence 14 (SEQ ID NO: 14):
```
ATGGCCGTGTGGAGGCCCAGCGACAGCAAGGTGTACCTGCCCCCCACCCCCGTGAGCAAGGT

GATCACCACCGACGCCTACGTGAAGAGGACCACCATCTTCTACCACGCCGGCAGCAGCAGGC

TGCTGACCGTGGGCCACCCCTACTACCCCATCAGCAAGAGCGGCAAGGCCGACATCCCCAAG

GTGAGCGCCTTCCAGTACAGGGTGTTCAGGGTGAGGCTGCCCGACCCCAACAAGTTCGGCCT

GCCCGACACCAACATCTTCAACCCCGACCAGGAGAGGCTGGTGTGGGCCTGCGTGGGCCTGG

AGATCGGCAGGGGCCAGCCCCTGGGCGTGGGCGTGAGCGGCCACCCCCTGTTCAACAGGCTG

GACGACACCGAGAGCAGCAGCATCGCCATCCAGGACACCGCCCCCGACAGCAGGGACAACG

TGAGCGTGGACCCCAAGCAGACCCAGCTGTGCATCATCGGCTGCGCCCCCGCCATCGGCGAG

CACTGGACCAAGGGCACCGCCTGCAGGAGCACCCCCACCACCGCCGGCGACTGCCCCCCCCT

GGAGCTGATCAACAGCCCCATCGAGGACGGCGACATGGTGGACACCGGCTTCGGCGCCCTG

AACTTCAAGGCCCTGCAGGAGAGCAAGAGCGACGTGCCCCTGGACATCGTGCAGAGCACCT

GCAAGTACCCCGACTACCTGAAGATGAGCGCCGACGCCTACGGCGACAGCATGTGGTTCTAC

CTGAGGAGGGAGCAGCTGTTCACCAGGCACTTCTTCAACAGGGCCGGCGTGATCGGCGAGG

AGATCCCCAACGACCTGTACATCAAGGGCAGCAACGGCAGGGACCCCCCCCCCAGCAGCGT

GTACGTGGCCACCCCCAGCGGCAGCATGATCACCAGCGAGGCCCAGCTGTTCAACAAGCCCT

ACTGGCTGCAGAGGGCCCAGGGCCACAACAACGGCATCTGCTGGAACAACCAGCTGTTCGTG

ACCGTGGTGGACACCACCAGGAACACCAACATGACCCTGAGCGCCACCACCCAGAGCATGA

GCACCTACAACAGCAAGCAGATCAAGCAGTACGTGAGGCACGCCGAGGAGTACGAGCTGCA

GTTCGTGTTCCAGCTGTGCAAGATCAGCCTGAGCGCCGAGGTGATGGCCTACCTGCACACCA

TGAACAGCACCCTGCTGGAGGACTGGAACATCGGCCTGAGCCCCCCCGTGGCCACCAGCCTG

GAGGACAAGTACAGGTACGTGAAGAGCGCCGCCATCACCTGCCAGAAGGACCAGCCCCCCC

CCGAGAAGCAGGACCCCCTGAGCAAGTACAAGTTCTGGGAGGTGAACCTGCAGAACAGCTT

CAGCGCCGACCTGGACCAGTTCCCCCTGGGCAGGAAGTTCCTGATGCAGGTGGGCGTGAGGA

CCAAGCCCCCCGTGAGCAGCAAGAAGGAGCGCCAGCACCACCAGCACCAGCGCCCCCAG

CAGCAAGAGGAAGAGGAAGTAA
```

Sequence 15 (SEQ ID NO: 15):
```
ATGCCCAGCGACAACAAGGTGTACCTGCCCCCCACCCCCGTGAGCAAGGTGGTGGCCACCGA

CACCTACGTGAAGAGGACCAGCATCTTCTACCACGCCGGCAGCAGCAGGCTGCTGGCCGTGG
```

-continued

```
GCCACCCCTACTACAGCGTGACCAAGGACAACACCAAGACCAACATCCCCAAGGTGTCCGCC

TACCAGTACAGGGTGTTCAGGGTGAGGCTCCCCGACCCCAACAAGTTCGGCCTGCCCGACCC

CAGCTTCTACAACCCCGACCAGGAGAGGCTGGTGTGGGCCTGCGTGGGCCTGGAGGTGGGCA

GGGGCCAGCCCCTGGGCGCCGGCCTGAGCGGCCACCCCCTGTTCAACAGGCTGGACGACACC

GAGGTGAGCAACCTGGCCGGCAACAACGTGATCGAGGACAGCAGGGACAACATCAGCGTGG

ACTGCAAGCAGACCCAGCTGTGCATCGTGGGCTGCGCCCCCGCCCTGGGCGAGCACTGGACC

AAGGGCGCCGTGTGCAAGAGCACCCCCGGCAACACCGGCGACTGCCCCCCCCTGGCCCTGGT

GAACACCCCCATCGAGGACGGCGACATGGTGGACACCGGCTTCGGCGCCATGGACTTCAAGC

TGCTGCAGGAGAGCAAGGCCGAGGTGCCCCTGGACATCGTGCAGAGCACCTGCAAGTACCC

CGACTACCTGAAGATGAGCGCCGACGCCTACGGCGACAGCATGTGGTTCTACCTGAGGAGGG

AGCAGCTGTTCGCCAGGCACTACTTCAACAGGGCCGGCAACGTGGGCGAGGCCATCCCCACC

GACCTGTACTGGAAGGGCGGCAACGGCAGGGACCCCCCCCCCAGCAGCGTGTACGTGGCCA

CCCCCAGCGGCAGCATGATCACCAGCGAGGCCCAGCTGTTCAACAAGCCCTACTGGCTGCAG

AGGGCCCAGGGCCACAACAACGGCATCTGCTGGGGCAACCAGGTGTTCGTGACCGTGGTGG

ACACCACCAGGAGCACCAACATGACCATCAACGCCGCCAAGAGCACCCTGACCAAGTACGA

CGCCAGGGAGATCAACCAGTACCTGAGGCACGTGGAGGAGTACGAGCTGCAGTTCGTGTTCC

AGCTGTGCAAGATCACCCTGACCGCCGAGGTGATGGCCTACCTGCACAACATGAACAACACC

CTGCTGGACGACTGGAACATCGGCCTGAGCCCCCCCGTGGCCACCAGCCTGGAGGACAAGTA

CAGGTACATCAAGAGCACCGCCATCACCTGCCAGAGGGAGCAGCCCCCCGCCGAGAAGCAG

GACCCCCTGGCCAAGTACAAGTTCTGGGAGGTGAACCTGCAGGACAGCTTCAGCGCCGACCT

GGACCAGTTCCCCCTGGGCAGGAAGTTCCTGATGCAGCTGGGCCCCAGGCCCCCCAGGCCCA

AGGCCAGCGTGAGCGCCAGCAAGAGGAGGGCCGCCCCCACCAGCAGCAGCAGCAGCCCCGC

CAAGAGGAAGAAGTAA

Sequence 16 (SEQ ID NO: 16):
ATGCCCAGCGACAACAAGGTGTACCTGCCCCCCACCCCCGTGAGCAAGGTGGTGGCCACCGA

CACCTACGTGAAGAGGACCAGCATCTTCTACCACGCCGGCAGCAGCAGGCTGCTGGCCGTGG

GCCACCCCTACTACAGCGTGAGCAAGAGCGGCACCAAGACCAACATCCCCAAGGTGAGCGC

CTACCAGTACAGGGTGTTCAGGGTGAGGCTCCCCGACCCCAACAAGTTCGGCCTGCCCGACC

CCAGCTTCTACAACCCCGACCAGGAGAGGCTGGTGTGGGCCTGCGTGGGCCTGGAGGTGGGC

AGAGGCCAGCCTCTGGGAGCTGGCCTGAGCGGCCACCCCCTGTTCAACCGGCTGGACGACAC

CGAGAGCAGCAACCTGGCCAACAACAACGTGATCGAGGACAGCCGGGACAACATCAGCGTG

GACGGCAAGCAGACCCAGCTGTGCATCGTGGGCTGCGCCCCCGCCCTGGGCGAGCACTGGAC

CAAGGGCGCCGTGTGCAAGAGCACCCCCGGCAACACCGGCGACTGCCCCCCCCTGGCCCTGG

TGAACACCCCCATCGAGGACGGCGACATGGTGGACACCGGCTTCGGCGCCATGGACTTCAAG

CTGCTGCAGGAGAGCAAGGCCGAGGTGCCCCTGGACATCGTGCAGAGCACCTGCAAGTACCC

CGACTACCTGAAGATGAGCGCCGACGCCTACGGCGACAGCATGTGGTTCTACCTGAGGAGG

GAGCAGCTGTTCGCCAGGCACTACTTCAACAGGGCCGGCAACGTGGGCGAGGCCATCCCCAC

CGACCTGTACTGGAAGGGCGGCAACGGCAGGGACCCCCCCCCCAGCAGCGTGTACGTGGCC

ACCCCCAGCGGCAGCATGATCACCAGCGAGGCCCAGCTGTTCAACAAGCCCTACTGGCTGCA

GAGGGCCCAGGGCCACAACAACGGCATCTGCTGGGGCAACCAGGTGTTCGTGACCGTGGTG

GACACCACCAGGAGCACCAACATGACCATCAACGCCGCCAAGAGCACCCTGACCAAGTACG
```

ACGCCAGGGAGATCAACCAGTACCTGAGGCACGTGGAGGAGTACGAGCTGCAGTTCGTGTTC
CAGCTGTGCAAGATCACCCTGACCGCCGAGGTGATGGCCTACCTGCACAACATGAACAACAC
CCTGCTGGACGACTGGAACATCGGCCTGAGCCCCCCGTGGCCACCAGCCTGGAGGACAAGT
ACAGGTACATCAAGAGCACCGCCATCACCTGCCAGAGGGAGCAGCCCCCGCCGAGAAGCA
GGACCCCCTGGCCAAGTACAAGTTCTGGGAGGTGAACCTGCAGGACAGCTTCAGCGCCGACC
TGGACCAGTTCCCCCTGGGCAGGAAGTTCCTGATGCAGCTGGGCCCCAGGCCCCCCAGGCCC
AAGGCCAGCGTGAGCGCCAGCAAGAGGAGGGCCGCCCCCACCAGCAGCAGCAGCAGCCCCG
CCAAGAGGAAGAAGTAA

Sequence 17 (SEQ ID NO: 17):
ATGCCCAGCGACAACAAGGTGTACCTGCCCCCCACCCCCGTGAGCAAGGTGGTGGCCACCGA
CACCTACGTGAAGAGGACCAGCATCTTCTACCACGCCGGCAGCAGCAGGCTGCTGGCCGTGG
GCCACCCCTACTACAGCGTGAGCAAGAGCGGCACCAAGACCAACATCCCCAAGGTGAGCGC
CTACCAGTACAGGGTGTTCAGGGTGAGGCTCCCCGACCCCAACAAGTTCGGCCTGCCCGACC
CCAGCTTCTACAACCCCGACCAGGAGAGGCTGGTGTGGGCCTGCGTGGGCCTGGAGGTGGGC
AGGGGCCAGCCCCTGGGCGCCGGCCTGAGCGGCCACCCCCTGTTCAACAGGCTGGACGACAC
CGAGGTGAGCAACCTGGCCGGCAACAACGTGATCGAGGACAGCAGGGACAACATCAGCGTG
GACTGCAAGCAGACCCAGCTGTGCATCGTGGGCTGCGCCCCCGCCCTGGGCGAGCACTGGAC
CAAGGGCGCCGTGTGCAAGAGCACCCAGGTCACCACCGGCGACTGCCCCCCTCTGGCCCTGG
TGAACACCCCCATCGAGGACGGCGACATGGTGGACACCGGCTTCGGCGCCATGGACTTCAAG
CTGCTGCAGGAGAGCAAGGCCGAGGTGCCCCTGGACATCGTGCAGAGCACCTGCAAGTACC
CCGACTACCTGAAGATGAGCGCCGACGCCTACGGCGACAGCATGTGGTTCTACCTGAGGAGG
GAGCAGCTGTTCGCCAGGCACTACTTCAACAGGGCCGGCAACGTGGGCGAGGCCATCCCCAC
CGACCTGTACTGGAAGGGCGGCAACGGCAGGGACCCCCCCCCCAGCAGCGTGTACGTGGCC
ACCCCCAGCGGCAGCATGATCACCAGCGAGGCCCAGCTGTTCAACAAGCCCTACTGGCTGCA
GAGGGCCCAGGGCCACAACAACGGCATCTGCTGGGGCAACCAGGTGTTCGTGACCGTGGTG
GACACCACCAGGAGCACCAACATGACCATCAACGCCGCCAAGAGCACCCTGACCAAGTACG
ACGCCAGGGAGATCAACCAGTACCTGAGGCACGTGGAGGAGTACGAGCTGCAGTTCGTGTTC
CAGCTGTGCAAGATCACCCTGACCGCCGAGGTGATGGCCTACCTGCACAACATGAACAACAC
CCTGCTGGACGACTGGAACATCGGCCTGAGCCCCCCGTGGCCACCAGCCTGGAGGACAAGT
ACAGGTACATCAAGAGCACCGCCATCACCTGCCAGAGGGAGCAGCCCCCGCCGAGAAGCA
GGACCCCCTGGCCAAGTACAAGTTCTGGGAGGTGAACCTGCAGGACAGCTTCAGCGCCGACC
TGGACCAGTTCCCCCTGGGCAGGAAGTTCCTGATGCAGCTGGGCCCCAGGCCCCCCAGGCCC
AAGGCCAGCGTGAGCGCCAGCAAGAGGAGGGCCGCCCCCACCAGCAGCAGCAGCAGCCCCG
CCAAGAGGAAGAAGTAA Sequence 18 (SEQ ID NO: 18):
ATGCCCAGCGACAACAAGGTGTACCTGCCCCCCACCCCCGTGAGCAAGGTGGTGGCCACCGA
CACCTACGTGAAGAGGACCAGCATCTTCTACCACGCCGGCAGCAGCAGGCTGCTGGCCGTGG
GCCACCCCTACTACAGCGTGAGCAAGAGCGGCACCAAGACCAACATCCCCAAGGTGAGCGC
CTACCAGTACAGGGTGTTCAGGGTGAGGCTCCCCGACCCCAACAAGTTCGGCCTGCCCGACC
CCAGCTTCTACAACCCCGACCAGGAGAGGCTGGTGTGGGCCTGCGTGGGCCTGGAGGTGGGC
AGGGGCCAGCCCCTGGGCGCCGGCCTGAGCGGCCACCCCCTGTTCAACAGGCTGGACGACAC

```
CGAGGTGAGCAACCTGGCCGGCAACAACGTGATCGAGGACAGCAGGGACAACATCAGCGTG

GACTGCAAGCAGACCCAGCTGTGCATCGTGGGCTGCGCCCCCGCCCTGGGCGAGCACTGGAC

CAAGGGCGCCGTGTGCAAGAGCACCCCCGGCAACACCGGCGACTGCCCCCCCCTGGCCCTGG

TGAACACCCCCATCGAGGACGGCGACATGGTGGACACCGGCTTCGGCGCCATGGACTTCAAG

CTGCTGCAGGAGAGCAAGGCCGAGGTGCCCCTGGACATCGTGCAGAGCACCTGCAAGTACC

CCGACTACCTGAAGATGAGCGCCGACGCCTACGGCGACAGCATGTGGTTCTACCTGAGGAGG

GAGCAGCTGTTCGCCAGGCACTACTTCAACAGAGCCGGCAAAGTGGGCGAGACAATCCCCG

CCGAGCTGTACCTGAAGGGCAGCAACGGACGGGAGCCTCCTCCCAGCAGCGTGTACGTGGCC

ACCCCCAGCGGCAGCATGATCACCAGCGAGGCCCAGCTGTTCAACAAGCCCTACTGGCTGCA

GAGGGCCCAGGGCCACAACAACGGCATCTGCTGGGGCAACCAGGTGTTCGTGACCGTGGTG

GACACCACCAGGAGCACCAACATGACCATCAACGCCGCCAAGAGCACCCTGACCAAGTACG

ACGCCAGGGAGATCAACCAGTACCTGAGGCACGTGGAGGAGTACGAGCTGCAGTTCGTGTTC

CAGCTGTGCAAGATCACCCTGACCGCCGAGGTGATGGCCTACCTGCACAACATGAACAACAC

CCTGCTGGACGACTGGAACATCGGCCTGAGCCCCCCCGTGGCCACCAGCCTGGAGGACAAGT

ACAGGTACATCAAGAGCACCGCCATCACCTGCCAGAGGGAGCAGCCCCCCGCCGAGAAGCA

GGACCCCCTGGCCAAGTACAAGTTCTGGGAGGTGAACCTGCAGGACAGCTTCAGCGCCGACC

TGGACCAGTTCCCCCTGGGCAGGAAGTTCCTGATGCAGCTGGGCCCCAGGCCCCCCAGGCCC

AAGGCCAGCGTGAGCGCCAGCAAGAGGAGGGCCGCCCCCACCAGCAGCAGCAGCAGCCCCG

CCAAGAGGAAGAAGTAA

Sequence 19 (SEQ ID NO: 19):
ATGCCCAGCGACAACAAGGTGTACCTGCCCCCCACCCCCGTGAGCAAGGTGGTGGCCACCGA

CACCTACGTGAAGAGGACCAGCATCTTCTACCACGCCGGCAGCAGCAGGCTGCTGGCCGTGG

GCCACCCCTACTACAGCGTGAGCAAGAGCGGCACCAAGACCAACATCCCCAAGGTGAGCGC

CTACCAGTACAGGGTGTTCAGGGTGAGGCTCCCCGACCCCAACAAGTTCGGCCTGCCCGACC

CCAGCTTCTACAACCCCGACCAGGAGAGGCTGGTGTGGGCCTGCGTGGGCCTGGAGGTGGGC

AGGGGCCAGCCCCTGGGCGCCGGCCTGAGCGGCCACCCCCTGTTCAACAGGCTGGACGACAC

CGAGGTGAGCAACCTGGCCGGCAACAACGTGATCGAGGACAGCAGGGACAACATCAGCGTG

GACTGCAAGCAGACCCAGCTGTGCATCGTGGGCTGCGCCCCCGCCCTGGGCGAGCACTGGAC

CAAGGGCGCCGTGTGCAAGAGCACCCCCGGCAACACCGGCGACTGCCCCCCCCTGGCCCTGG

TGAACACCCCCATCGAGGACGGCGACATGGTGGACACCGGCTTCGGCGCCATGGACTTCAAG

CTGCTGCAGGAGAGCAAGGCCGAGGTGCCCCTGGACATCGTGCAGAGCACCTGCAAGTACC

CCGACTACCTGAAGATGAGCGCCGACGCCTACGGCGACAGCATGTGGTTCTACCTGAGGAGG

GAGCAGCTGTTCGCCAGGCACTACTTCAACAGGGCCGGCAACGTGGGCGAGGCCATCCCCAC

CGACCTGTACTGGAAGGGCGGCAACGGCAGGGACCCCCCCCCCAGCAGCGTGTACGTGGCC

ACCCCCAGCGGCAGCATGATCACCAGCGAGGCCCAGCTGTTCAACAAGCCCTACTGGCTGCA

GAGGGCCCAGGGCCACAACAACGGCATCTGCTGGGGCAACCAGGTGTTCGTGACCGTGGTG

GACACCACCAGGAGCACCAACATGACCATCAACGCCGCCACCGAGCAGCTGTCCAAGTACG

ACGCCCGGAAGATCAACCAGTACCTGAGGCACGTGGAGGAGTACGAGCTGCAGTTCGTGTTC

CAGCTGTGCAAGATCACCCTGACCGCCGAGGTGATGGCCTACCTGCACAACATGAACAACAC

CCTGCTGGACGACTGGAACATCGGCCTGAGCCCCCCCGTGGCCACCAGCCTGGAGGACAAGT

ACAGGTACATCAAGAGCACCGCCATCACCTGCCAGAGGGAGCAGCCCCCCGCCGAGAAGCA
```

```
GGACCCCCTGGCCAAGTACAAGTTCTGGGAGGTGAACCTGCAGGACAGCTTCAGCGCCGACC

TGGACCAGTTCCCCCTGGGCAGGAAGTTCCTGATGCAGCTGGGCCCCAGGCCCCCCAGGCCC

AAGGCCAGCGTGAGCGCCAGCAAGAGGAGGGCCGCCCCCACCAGCAGCAGCAGCAGCCCCG

CCAAGAGGAAGAAGTAA

Sequence 20 (SEQ ID NO: 20):
ATGCCCAGCGACAACAAGGTGTACCTGCCCCCCACCCCCGTGAGCAAGGTGGTGGCCACCGA

CACCTACGTGAAGAGGACCAGCATCTTCTACCACGCCGGCAGCAGCAGGCTGCTGGCCGTGG

GCCACCCCTACTACCCCATCAGCAAGAGCGGCAAGGCCGACATCCCCAAGGTGAGCGCCTAC

CAGTACAGGGTGTTCAGGGTGAGGCTCCCCGACCCCAACAAGTTCGGCCTGCCCGACCCCAG

CTTCTACAACCCCGACCAGGAGAGGCTGGTGTGGGCCTGCGTGGGCCTGGAGGTGGGCAGG

GGCCAGCCCCTGGGCGCCGGCCTGAGCGGCCACCCCCTGTTCAACAGGCTGGACGACACCGA

GGTGAGCAACCTGGCCGGCAACAACGTGATCGAGGACAGCAGGGACAACATCAGCGTGGAC

TGCAAGCAGACCCAGCTGTGCATCGTGGGCTGCGCCCCCGCCCTGGGCGAGCACTGGACCAA

GGGCGCCGTGTGCAAGAGCACCCCCGGCAACACCGGCGACTGCCCCCCCCTGGCCCTGGTGA

ACACCCCCATCGAGGACGGCGACATGGTGGACACCGGCTTCGGCGCCATGGACTTCAAGCTG

CTGCAGGAGAGCAAGGCCGAGGTGCCCCTGGACATCGTGCAGAGCACCTGCAAGTACCCCG

ACTACCTGAAGATGAGCGCCGACGCCTACGGCGACAGCATGTGGTTCTACCTGAGGAGGGA

GCAGCTGTTCGCCAGGCACTACTTCAACAGGGCCGGCAACGTGGGCGAGGCCATCCCCACCG

ACCTGTACTGGAAGGGCGGCAACGGCAGGGACCCCCCCCCCAGCAGCGTGTACGTGGCCAC

CCCCAGCGGCAGCATGATCACCAGCGAGGCCCAGCTGTTCAACAAGCCCTACTGGCTGCAGA

GGGCCCAGGGCCACAACAACGGCATCTGCTGGGGCAACCAGGTGTTCGTGACCGTGGTGGA

CACCACCAGGAGCACCAACATGACCATCAACGCCGCCACCGAGCAGCTGTCCAAGTACGAC

GCCCGGAAGATCAACCAGTACCTGAGGCACGTGGAGGAGTACGAGCTGCAGTTCGTGTTCCA

GCTGTGCAAGATCACCCTGACCGCCGAGGTGATGGCCTACCTGCACAACATGAACAACACCC

TGCTGGACGACTGGAACATCGGCCTGAGCCCCCCCGTGGCCACCAGCCTGGAGGACAAGTAC

AGGTACATCAAGAGCACCGCCATCACCTGCCAGAGGGAGCAGCCCCCGCCGAGAAGCAGG

ACCCCCTGGCCAAGTACAAGTTCTGGGAGGTGAACCTGCAGGACAGCTTCAGCGCCGACCTG

GACCAGTTCCCCCTGGGCAGGAAGTTCCTGATGCAGCTGGGCCCCAGGCCCCCCAGGCCCAA

GGCCAGCGTGAGCGCCAGCAAGAGGAGGGCCGCCCCCACCAGCAGCAGCAGCAGCCCCGCC

AAGAGGAAGAAGTAA

Sequence 21 (SEQ ID NO: 21):
ATGCCCAGCGACAACAAGGTGTACCTGCCCCCCACCCCCGTGAGCAAGGTGGTGGCCACCGA

CACCTACGTGAAGAGGACCAGCATCTTCTACCACGCCGGCAGCAGCAGGCTGCTGGCCGTGG

GCCACCCCTACTACAGCGTGAGCAAGAGCGGCACCAAGACCAACATCCCCAAGGTGAGCGC

CTACCAGTACAGGGTGTTCAGGGTGAGGCTCCCCGACCCCAACAAGTTCGGCCTGCCCGACC

CCAGCTTCTACAACCCCGACCAGGAGAGGCTGGTGTGGGCCTGCGTGGGCCTGGAGGTGGGC

AGGGGCCAGCCCCTGGGCGTGGGCGTGAGCGGCCACCCCCTGTTCAACAGGCTGGACGACA

CCGAGAGCAGCAGCATCGCCATCCAGGACACCGCCCCCGACAGCAGGGACAACGTGAGCGT

GGACCCCAAGCAGACCCAGCTGTGCATCGTGGGCTGCGCCCCCGCCCTGGGCGAGCACTGGA

CCAAGGGCGCCGTGTGCAAGAGCACCCCCGGCAACACCGGCGACTGCCCCCCCCTGGCCCTG

GTGAACACCCCCATCGAGGACGGCGACATGGTGGACACCGGCTTCGGCGCCATGGACTTCAA

GCTGCTGCAGGAGAGCAAGGCCGAGGTGCCCCTGGACATCGTGCAGAGCACCTGCAAGTAC
```

-continued

CCCGACTACCTGAAGATGAGCGCCGACGCCTACGGCGACAGCATGTGGTTCTACCTGAGGAG
GGAGCAGCTGTTCGCCAGGCACTACTTCAACAGGGCCGGCAACGTGGGCGAGGCCATCCCCA
CCGACCTGTACTGGAAGGGCGGCAACGGCAGGGACCCCCCCCCCAGCAGCGTGTACGTGGC
CACCCCCAGCGGCAGCATGATCACCAGCGAGGCCCAGCTGTTCAACAAGCCCTACTGGCTGC
AGAGGGCCCAGGGCCACAACAACGGCATCTGCTGGGGCAACCAGGTGTTCGTGACCGTGGT
GGACACCACCAGGAGCACCAACATGACCATCAACGCCGCCACCGAGCAGCTGTCCAAGTAC
GACGCCCGGAAGATCAACCAGTACCTGAGGCACGTGGAGGAGTACGAGCTGCAGTTCGTGTT
CCAGCTGTGCAAGATCACCCTGACCGCCGAGGTGATGGCCTACCTGCACAACATGAACAACA
CCCTGCTGGACGACTGGAACATCGGCCTGAGCCCCCCCGTGGCCACCAGCCTGGAGGACAAG
TACAGGTACATCAAGAGCACCGCCATCACCTGCCAGAGGGAGCAGCCCCCCGCCGAGAAGC
AGGACCCCCTGGCCAAGTACAAGTTCTGGGAGGTGAACCTGCAGGACAGCTTCAGCGCCGAC
CTGGACCAGTTCCCCCTGGGCAGGAAGTTCCTGATGCAGCTGGGCCCCAGGCCCCCCAGGCC
CAAGGCCAGCGTGAGCGCCAGCAAGAGGAGGGCCGCCCCCACCAGCAGCAGCAGCAGCCCC
GCCAAGAGGAAGAAGTAA

Sequence 22 (SEQ ID NO: 22):
ATGCCCAGCGACAACAAGGTGTACCTGCCCCCCACCCCCGTGAGCAAGGTGGTGGCCACCGA
CACCTACGTGAAGAGGACCAGCATCTTCTACCACGCCGGCAGCAGCAGGCTGCTGGCCGTGG
GCCACCCCTACTACAGCGTGAGCAAGAGCGGCACCAAGACCAACATCCCCAAGGTGAGCGC
CTACCAGTACAGGGTGTTCAGGGTGAGGCTCCCCGACCCCAACAAGTTCGGCCTGCCCGACC
CCAGCTTCTACAACCCCGACCAGGAGAGGCTGGTGTGGGCCTGCGTGGGCCTGGAGGTGGGC
AGGGGCCAGCCCCTGGGCGCCGGCCTGAGCGGCCACCCCCTGTTCAACAGGCTGGACGACAC
CGAGGTGAGCAACCTGGCCGGCAACAACGTGATCGAGGACAGCAGGGACAACATCAGCGTG
GACTGCAAGCAGACCCAGCTGTGCATCGTGGGCTGCGCCCCCGCCCTGGGCGAGCACTGGAC
CAAGGGCGCCGTGTGCAAGAGCACCCCCGGCAACACCGGCGACTGCCCCCCCCTGGCCCTGG
TGAACACCCCCATCGAGGACGGCGACATGGTGGACACCGGCTTCGGCGCCATGGACTTCAAG
CTGCTGCAGGAGAGCAAGGCCGAGGTGCCCCTGGACATCGTGCAGAGCACCTGCAAGTACC
CCGACTACCTGAAGATGAGCGCCGACGCCTACGGCGACAGCATGTGGTTCTACCTGAGGAGG
GAGCAGCTGTTCGCCAGGCACTTCTTCAACAGGGCCGGCGTGATCGGCGAGGAGATCCCCAA
CGACCTGTACATCAAGGGCAGCAACGGCAGGGACCCCCCCCCCAGCAGCGTGTACGTGGCC
ACCCCCAGCGGCAGCATGATCACCAGCGAGGCCCAGCTGTTCAACAAGCCCTACTGGCTGCA
GAGGGCCCAGGGCCACAACAACGGCATCTGCTGGGGCAACCAGGTGTTCGTGACCGTGGTG
GACACCACCAGGAGCACCAACATGACCATCAACGCCGCCACCGAGCAGCTGTCCAAGTACG
ACGCCCGGAAGATCAACCAGTACCTGAGGCACGTGGAGGAGTACGAGCTGCAGTTCGTGTTC
CAGCTGTGCAAGATCACCCTGACCGCCGAGGTGATGGCCTACCTGCACAACATGAACAACAC
CCTGCTGGACGACTGGAACATCGGCCTGAGCCCCCCCGTGGCCACCAGCCTGGAGGACAAGT
ACAGGTACATCAAGAGCACCGCCATCACCTGCCAGAGGGAGCAGCCCCCCGCCGAGAAGCA
GGACCCCCTGGCCAAGTACAAGTTCTGGGAGGTGAACCTGCAGGACAGCTTCAGCGCCGACC
TGGACCAGTTCCCCCTGGGCAGGAAGTTCCTGATGCAGCTGGGCCCCAGGCCCCCCAGGCCC
AAGGCCAGCGTGAGCGCCAGCAAGAGGAGGGCCGCCCCCACCAGCAGCAGCAGCAGCCCCG
CCAAGAGGAAGAAGTAA Sequence 23 (SEQ ID NO: 23):
TEQLSKYDARK Sequence 24 (SEQ ID NO: 24):
PISKSGKAD Sequence 25 (SEQ ID NO: 25):
VGVSGHPLFNRLDDTESSSIAIQDTAPDSRDNVSVDP Sequence 26 (SEQ ID NO: 26):
FFNRAGVIGEEIPNDLYIKGSNGRD Sequence 27 (SEQ ID NO: 27):
TKDN Sequence 28 (SEQ ID NO: 28):
MPSDNKVYLPPTPVSKVVATDTYVKRTSIFYHAGSSRLLAVGHPYYSVSKSGTKTNIPKVSAYQYRVF
RVRLPDPNKFGLPDPSFYNPDQERLVWACVGLEVGRGQPLGAGLSGHPLFNRLDDTEVSNLAGNNVI
EDSRDNISVDCKQTQLCIVGCAPALGEHWTKGAVCKSTPGNTGDCPPLALVNTPIEDGDMVDTGFGA
MDFKLLQESKAEVPLDIVQSTCKYPDYLKMSADAYGDSMWFYLRREQLFARHYFNRAGNVGEAIPT
DLYWKGGNGRDPPPSSVYVATPSGSMITSEAQLFNKPYWLQRAQGHNNGICWGNQVFVTVVDTTRS
TNMTINAAKSTLTKYDAREINQYLRHVEEYELQFVFQLCKITLTAEVMAYLHNMNNTLLDDWNIGLS
PPVATSLEDKYRYIKSTAITCQREQPPAEKQDPLAKYKFWEVNLQDSFSADLDQFPLGRKFLMQLGPR
PPRPKASVSASKRRAAPTSSSSSPAKRKK Sequence 29 (SEQ ID NO: 29):
ATGCCCAGCGACAACAAGGTGTACCTGCCCCCCACCCCCGTGAGCAAGGTGGTGGCCACCGA
CACCTACGTGAAGAGGACCAGCATCTTCTACCACGCCGGCAGCAGCAGGCTGCTGGCCGTGG
GCCACCCCTACTACAGCGTGAGCAAGAGCGGCACCAAGACCAACATCCCCAAGGTGAGCGC
CTACCAGTACAGGGTGTTCAGGGTGAGGCTCCCCGACCCCAACAAGTTCGGCCTGCCCGACC
CCAGCTTCTACAACCCCGACCAGGAGAGGCTGGTGTGGGCCTGCGTGGGCCTGGAGGTGGGC
AGGGGCCAGCCCCTGGGCGCCGGCCTGAGCGGCCACCCCCTGTTCAACAGGCTGGACGACAC
CGAGGTGAGCAACCTGGCCGGCAACAACGTGATCGAGGACAGCAGGGACAACATCAGCGTG
GACTGCAAGCAGACCCAGCTGTGCATCGTGGGCTGCGCCCCCGCCCTGGGCGAGCACTGGAC
CAAGGGCGCCGTGTGCAAGAGCACCCCCGGCAACACCGGCGACTGCCCCCCCCTGGCCCTGG
TGAACACCCCCATCGAGGACGGCGACATGGTGGACACCGGCTTCGGCGCCATGGACTTCAAG
CTGCTGCAGGAGAGCAAGGCCGAGGTGCCCCTGGACATCGTGCAGAGCACCTGCAAGTACC
CCGACTACCTGAAGATGAGCGCCGACGCCTACGGCGACAGCATGTGGTTCTACCTGAGGAGG
GAGCAGCTGTTCGCCAGGCACTACTTCAACAGGGCCGGCAACGTGGGCGAGGCCATCCCCAC
CGACCTGTACTGGAAGGGCGGCAACGGCAGGGACCCCCCCCCCAGCAGCGTGTACGTGGCC
ACCCCCAGCGGCAGCATGATCACCAGCGAGGCCCAGCTGTTCAACAAGCCCTACTGGCTGCA
GAGGGCCCAGGGCCACAACAACGGCATCTGCTGGGGCAACCAGGTGTTCGTGACCGTGGTG
GACACCACCAGGAGCACCAACATGACCATCAACGCCGCCAAGAGCACCCTGACCAAGTACG
ACGCCAGGGAGATCAACCAGTACCTGAGGCACGTGGAGGAGTACGAGCTGCAGTTCGTGTTC
CAGCTGTGCAAGATCACCCTGACCGCCGAGGTGATGGCCTACCTGCACAACATGAACAACAC
CCTGCTGGACGACTGGAACATCGGCCTGAGCCCCCCCGTGGCCACCAGCCTGGAGGACAAGT
ACAGGTACATCAAGAGCACCGCCATCACCTGCCAGAGGGAGCAGCCCCCGCCGAGAAGCA
GGACCCCCTGGCCAAGTACAAGTTCTGGGAGGTGAACCTGCAGGACAGCTTCAGCGCCGACC -continued

```
TGGACCAGTTCCCCCTGGGCAGGAAGTTCCTGATGCAGCTGGGCCCCAGGCCCCCCAGGCCC

AAGGCCAGCGTGAGCGCCAGCAAGAGGAGGGCCGCCCCCACCAGCAGCAGCAGCAGCCCCG

CCAAGAGGAAGAAGTAA
```

Sequence 30 (SEQ ID NO: 30):
QVT

Sequence 31 (SEQ ID NO: 31):
```
MPSDSKVYLPPTPVSKVITTDAYVKRTTIFYHAGSSRLLTVGHPYYPISKSGKADIPKVSAFQYRVFRV

RLPDPNKFGLPDTNIFNPDQERLVWACVGLEIGRGQPLGVGVSGHPLFNRLDDTESSSIAIQDTAPDSR

DNVSVDPKQTQLCIIGCAPAIGEHWTKGTACRSTPTTAGDCPPLELINSPIEDGDMVDTGFGALNFKAL

QESKSDVPLDIVQSTCKYPDYLKMSADAYGDSMWFYLRREQLFTRHFFNRAGVIGEEIPNDLYIKGSN

GRDPPPSSVYVATPSGSMITSEAQLFNKPYWLQRAQGHNNGICWNNQLFVTVVDTTRNTNMTLSATT

QSMSTYNSKQIKQYVRHAEEYELQFVFQLCKISLSAEVMAYLHTMNSTLLEDWNIGLSPPVATSLED

KYRYVKSAAITCQKDQPPPEKQDPLSKYKFWEVNLQNSFSADLDQFPLGRKFLMQVGVRTKPPVSSK

KRSASTTSTSAPSSKRKRK
```

Sequence 32 (SEQ ID NO: 32):
```
ATGCCCAGCGACAGCAAGGTGTACCTGCCCCCCACCCCCGTGAGCAAGGTGATCACCACCGACG

CCTACGTGAAGAGGACCACCATCTTCTACCACGCCGGCAGCAGCAGGCTGCTGACCGTGGGCCA

CCCCTACTACCCCATCAGCAAGAGCGGCAAGGCCGACATCCCCAAGGTGAGCGCCTTCCAGTAC

AGGGTGTTCAGGGTGAGGCTGCCCGACCCCAACAAGTTCGGCCTGCCCGACACCAACATCTTCAA

CCCCGACCAGGAGAGGCTGGTGTGGGCCTGCGTGGGCCTGGAGATCGGCAGGGGCCAGCCCCTG

GGCGTGGGCGTGAGCGGCCACCCCCTGTTCAACAGGCTGGACGACACCGAGAGCAGCAGCATCG

CCATCCAGGACACCGCCCCCGACAGCAGGGACAACGTGAGCGTGGACCCCAAGCAGACCCAGCT

GTGCATCATCGGCTGCGCCCCCGCCATCGGCGAGCACTGGACCAAGGGCACCGCCTGCAGGAGC

ACCCCCACCACCGCCGGCGACTGCCCCCCCCTGGAGCTGATCAACAGCCCCATCGAGGACGGCG

ACATGGTGGACACCGGCTTCGGCGCCCTGAACTTCAAGGCCCTGCAGGAGAGCAAGAGCGACGT

GCCCCTGGACATCGTGCAGAGCACCTGCAAGTACCCCGACTACCTGAAGATGAGCGCCGACGCC

TACGGCGACAGCATGTGGTTCTACCTGAGGAGGGAGCAGCTGTTCACCAGGCACTTCTTCAACAG

GGCCGGCGTGATCGGCGAGGAGATCCCCAACGACCTGTACATCAAGGGCAGCAACGGCAGGGAC

CCCCCCCCCAGCAGCGTGTACGTGGCCACCCCCAGCGGCAGCATGATCACCAGCGAGGCCCAGC

TGTTCAACAAGCCCTACTGGCTGCAGAGGGCCCAGGGCCACAACAACGGCATCTGCTGGAACAA

CCAGCTGTTCGTGACCGTGGTGGACACCACCAGGAACACCAACATGACCCTGAGCGCCACCACC

CAGAGCATGAGCACCTACAACAGCAAGCAGATCAAGCAGTACGTGAGGCACGCCGAGGAGTAC

GAGCTGCAGTTCGTGTTCCAGCTGTGCAAGATCAGCCTGAGCGCCGAGGTGATGGCCTACCTGCA

CACCATGAACAGCACCCTGCTGGAGGACTGGAACATCGGCCTGAGCCCCCCCGTGGCCACCAGC

CTGGAGGACAAGTACAGGTACGTGAAGAGCGCCGCCATCACCTGCCAGAAGGACCAGCCCCCCC

CCGAGAAGCAGGACCCCCTGAGCAAGTACAAGTTCTGGGAGGTGAACCTGCAGAACAGCTTCAG

CGCCGACCTGGACCAGTTCCCCCTGGGCAGGAAGTTCCTGATGCAGGTGGGCGTGAGGACCAAG

CCCCCCGTGAGCAGCAAGAAGAGGAGCGCCAGCACCACCAGCACCAGCGCCCCCAGCAGCAAG

AGGAAGAGGAAGTAA
```

Sequence 33 (SEQ ID NO: 33):
SSNLANNNVIEDSRDNISVDG

Sequence 34 (SEQ ID NO: 34):
KVGETIPAELYLKGSNGRE

Sequence 63 (SEQ ID NO: 63):
MAMWRPSDNKVYLPPTPVSKVVATDTYVKRTSIFYHAGSSRLLAVGHPYYSVSKSGTKTNIPKVSAY

QYRVFRVRLPDPNKFGLPDPSFYNPDQERLVWACVGLEVGRGQPLGVGVSGHPLFNRLDDTESSSIAI

QDTAPDSRDNVSVDPKQTQLCIVGCAPALGEHWTKGTACRSTPTTAGDCPPLALVNTPIEDGDMVDT

GFGAMDFKLLQESKAEVPLDIVQSTCKYPDYLKMSADAYGDSMWFYLRREQLFARHYFNRAGNVG

EAIPTDLYWKGGNGRDPPPSSVYVATPSGSMITSEAQLFNKPYWLQRAQGHNNGICWGNQVFVTVV

DTTRSTNMTINAATINQYLRHVEEYELQFVFQLCKITLTAEVMAYLHNMNNTLLDDWNIGLSPPVAT

SLEDKYRYIKSTAITCQREQPPAEKQDPLAKYKFWEVNLQDSFSADLDQFPLGRKFLMQLGPRPPRPK

ASVSASKRRAAPTSSSSSPAKRKK.

Sequence 64 (SEQ ID NO: 64):
ATGGCCATGTGGAGGCCCAGCGACAACAAGGTGTACCTGCCCCCCACCCCCGTGAGCAAGGTGG

TGGCCACCGACACCTACGTGAAGAGGACCAGCATCTTCTACCACGCCGGCAGCAGCAGGCTGCT

GGCCGTGGGCCACCCCTACTACAGCGTGAGCAAGAGCGGCACCAAGACCAACATCCCCAAGGTG

AGCGCCTACCAGTACAGGGTGTTCAGGGTGAGGCTCCCCGACCCCAACAAGTTCGGCCTGCCCG

ACCCCAGCTTCTACAACCCCGACCAGGAGAGGCTGGTGTGGGCCTGCGTGGGCCTGGAGGTGGG

CAGGGGCCAGCCCCTGGGCGTGGGCGTGAGCGGCCACCCCCTGTTCAACAGGCTGGACGACACC

GAGAGCAGCAGCATCGCCATCCAGGACACCGCCCCCGACAGCAGGGACAACGTGAGCGTGGACC

CCAAGCAGACCCAGCTGTGCATCGTGGGCTGCGCCCCCGCCCTGGGCGAGCACTGGACCAAGGG

CACCGCCTGCAGGAGCACCCCCACCACCGCCGGCGACTGCCCCCCCCTGGCCCTGGTGAACACCC

CCATCGAGGACGGCGACATGGTGGACACCGGCTTCGGCGCCATGGACTTCAAGCTGCTGCAGGA

GAGCAAGGCCGAGGTGCCCCTGGACATCGTGCAGAGCACCTGCAAGTACCCCGACTACCTGAAG

ATGAGCGCCGACGCCTACGGCGACAGCATGTGGTTCTACCTGAGGAGGGAGCAGCTGTTCGCCA

GGCACTACTTCAACAGGGCCGGCAACGTGGGCGAGGCCATCCCCACCGACCTGTACTGGAAGGG

CGGCAACGGCAGGGACCCCCCCCCCAGCAGCGTGTACGTGGCCACCCCCAGCGGCAGCATGATC

ACCAGCGAGGCCCAGCTGTTCAACAAGCCCTACTGGCTGCAGAGGGCCCAGGGCCACAACAACG

GCATCTGCTGGGGCAACCAGGTGTTCGTGACCGTGGTGGACACCACCAGGAGCACCAACATGAC

CATCAACGCCGCCACCGAGCAGCTGTCCAAGTACGACGCCCGGAAGATCAACCAGTACCTGAGG

CACGTGGAGGAGTACGAGCTGCAGTTCGTGTTCCAGCTGTGCAAGATCACCCTGACCGCCGAGGT

GATGGCCTACCTGCACAACATGAACAACACCCTGCTGGACGACTGGAACATCGGCCTGAGCCCC

CCCGTGGCCACCAGCCTGGAGGACAAGTACAGGTACATCAAGAGCACCGCCATCACCTGCCAGA

GGGAGCAGCCCCCCGCCGAGAAGCAGGACCCCCTGGCCAAGTACAAGTTCTGGGAGGTGAACCT

GCAGGACAGCTTCAGCGCCGACCTGGACCAGTTCCCCCTGGGCAGGAAGTTCCTGATGCAGCTG

GGCCCCAGGCCCCCCAGGCCCAAGGCCAGCGTGAGCGCCAGCAAGAGGAGGGCCGCCCCCACCA

GCAGCAGCAGCAGCCCCGCCAAGAGGAAGAAGTAA

Sequence 65 (SEQ ID NO: 65):
TACRSTPTTA

Specific Modes for Carrying Out the Invention

The present invention is further described by reference to the examples as follows, wherein the examples are used only for the purpose of illustrating the present invention, rather than limiting the present invention.

Unless indicated otherwise, the molecular biological experimental methods and immunological assays used in the present invention are carried out substantially in accordance with the methods as described in J. Sambrook et al., Molecular Cloning: A Laboratory Manual (Second Edition), Cold Spring Harbor Laboratory Press, 1989, and F. M. Ausubel et al., Short Protocols in Molecular Biology, 3rd Edition, John Wiley & Sons, Inc., 1995; and restriction enzymes are used under the conditions recommended by the manufacturers. Those skilled in the art understand that the examples are used for illustrating the present invention, but not intended to limit the protection scope of the present invention.

Example 1. Expression and Purification of the Mutated HPV66 L1 Proteins

Construction of Expression Vectors

An expression vector encoding the mutated HPV66 L1 protein comprising a segment from HPV56 L1 protein was constructed by PCR for multi-site mutagenesis, wherein the initial template used was the plasmid pTO-T7-HPV66N5C (encoding the HPV66 L1 protein having 5 amino acids truncated at N-terminal; abbreviated as 66L1N5 in Table 2). The templates and primers for each PCR were shown in Table 2, and the amplification conditions for PCR were as followed: denaturation at 94° C. for 2 min; 30 cycles (denaturation at 98° C. for 10 sec, annealing at a given temperature for a certain period of time, and extension at 58° C. for 6.5 min); and final extension at 68° C. for 10 min. The temperature and time of annealing were listed in Table 2. The sequences of the PCR primers used were listed in Table 3.

To the amplification product (50 μL), 2 μL restriction endonuclease DpnI (Fermentas (MBI), Cat. No. FD1704, 2500U/tube) was added, and the resultant mixture was incubated at 37° C. for 60 min. 10 μL of the product of digestion was used to transform 40 μL competent *E. coli* ER2566 (purchased from New England Biolabs) prepared by the Calcium chloride method. The transformed *E. coli* was spread onto solid LB medium (the components of the LB medium: 10 g/L peptone, 5 g/L yeast powder, 10 g/L NaCl, the same hereinafter) containing kanamycin (at a final concentration of 25 μg/mL, the same hereinafter), and was subjected to static culture at 37° C. for 10-12 h until single colonies could be observed clearly. Single colony was picked and inoculated into a tube containing 4 mL liquid LB medium (containing kanamycin), and cultured with shaking at 220 rpm for 10 h at 37° C., and then 1 ml bacterial solution was taken and stored at −70° C. Plasmids were extracted from *E. coli*, and T7 primer was used to sequence the nucleotide sequences of the fragments of interest inserted into the plasmids. The sequencing result showed that the nucleotide sequences of the fragments of interest inserted into the constructed plasmids (expression vectors) were SEQ ID NO: 15 and 17, respectively, and their encoded amino acid sequences were SEQ ID NO: 4 and 6, respectively (the corresponding proteins were designated as H66N5-56T1 and H66N5-56T3, respectively).

The mutated protein H66N5-56T1 differs from HPV66N5 by: the substitution of the amino acid residues from positions 53-56 of wild type HPV66 L1 protein with the amino acid residues from positions 53-56 of wild type HPV56 L1 protein. The mutated protein H66N5-56T3 differs from HPV66N5 by: the substitution of the amino acid residues from positions 178-180 of wild type HPV66 L1 protein with the amino acid residues from positions 178-180 of wild type HPV56 L1 protein.

Gibson assembly (Gibson D G, Young L, Chuang R Y, Venter J C, Hutchison C A, Smith H O. Enzymatic assembly of DNA molecules up to several hundred kilobases. Nat Methods. 2009; 6:343-5. doi: 10.1038/nmeth.1318) was used to construct the expression vector encoding the other mutated HPV66 L1 protein, wherein the mutated HPV66 L1 protein comprised a specific segment from HPV56 L1 and a specific segment from HPV53L1. In brief, a short fragment comprising mutations and a long fragment comprising no mutation were obtained by PCR, and Gibson assembly system was then used to ligate the two fragments to form a ring. The initial template used comprised the plasmid pTO-T7-HPV66L1N5 (encoding the HPV66 L1 protein having 5 amino acids truncated at N-terminal; abbreviated as 66L1N5 in Table 2), the plasmid pTO-T7-HPV53N0 (encoding the full-length HPV56 L1 protein; abbreviated as 56L1N0 in Table 2), the plasmid pTO-T7-H66N5-56T5 (encoding the mutated protein H66N5-56T5; abbreviated as H66N5-56T5 in Table 2) and the plasmid pTO-T7-HPV53N5 (encoding the HPV53 L1 protein having 5 amino acids truncated at N-terminal; abbreviated as 53L1N5 in Table 2). The templates and primers for each PCR were shown in Table 2, and, the amplification conditions for PCR for amplifying the short fragment were as followed: denaturation at 94° C. for 10 min; 25 cycles (denaturation at 94° C. for 50 sec, annealing at a given temperature for a certain period of time, and extension at 72° C. for 1 min); and final extension at 72° C. for 10 min. The amplification conditions for PCR for amplifying the long fragment were as followed: denaturation at 94° C. for 10 min; 25 cycles (denaturation at 94° C. for 50 sec, annealing at a given temperature for a certain period of time, and extension at 72° C. for 7.5 min); and final extension at 72° C. for 10 min. The sequences of the PCR primers used were listed in Table 3. The amplification product was subjected to electrophoresis, the fragment of interest was then recovered by using DNA Extraction Kit (BEYOTIME, Cat. No. D0033), and its concentration was determined. The short fragment and long fragment obtained by amplification were mixed at a molar ratio of 2:1 (a total volume of 3 μL), and 3 μL of 2×Gibson Assembly Master Mix (purchased from NEB, containing T5 exonuclease, Phusion DNA polymerase, Taq DNA ligase) was then added, and reacted at 50° C. for 1 h.

The assembled product (6 μL) was used to transform 40 μL competent *E. coli* ER2566 (purchased from New England Biolabs) prepared by the Calcium chloride method. The transformed *E. coli* were spread onto solid LB medium containing kanamycin, and were subjected to static culture at 37° C. for 10-12 h until single colonies could be observed clearly. Single colony was picked and inoculated into a tube containing 4 mL liquid LB medium (containing kanamycin), and cultured with shaking at 220 rpm for 10h at 37° C., and then 1 ml bacterial solution was taken and stored at −70° C. Plasmids were extracted from *E. coli*, and T7 primer was used to sequence the nucleotide sequences of the fragments of interest inserted into the plasmids. The sequencing result showed that the nucleotide sequences of the fragments of interest inserted into the constructed plasmids (expression vectors) were SEQ ID NO: 16, 18, 19, 20, 21 and 22, respectively, and their encoded amino acid sequences were SEQ ID NO: 5, 7, 8, 9, 10 and 11, respectively (the corresponding proteins were designated as H66N5-56T2, H66N5-56T4, H66N5-56T5, H66N5-56T5-53S1, H66N5-56T5- 53S2 and H66N5-56T5-53S4, respectively).

The H66N5-56T5-53S2-53S3 gene was synthesized by Sangon Biotech (Shanghai) Co., Ltd. The synthesized plasmid comprising the HPV66N5-56T5-53S2-53S3 gene was digested with NdeI and SalI (at 37° C. for 12h). After digestion, the gene of interest was recovered by using DNA Extraction Kit (BEYOTIME, Cat. No. D0033), and the digested H66N5-56T5-53S2-53S3 gene was ligated with pTO-T7 vector at 16° C. for 12 h, and then the resultant product was used to transform competent *E. coli* ER2566 (purchased from New England Biolabs). The transformed *E. coli* were spread onto solid LB medium containing kanamycin, and were subjected to static culture at 37° C. for 10-12 h until single colonies could be observed clearly. Single colony was picked and inoculated into a tube containing 4 mL liquid LB medium (containing kanamycin), and cultured with shaking at 220 rpm for 10h at 37° C., and then 1 ml bacterial solution was taken and stored at −70° C. Plasmids were extracted from *E. coli*, and T7 primer was used to sequence the nucleotide sequences of the fragments of interest inserted into the plasmids. The sequencing result showed that the nucleotide sequences of the fragments of interest inserted into the constructed plasmids (expression vectors) was SEQ ID NO: 64, and its encoded amino acid sequences were SEQ ID NO: 63 (the corresponding proteins were designated as H66N5-56T5-53S2-53S3).

The mutated protein H66N5-56T2 differs from HPV66N5 by: the substitution of the amino acid residues from positions 130-150 of wild type HPV66 L1 protein with the amino acid residues from positions 130-150 of wild type HPV56 L1 protein. The mutated protein H66N5-56T4 differs from HPV66N5 by: the substitution of the amino acid residues from positions 265-283 of wild type HPV66 L1 protein with the amino acid residues from positions 265-283 of wild type HPV56 L1 protein. The mutated protein H66N5-56T5 differs from HPV66N5 by: the substitution of the amino acid residues from positions 347-357 of wild type HPV66 L1 protein with the amino acid residues from positions 347-357 of wild type HPV56 L1 protein.

The mutated protein H66N5-56T5-53S1 differs from HPV66N5 by: the substitution of the amino acid residues from positions 347-357 of wild type HPV66 L1 protein with the amino acid residues from positions 347-357 of wild type HPV56 L1 protein, and the substitution of the amino acid residues from positions 51-60 of wild type HPV66 L1 protein with the amino acid residues from positions 51-59 of wild type HPV53 L1 protein. The mutated protein H66N5-56T5-53S2 differs from HPV66N5 by: the substitution of the amino acid residues from positions 347-357 of wild type HPV66 L1 protein with the amino acid residues from positions 347-357 of wild type HPV56 L1 protein, and the substitution of the amino acid residues from positions 114-150 of wild type HPV66 L1 protein with the amino acid residues from positions 113-149 of wild type HPV53 L1 protein. The mutated protein H66N5-56T5-53S4 differs from HPV66N5 by: the substitution of the amino acid residues from positions 347-357 of wild type HPV66 L1 protein with the amino acid residues from positions 347-357 of wild type HPV56 L1 protein, and the substitution of the amino acid residues from positions 259-283 of wild type HPV66 L1 protein with the amino acid residues from positions 258-282 of wild type HPV53 L1 protein.

The mutated protein H66N5-56T5-53S2-53S3 differs from HPV66N5 by: the substitution of the amino acid residues from positions 347-357 of wild type HPV66 L1 protein with the amino acid residues from positions 347-357 of wild type HPV56 L1 protein, and the substitution of the amino acid residues from positions 114-150 of wild type HPV66 L1 protein with the amino acid residues from positions 113-149 of wild type HPV53 L1 protein, and the substitution of the amino acid residues from positions 172-181 of wild type HPV66 L1 protein with the amino acid residues from positions 171-180 of wild type HPV53 L1 protein.

TABLE 2

| | | PCR templates and primers for constructing expression vectors | | |
|---|---|---|---|---|
| Template | Upstream primer | Downstream primer | Product | Temperature/ Time of annealing |
| 66L1N5 | H66N5-56T1-F | H66N5-56T1-R | H66N5-56T1 | 56° C./50 s |
| 66L1N5 | G-V- H66N5-56T2-F | G-V- H66N5-56T2-R | H66N5-56T 2 long fragment | 56° C./50 s |
| 66L1N5 | H66N5-56T3-F | H66N5-56T3-R | H66N5-56T3 | 56° C./50 s |
| 66L1N5 | G-V-H66N5-56T4-F | G-V-H66N5-56T4-R | H66N5-56T4 long fragment | 56° C./50 s |
| 66L1N5 | G-V-H66N5-56T5-F | G-V-H66N5-56T5-R | H66N5-56T5 long fragment | 56° C./50 s |
| 56L1N0 | G-H66N5-56T2-F | G-H66N5-56T2-R | H66N5-56T2 short fragment | 56° C./30 s |
| 56L1N0 | G-H66N5-56T4-F | G-H66N5-56T4-R | H66N5-56T4 short fragment | 56° C./30 s |
| 56L1N0 | G-H66N5-56T5-F | G-H66N5-56T5-R | H66N5-56T5 short fragment | 56° C./30 s |
| H66N5-56T5 | G-V-H66N5-56T5-53S1-F | G-V-H66N5-56T5-53S1-R | H66N5-56T5-53S1 long fragment | 56° C./50 s |
| H66N5-56T5 | G-V-H66N5-56T5-53S2-F | G-V-H66N5-56T5-53S2-R | H66N5-56T5-53S2 long fragment | 56° C./50 s |
| H66N5-56T5 | G-V-H66N5-56T5-53S4-F | G-V-H66N5-56T5-53S4-R | H66N5-56T5-53S4 long fragment | 56° C./50 s |
| 53L1N5 | G-H66N5-56T5-53S1-F | G-H66N5-56T5-53S1-R | H66N5-56T5-53S1 short fragment | 56° C./30 s |
| 53L1N5 | G-H66N5-56T5-53S2-F | G-H66N5-56T5-53S2-R | H66N5-56T5-53S2 short fragment | 56° C./30 s |
| 53L1N5 | G-H66N5-56T5-53S4-F | G-H66N5-56T5-53S4-R | H66N5-56T5-53S4 short fragment | 56° C./30 s |

TABLE 3

Sequences of the primers used (SEQ ID NOs: 35-62)

| SEQ ID NO: | Primer name | Primer sequence (5'-3') |
|---|---|---|
| 35 | H66N5-56T1-F | AGCGTGACCAAGGACAACACCAAGACCAACATCCCCAAGGTG |
| 36 | H66N5-56T1-R | CTTGGTGTTGTCCTTGGTCACGCTGTAGTAGGGGTGGCCCAC |
| 37 | G-V-H66N5-56T2-F | CACCTCCAGGCCCACGCAGGC |
| 38 | G-V-H66N5-56T2-R | AAGCAGACCCAGCTGTGCATC |
| 39 | H66N5-56T3-F | AGCACCCAGGTCACCACCGGCGACTGCCCCCCTCTGGCCCTG |
| 40 | H66N5-56T3-R | GCCGGTGGTGACCTGGGTGCTCTTGCACACGGCGCCCTTGGT |
| 41 | G-V-H66N5-56T4-F | GTGCCTGGCGAACAGCTGCTC |
| 42 | G-V-H66N5-56T4-R | GCCACCCCAGCGGCAGCATG |
| 43 | G-V-H66N5-56T5-F | GGCGGCGTTGATGGTCATGTT |
| 44 | G-V-H66N5-56T5-R | ATCAACCAGTACCTGAGGCAC |
| 45 | G-H66N5-56T2-F | GCCTGCGTGGGCCTGGAGGTGGGCAGAGGCCAGCCTCTGGGA |
| 46 | G-H66N5-56T2-R | GATGCACAGCTGGGTCTGCTTGCCGTCCACGCTGATGTTGTC |
| 47 | G-H66N5-56T4-F | GAGCAGCTGTTCGCCAGGCACTACTTCAACAGAGCCGGCAAA |
| 48 | G-H66N5-56T4-R | CATGCTGCCGCTGGGGGTGGCCACGTACACGCTGCTGGGAGG |
| 49 | G-H66N5-56T5-F | AACATGACCATCAACGCCGCCACCGAGCAGCTGTCCAAGTAC |
| 50 | G-H66N5-56T5-R | GTGCCTCAGGTACTGGTTGATCTTCCGGGCGTCGTACTTGGA |
| 51 | G-V-H66N5-56T5-53S1-F | GTAGGGGTGGCCCACGGCCAG |
| 52 | G-V-H66N5-56T5-53S1-R | GCCTACCAGTACAGGGTGTTC |
| 53 | G-V-H66N5-56T5-53S2-F | CACCTCCAGGCCCACGCAGGC |
| 54 | G-V-H66N5-56T5-53S2-R | AAGCAGACCCAGCTGTGCATC |
| 55 | G-V-H66N5-56T5-53S4-F | GTGCCTGGCGAACAGCTGCTC |
| 56 | G-V-H66N5-56T5-53S4-R | GCCACCCCAGCGGCAGCATG |
| 57 | G-H66N5-56T5-53S1-F | CTGGCCGTGGGCCACCCCTACTACCCCATCAGCAAGAGCGGC |
| 58 | G-H66N5-56T5-53S1-R | GAACACCCTGTACTGGTAGGCGCTCACCTTGGGGATGTCGGC |
| 59 | G-H66N5-56T5-53S2-F | GCCTGCGTGGGCCTGGAGGTGGGCAGGGGCCAGCCCCTGGGC |
| 60 | G-H66N5-56T5-53S2-R | GATGCACAGCTGGGTCTGCTTGGGGTCCACGCTCACGTTGTC |
| 61 | G-H66N5-56T5-53S4-F | GAGCAGCTGTTCGCCAGGCACTTCTTCAACAGGGCCGGCGTG |
| 62 | G-H66N5-56T5-53S4-R | CATGCTGCCGCTGGGGGTGGCCACGTACACGCTGCTGGGGGG |

Expression of the Mutated Proteins on a Large Scale

The E. coli solutions comprising the recombinant plasmid pTO-T7-H66N5-56T1, pTO-T7-H66N5-56T2, pTO-T7-H66N5-56T3, pTO-T7-H66N5-56T4, pTO-T7-H66N5-56T5, pTO-T7-H66N5-56T5-53S1, pTO-T7-H66N5-56T5-53S2, pTO-T7-H66N5-56T5-53S4 and pTO-T7-H66N5-56T5-53S2-53S3, respectively, were taken from −70° C. refrigerator, were inoculated in 100 mL LB liquid medium containing kanamycin, and incubated at 200 rpm and 37° C. for about 8 h. Then, the culture was transferred to 500 mL LB medium containing kanamycin (1 ml bacterial solution was transferred), and was further incubated. When the bacterial concentration reached an $OD_{600}$ of about 0.6, the culturing temperature was lowered to 25° C. and 500 μL IPTG was added to each culture bottle. The incubation was further performed for 8 h. After the incubation was finished, the bacteria were collected by centrifugation. The bacteria expressing H66N5-56T1, H66N5-56T2, H66N5-56T3, H66N5-56T4, H66N5-56T5, H66N5-56T5-53S1, H66N5-56T5-53S2, H66N5-56T5-53S4 and H66N5-56T5-53S2-53S3 protein were obtained, respectively.

Disruption of Bacteria Expressing the Mutated Proteins

The bacteria obtained were re-suspended at a ratio of 1 g bacteria to 10 mL lysis buffer (20 mM Tris buffer, pH7.2, 300 mM NaCl). The bacteria were disrupted by using an ultrasonic apparatus for 30 min. The lysis solution containing the disrupted bacteria were centrifuged at 13500 rpm (30000 g) for 15 min, and the supernatant (i.e. the supernatant of disrupted bacteria) was obtained.

Chromatographic Purification of the Mutated Protein

Equipment: AKTA Explorer 100 preparative liquid chromatography system produced by GE Healthcare (i.e. the original Amershan Pharmacia Co.)

Chromatographic media: SP Sepharose 4 Fast Flow (GE Healthcare Co.), CHT-II (purchased from Bio-RAD) and Butyl Sepharose 4 Fast Flow (GE Healthcare Co.)

Buffer: Buffer A (20 mM phosphate buffer, pH8.0, 20 mM DTT); and Buffer B (20 mM phosphate buffer, pH8.0, 20 mM DTT, 2M NaCl). The buffers containing different concentrations of NaCl used in the following elution protocol were prepared by mixing Buffer A and Buffer B at a certain ratio.

Sample: the supernatants of disrupted bacteria containing H66N5-56T1, H66N5-56T2, H66N5-56T3, H66N5-56T4, H66N5-56T5, H66N5-56T5-53S1, H66N5-56T5-53S2, H66N5- 56T5-53S4 and H66N5-56T5-53S2-53S3, respectively, as obtained above.

Elution Protocol:

(1) Cation exchange purification of the supernatant of disrupted bacteria by SP Sepharose 4 Fast Flow: the sample was loaded on the column, undesired proteins were then eluted with a buffer containing 400 mM NaCl (80% Buffer A+20% Buffer B), followed by the elution of the protein of interest with a buffer containing 800 mM NaCl (60% Buffer A+40% Buffer B), and the fraction eluted with the buffer containing 800 mM NaCl was collected;

(2) Chromatographic purification of the elution fraction obtained in the step (1) by CHTII (hydroxyapatite chromatography): the elution fraction obtained in the step (1) was diluted so that the NaCl concentration was decreased to 0.5 M; the sample was loaded on the column, undesired proteins were then eluted with a buffer containing 500 mM NaCl (75% Buffer A+25% Buffer B), followed by the elution of the protein of interest with a buffer containing 1000 mM NaCl (50% Buffer A+50% Buffer B), and the fraction eluted with the buffer containing 1000 mM NaCl was collected;

(3) Chromatographic purification of the elution fraction obtained in the step (2) by HIC (hydrophobic interaction chromatography): the sample was loaded on the column, undesired proteins were then eluted with a buffer containing 1000 mM NaCl, followed by the elution of the protein of interest with a buffer containing 200 mM NaCl (90% Buffer A+10% Buffer B), and the fraction eluted with the buffer containing 200 mM NaCl was collected.

150 μL of elution fraction obtained in the step (3) was added to 30 μL of 6× Loading Buffer (1 L of which contained 300 ml of 1M TB 6.8, 600 ml of 100% glycerol, 120 g of SDS, 6 g of bromophenol blue, and 50 ml of β-mercaptoethanol). The resultant solution was mixed well and incubated in 80° C. water bath for 10 min. 10 μl of the resultant sample was then subjected to 10% SDS-PAGE at 120V for 120 min; and the electrophoretic bands were stained by Coomassie brilliant blue. The electrophoretic result was shown in FIG. 1. The result showed that after said purification steps, H66N5-56T1, H66N5-56T2, H66N5-56T3, H66N5-56T4, H66N5-56T5, H66N5-56T5-53S1, H66N5-56T5- 53S2 and H66N5-56T5-53S4 protein had a purity of about 90%, and H66N5-56T5-53S2-53S3 had a purity of about 75%.

By similar methods, HPV66N5 protein was prepared and purified by using E. coli and the plasmid pTO-T7-HPV66N5; HPV56N0 protein was prepared and purified by using E. coli and the plasmid pTO-T7-HPV56L1N0; and HPV53N5 protein was prepared and purified by using E. coli and the plasmid pTO-T7-HPV53N5.

Western Blot Assay of the Mutated Proteins

Figure 2:
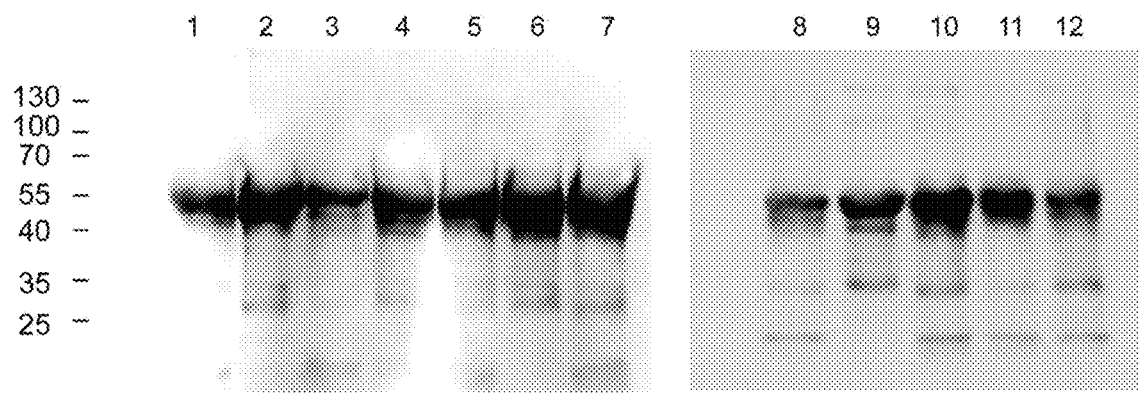
FIG. 2 shows the Western Blot result of the mutated proteins H66N5-56T1, H66N5-56T2, H66N5-56T3, H66N5-56T4, H66N5-56T5, H66N5-56T5-53S1, H66N5-56T5-53S2 and H66N5-56T5-53S4 prepared in Example 1, as determined by using a HPV L1 broad-spectrum antibody 4B3. Lane 1: HPV66N5 (HPV66 L1 protein having 5 amino acids truncated at N-terminal); Lane 2: HPV56N0 (full-length HPV56 L1 protein); Lane 3: H66N5-56T1; Lane 4: H66N5-56T2; Lane 5: H66N5-56T3; Lane 6: H66N5-56T4; Lane 7: H66N5-56T5; Lane 8: H66N5-56T5; Lane 9: HPV53N5 (HPV53 L1 protein having 5 amino acids truncated at N-terminal); Lane 10: H66N5-56T5-53S1; Lane 11: H66N5-56T5-53S2; Lane 12: H66N5-56T5-53S4. The result showed that the mutated proteins H66N5-56T1, H66N5-56T2, H66N5-56T3, H66N5-56T4, H66N5-56T5, H66N5-56T5-53S1, H66N5-56T5-53S2 and H66N5-56T5-53S4 could be specifically recognized by the broad-spectrum antibody 4B3.

The H66N5-56T1, H66N5-56T2, H66N5-56T3, H66N5-56T4, H66N5-56T5, H66N5-56T5-53S1, H66N5-56T5-53S2 and H66N5-56T5-53S4 protein purified by the method above were subjected to electrophoresis. After electrophoresis, Western Blot assay was carried out by using a broad-spectrum antibody 4B3 against HPV L1 protein, and the result was shown in FIG. 2. The result showed that H66N5-56T1, H66N5-56T2, H66N5-56T3, H66N5-56T4, H66N5-56T5, H66N5-56T5-53S1, H66N5-56T5-53S2 and H66N5-56T5-53S4 could be specifically recognized by the broad-spectrum antibody 4B3.

Example 2: Assembly of HPV Virus-Like Particles and Morphological Detection of Particles Assembly of HPV Virus-Like Particles A given volume (about 2 ml) of the protein H66N5-56T1, H66N5-56T2, H66N5-56T3, H66N5-56T4, H66N5-56T5, H66N5-56T5-53S1, H66N5-56T5-53S2, H66N5-56T5-53S4 or H66N5-56T5-53S2-53S3, was dialyzed to (1) 2 L storage buffer (20 mM sodium phosphate buffer pH 6.5, 0.5 M NaCl); (2) 2 L renaturation buffer (50 mM sodium phosphate buffer pH 6.0, 2 mM $CaCl_2$, 2 mM $MgCl_2$, 0.5 M NaCl); and (3) 20 mM sodium phosphate buffer pH 7.0, 0.5 M NaCl, successively. The dialysis was performed in each of the three buffers for 12 h.

By similar methods, the HPV66N5, HPV56N0 and HPV53N5 protein were assembled into HPV66N5 VLP, HPV56N0 VLP and HPV53N5 VLP, respectively.

Molecular Sieve Chromatographic Analysis

Figure 3:
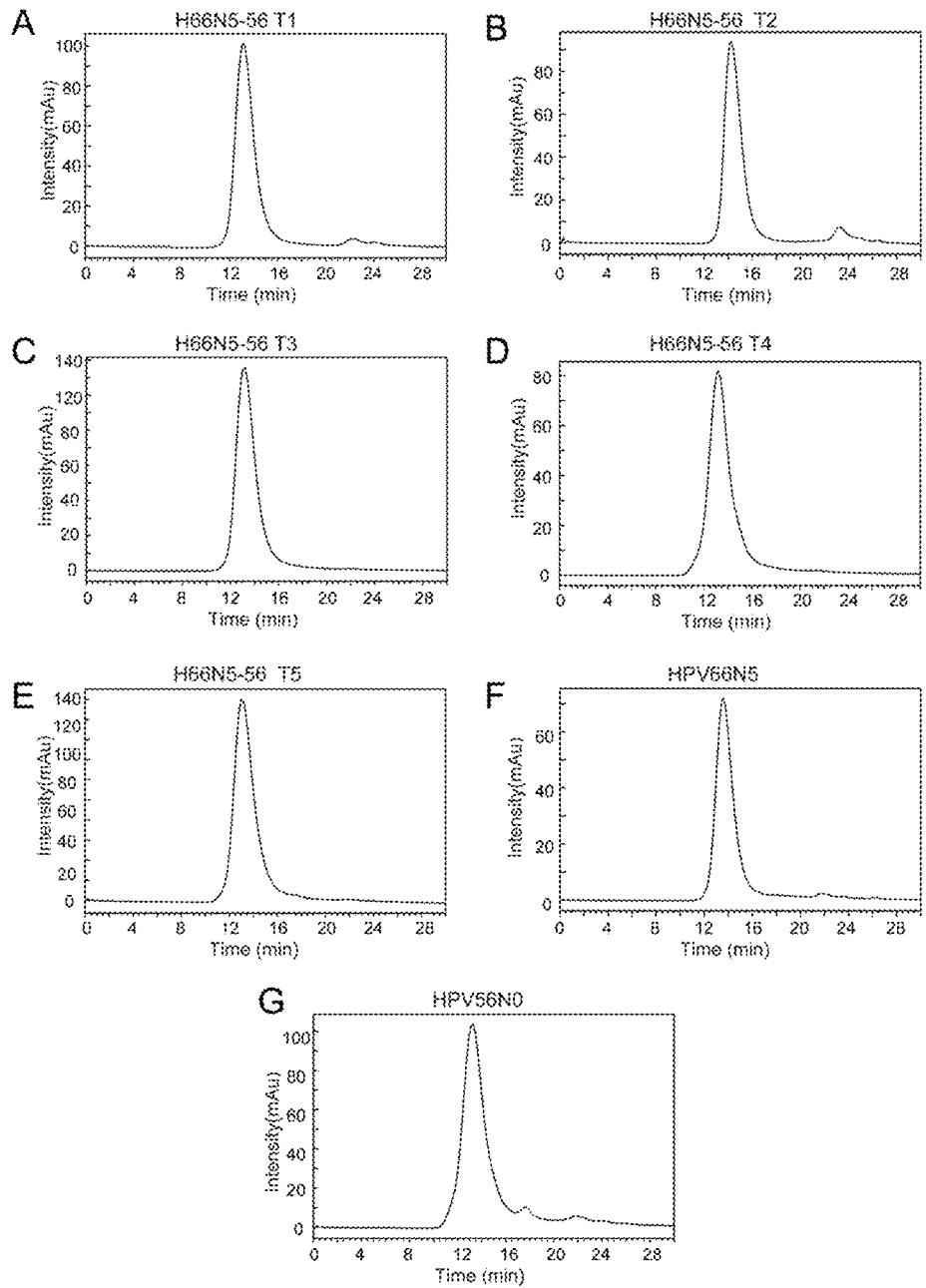
FIG. 3 shows the results of the samples comprising the protein H66N5-56T1, H66N5-56T2, H66N5-56T3, H66N5-56T4, H66N5-56T5, HPV56N0 and HPV66N5 (HPV66 L1 protein having 5 amino acids truncated at N-terminal), as analyzed by molecular sieve chromatography. The results showed that the first protein peak of the samples comprising the protein H66N5-56T1, H66N5-56T2, H66N5-56T3, H66N5-56T4 and H66N5-56T5 appeared at about 13-14 min, which was comparable to that of HPV56N0 VLP and that of HPV66N5 VLP. This showed that all these proteins were able to assemble into VLPs.
Figure 4:
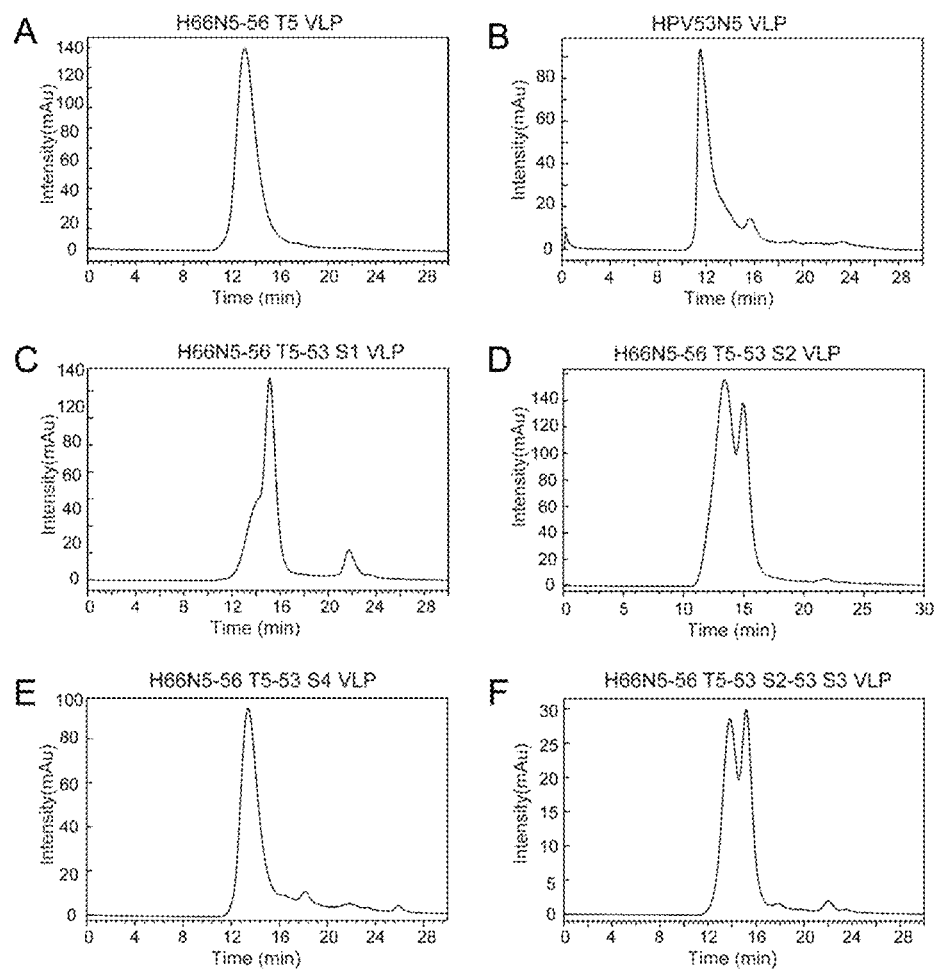
FIG. 4 shows the results of the samples comprising the protein H66N5-56T5, HPV53N5, H66N5-56T5-53S1, H66N5-56T5-53S2, H66N5-56T5-53S4 and H66N5-56T5-53S2-53S3, as analyzed by molecular sieve chromatography. The results showed that the first protein peak of the samples comprising the protein H66N5-56T5 and H66N5-56T5-53S4 appeared at about 13-14 min, which was comparable to that of HPV53N5. The protein peak of the samples comprising H66N5-56T5-53S1 and H66N5-56T5-53S2 was asymmetric, and the first protein peak of the samples comprising H66N5-56T5-53S1 appeared at about 15 min, this showed that VLP formed by H66N5-56T5-53S1 had a smaller diameter, and VLPs formed by H66N5-56T5-53S2 and H66N5-56T5-53S2-53S3 had a non-uniform size.

The dialyzed sample was subjected to molecular sieve chromatographic analysis by 1120 Compact LC High Performance Liquid Chromatographic System (Agilent Technologies), wherein the analytical column used was TSK Gel PW5000×1 7.8×300 mm. The analysis results were shown in FIGS. 3 and 4. The results showed that the first protein peak of the samples comprising the protein H66N5-56T1, H66N5-56T2, H66N5-56T3, H66N5-56T4, H66N5-56T5 or H66N5-56T5-53S4 appeared at about 13-14 min, which was comparable to that of HPV66N5 VLP, HPV56N0 VLP and HPV53N5 VLP, this showed that all these protein were able to assemble into VLPs. The protein peak of the samples comprising H66N5-56T5-53S2-53S3, H66N5-56T5-53S1 or H66N5-56T5-53S2 was asymmetric, and the first protein peak of the samples comprising H66N5-56T5-53S1 appeared at about 15 min, this showed that VLP formed by H66N5-56T5-53S1 had a smaller diameter, and VLPs formed by H66N5-56T5-53S2 or H66N5-56T5-53S2-53S3 had a non-uniform size.

Sedimentation Velocity Analysis

Figure 5:
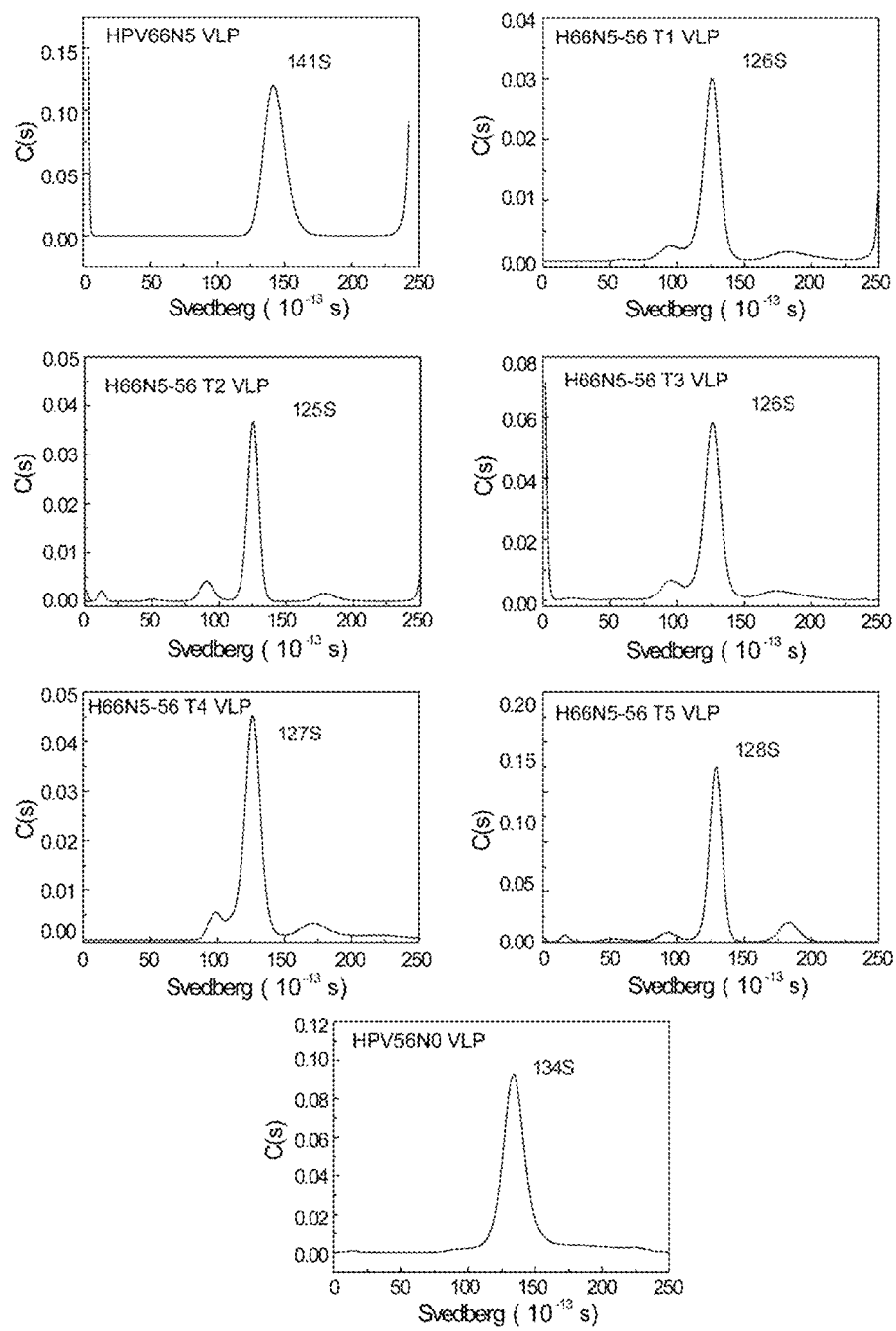
FIG. 5 shows the results of sedimentation velocity analysis of H66N5-56T1 VLP, H66N5-56T2 VLP, H66N5-56T3 VLP, H66N5-56T4 VLP, H66N5-56T5 VLP, HPV56N0 VLP and HPV66N5 VLP. The results showed that the sedimentation coefficients of H66N5-56T1 VLP, H66N5-56T2 VLP, H66N5-56T3 VLP, H66N5-56T4 VLP and H66N5-56T5 VLP were 126S, 125S, 126S, 127S and 128S, respectively, while the sedimentation coefficients of HPV56N0 VLP and HPV66N5 VLP were 134S and 141S, respectively. This showed that H66N5-56T1, H66N5-56T2, H66N5-56T3, H66N5-56T4 and H66N5-56T5 were able to assemble into virus-like particles that were similar to wild type VLP in terms of size and morphology.
Figure 6:
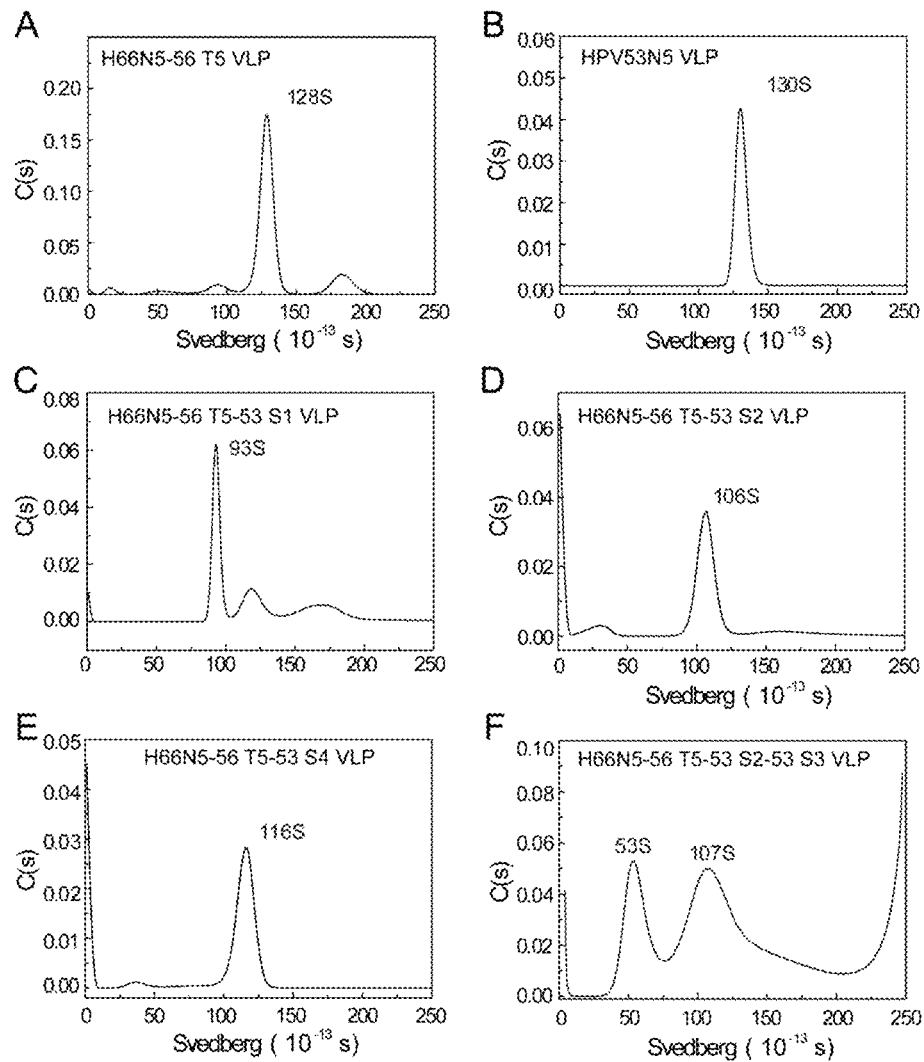
FIG. 6 shows the results of sedimentation velocity analysis of H66N5-56T5 VLP, HPV53N5 VLP, H66N5-56T5-53S1 VLP, H66N5-56T5-53S2 VLP, H66N5-56T5-53S4 VLP and H66N5-56T5-53S2-53S3. The results showed that the sedimentation coefficients of H66N5-56T5 VLP, HPV53N5 VLP, H66N5-56T5-53S1 VLP, H66N5-56T5-53S2 VLP and H66N5-56T5-53S4 VLP were 128S, 130S, 93S, 106S and 116S, respectively, the sedimentation coefficients of H66N5-56T5-53S2-53S3VLP were 53S and 107S. This showed that H66N5-56T5-53S4 was able to assemble into virus-like particles that were similar to wild type VLP in terms of size and morphology, while VLPs formed by H66N5-56T5-53S1, H66N5-56T5-53S2 and H66N5-56T5-53S2-53S3 had a smaller diameter, and VLPs formed by H66N5-56T5-53S2 and H66N5-56T5-53S2-53S3 had a non-uniform size.
Figure 7A:
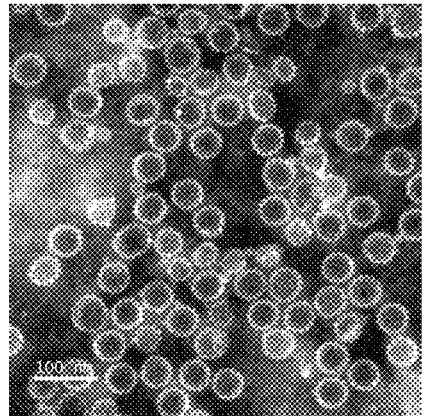
Figure 7B:
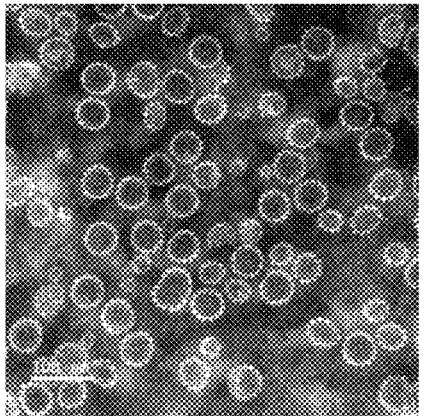
Figure 7C:
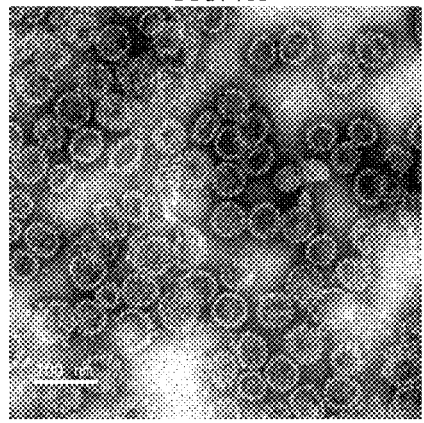
Figure 7D:
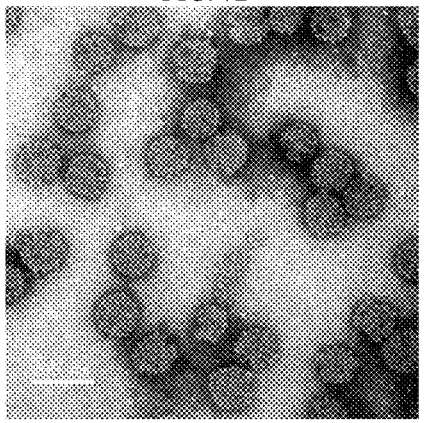
Figure 7E:
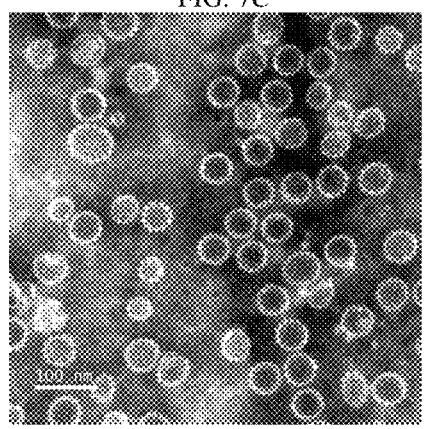
Figure 7F:
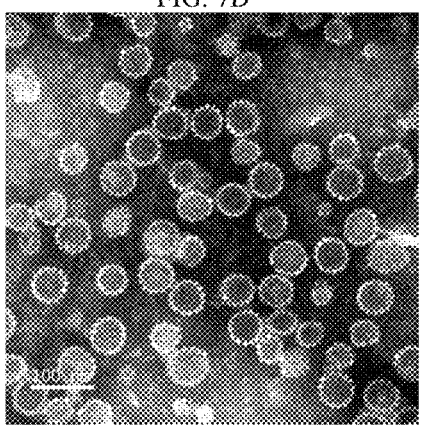
Figure 7G:
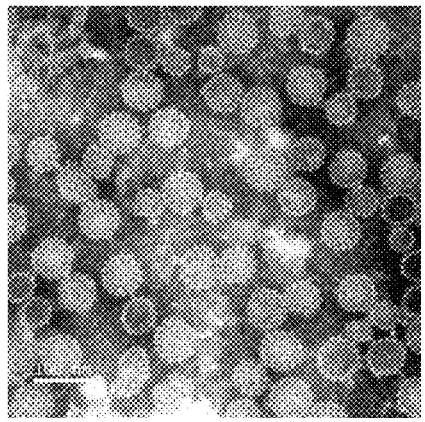
Figure 7H:
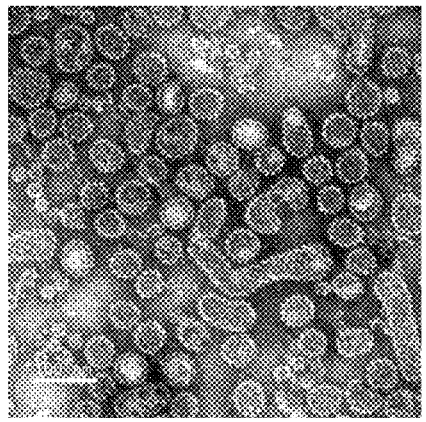
Figure 7I:
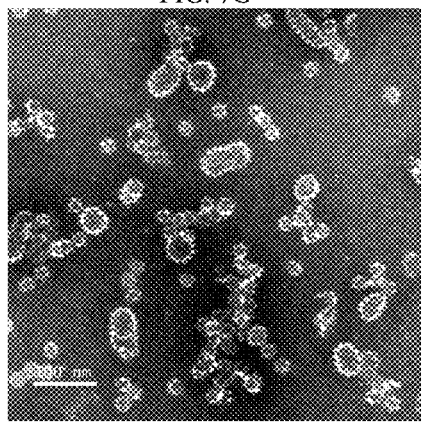
Figure 7J:
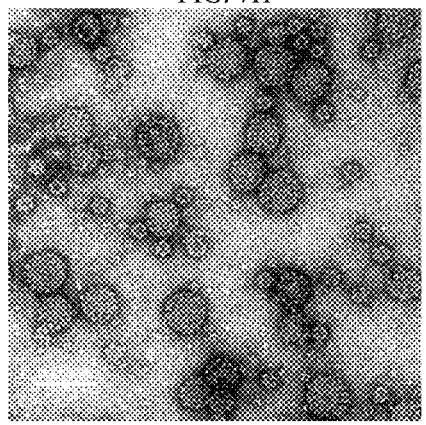
Figure 7K:
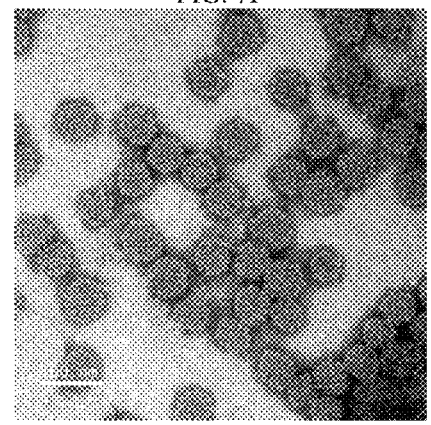
Figure 7L:
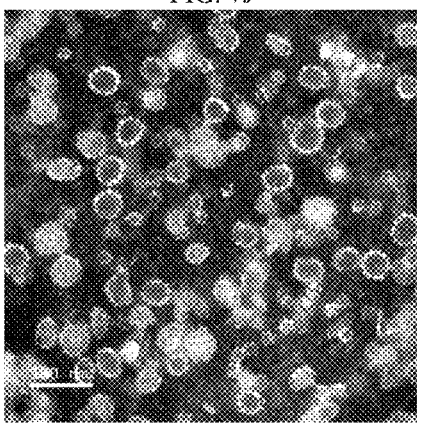

The apparatus for sedimentation velocity analysis was Beckman XL-A Analytical Ultracentrifuge, equipped with optical inspection system and An-50Ti and An-60Ti rotor. The sedimentation coefficients of H66N5-56T1 VLP, H66N5-56T2 VLP, H66N5-56T3 VLP, H66N5-56T4 VLP, H66N5-56T5 VLP, H66N5-56T5-53S1 VLP, H66N5-56T5-53S2 VLP, H66N5-56T5-53S4 VLP, H66N5-56T5-53S2-53S3 VLPHPV56N0 VLP, HPV66N5 VLP and HPV53N5 VLP were analyzed by sedimentation velocity method. The results were shown in FIGS. 5 and 6. The results showed that the sedimentation coefficients of H66N5-56T1 VLP, H66N5-56T2 VLP, H66N5-56T3 VLP, H66N5-56T4 VLP, H66N5-56T5 VLP, H66N5-56T5-53S1 VLP, H66N5-56T5-53S2 VLP and H66N5-56T5-53S4 VLP were 126S, 125S, 126S, 127S, 128S, 93S, 106S and 116S, respectively, the sedimentation coefficients of H66N5-56T5-53S2-53S3 VLP were 53S and 107S, the sedimentation coefficients of HPV56N0 VLP, HPV66N5 VLP and HPV53N5 VLP were 134S, 141S and 130S, respectively. This showed that H66N5-56T1, H66N5-56T2, H66N5-56T3, H66N5-56T4, H66N5-56T5 and H66N5-56T5-53S4 were able to assemble into virus-like particles that were similar to wild type VLP (HPV56N0 VLP, HPV66N5 VLP and HPV53N5 VLP) in terms of size and morphology, while H66N5-56T5-53S1 VLP, H66N5-56T5-53S2 VLP and H66N5-56T5-53S2-53S3 VLP had a smaller diameter, and H66N5-56T5-53S2 VLP and H66N5-56T5-53S2-53S3 VLP had a non-uniform size.

Morphological Test of Virus-Like Particles

A 100 μL sample comprising VLP was observed by transmission electron microscope (TEM). The apparatus used was a 100 kV Transmission Electron Microscope supplied by JEOL Ltd. (100,000× magnification). In brief, a 13.5 μL sample was negatively stained with 2% phosphotungstic acid (pH 7.0), fixed on a carbon-coated copper grid, and then observed by TEM. The results were shown in FIGS. 7A-7L. The results showed that H66N5-56T1, H66N5-56T2, H66N5-56T3, H66N5-56T4, H66N5-56T5, H66N5-56T5-53S2, H66N5-56T5-53S4 and H66N5-56T5-53S2-53S3 were able to assemble into virus-like particles. In addition, the results also showed that the particles assembled by H66N5-56T1, H66N5-56T2, H66N5-56T3, H66N5-56T4, H66N5-56T5 and H66N5-56T5-53S4 had a radius of about 25 nm, and were uniform in size, this indicated that these mutated proteins were similar to the L1 protein of HPV66, HPV56 and HPV53, and were able to assemble into VLPs with a uniform size. H66N5-56T5-53S2 and H66N5-56T5-53S2-53S3 were also able to assemble into VLPs with a radius of about 25 nm, but in which small particles with a diameter of about 20 nm were involved; while H66N5-56T5-53S1 was able to assemble into irregular VLP with a radius of about 10-20 nm.

Example 3: Evaluation 1 of Neutralizing Antibody Titer in Serum of Mice Vaccinated with Virus-Like Particles In this experiment, virus-like particles used were H66N5-56T1 VLP, H66N5-56T2 VLP, H66N5-56T3 VLP, H66N5-56T4 VLP and H66N5-56T5 VLP.

In this experiment, vaccination schedule was shown in Table 4. All the mice (6-week old BalB/c female mice) were divided into 3 groups: Aluminum adjuvant group 1 (at an immunizing dose of 5 μg, using aluminum adjuvant), Aluminum adjuvant group 2 (at an immunizing dose of 1 μg, using aluminum adjuvant), and Aluminum adjuvant group 3 (at an immunizing dose of 0.2 μg, using aluminum adjuvant). Each group was further divided into 8 subgroups. The Control subgroups 1 and 2 were vaccinated with HPV66N5 VLP alone and HPV56N0 VLP alone, respectively, the Control subgroup 3 was vaccinated with the mixed HPV66/HPV56 VLP (i.e. a mixture of HPV66N5 VLP and HPV56N0 VLP, at a given immunizing dose for each VLP). The Experimental subgroups 1, 2, 3, 4 and 5 were vaccinated with H66N5-56T1VLP, H66N5-56T2VLP, H66N5-56T3VLP, H66N5-56T4VLP and H66N5-56T5 VLP, respectively.

Figure 8A:
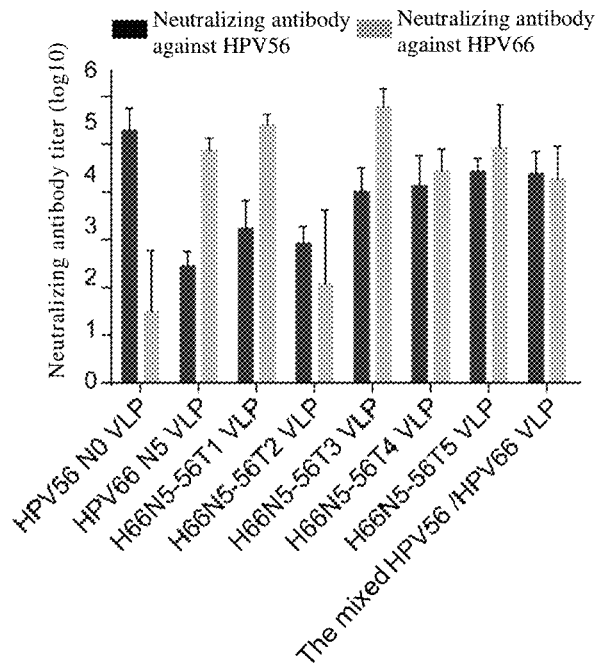
Figure 8B:
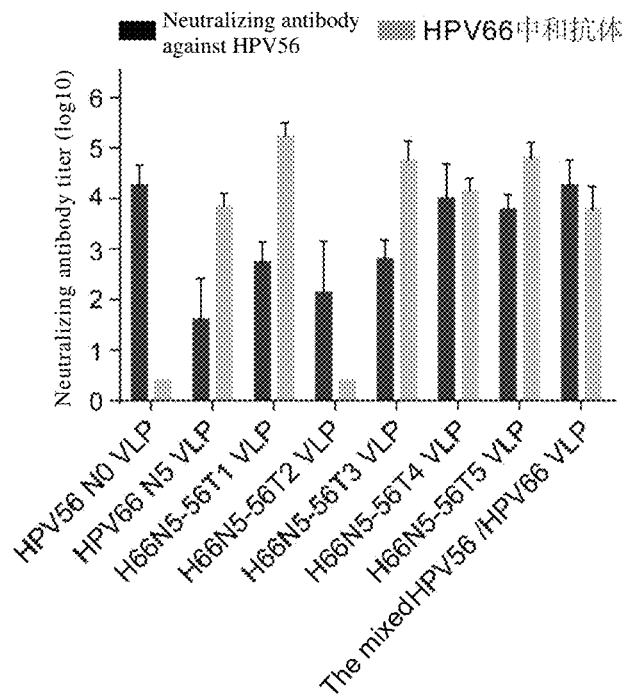
Figure 8C:
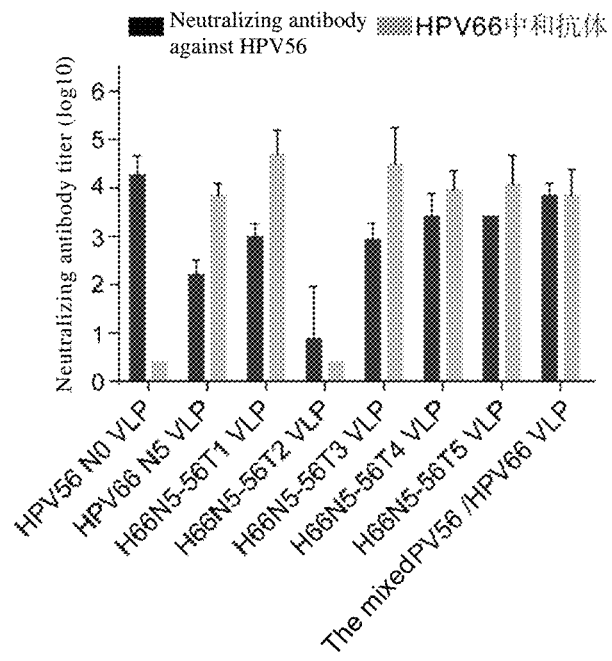

In Aluminum adjuvant groups 1-3, 5 mice/subgroup were vaccinated by intraperitoneal injection, at an immunizing dose of 5 μg, 1 μg, and 0.2 μg, respectively, and an injection volume of 1 mL. All the mice were subjected to the first vaccination at Week 0, and then subjected to the booster vaccination at Weeks 2 and 4, respectively. At Week 6, blood sample was collected via orbital bleeding, and the titers of antibodies against HPV66 and HPV56 in serum were analyzed. The analysis results were shown in FIGS. 8A-8C. The results showed that H66N5-56T4 VLP and H66N5-56T5 VLP could induce the generation of high-titer neutralizing antibodies against HPV66 in mice, and their protective effects were comparable to that of HPV66N5 VLP alone at the same dose, and was significantly superior to that of HPV56N0 VLP alone at the same dose; and they could induce the generation of high-titer neutralizing antibodies against HPV56 in mice, and their protective effects were comparable to that of HPV56N0 VLP alone at the same dose, and was significantly superior to that of HPV66N5 VLP alone at the same dose. This showed that H66N5-56T4 VLP and H66N5-56T5 VLP had good cross-immunogenicity and cross-protection against HPV66 and HPV56.

TABLE 4

Vaccination schedule

| Group | Antigen for vaccination | Adjuvant | Immunizing dose | Number | Vaccination procedure (week) |
|---|---|---|---|---|---|
| Aluminum adjuvant group 1 | HPV66N5 VLP | aluminum adjuvant | 5 μg | 5 | 0, 2, 4 |
| | HPV56N0 VLP | aluminum adjuvant | 5 μg | 5 | 0, 2, 4 |

TABLE 4-continued

Vaccination schedule

| Group | Antigen for vaccination | Adjuvant | Immunizing dose | Number | Vaccination procedure (week) |
|---|---|---|---|---|---|
| | The mixed HPV66/HPV56 VLP | aluminum adjuvant | 5 μg for each VLP | 5 | 0, 2, 4 |
| | H66N5-56T1VLP | aluminum adjuvant | 5 μg | 5 | 0, 2, 4 |
| | H66N5-56T2VLP | aluminum adjuvant | 5 μg | 5 | 0, 2, 4 |
| | H66N5-56T3VLP | aluminum adjuvant | 5 μg | 5 | 0, 2, 4 |
| | H366N5-56T4VLP | aluminum adjuvant | 5 μg | 5 | 0, 2, 4 |
| | H66N5-56T5VLP | aluminum adjuvant | 5 μg | 5 | 0, 2, 4 |
| Aluminum adjuvant group 2 | HPV66N5 VLP | aluminum adjuvant | 1 μg | 5 | 0, 2, 4 |
| | HPV56N0 VLP | aluminum adjuvant | 1 μg | 5 | 0, 2, 4 |
| | The mixed HPV66/HPV56 VLP | aluminum adjuvant | 1 μg for each VLP | 5 | 0, 2, 4 |
| | H66N5-56T1VLP | aluminum adjuvant | 1 μg | 5 | 0, 2, 4 |
| | H66N5-56T2VLP | aluminum adjuvant | 1 μg | 5 | 0, 2, 4 |
| | H66N5-56T3VLP | aluminum adjuvant | 1 μg | 5 | 0, 2, 4 |
| | H366N5-56T4VLP | aluminum adjuvant | 1 μg | 5 | 0, 2, 4 |
| | H66N5-56T5VLP | aluminum adjuvant | 1 μg | 5 | 0, 2, 4 |
| Aluminum adjuvant group 3 | HPV66N5 VLP | aluminum adjuvant | 0.2 μg | 5 | 0, 2, 4 |
| | HPV56N0 VLP | aluminum adjuvant | 0.2 μg | 5 | 0, 2, 4 |
| | The mixed HPV66/HPV56 VLP | aluminum adjuvant | 0.2 μg for each VLP | 5 | 0, 2, 4 |
| | H66N5-56T1VLP | aluminum adjuvant | 0.2 μg | 5 | 0, 2, 4 |
| | H66N5-56T2VLP | aluminum adjuvant | 0.2 μg | 5 | 0, 2, 4 |
| | H66N5-56T3VLP | aluminum adjuvant | 0.2 μg | 5 | 0, 2, 4 |
| | H366N5-56T4VLP | aluminum adjuvant | 0.2 μg | 5 | 0, 2, 4 |
| | H66N5-56T5VLP | aluminum adjuvant | 0.2 μg | 5 | 0, 2, 4 |

Example 4: Evaluation of $ED_{50}$ of Virus-Like Particles for Inducing Seroconversion In this experiment, virus-like particles used were H66N5-56T4 VLP and H66N5-56T5 VLP. 6-Week old BalB/c female mice (8 mice) were vaccinated with aluminum adjuvant by single intraperitoneal injection, wherein H66N5-56T4 VLP or H66N5-56T5 VLP was used in the Experimental groups, and HPV56N0 VLP alone, HPV66N5 VLP alone or the mixed HPV66/HPV56 VLP (i.e. a mixture of HPV66N5 VLP and HPV56N0 VLP) was used in the Control groups; the immunizing dose was 0.900 μg, 0.300 μg, 0.100 μg, 0.033 μg or 0.011 μg; the immunizing volume was 1 mL. In addition, the diluent used to dilute the vaccine was used as a blank control. 8 Mice were vaccinated in each group, and at Week 5 after vaccination, venous blood was collected from eyeball. Antibodies against HPV in the serum were detected, and by Reed-Muench method (Reed L J M H. A simple method of estimating fifty percent endpoints. Am J Hyg. 1938; 27:493-7), $ED_{50}$ for inducing seroconversion (i.e. inducing the generation of antibodies in mice) was calculated for each sample. The results were shown in Tables 5-9.

TABLE 5

$ED_{50}$ of HPV66N5 VLP for inducing the generation of antibodies against HPV66 and HPV56 (seroconversion) in mice

| Type | Dose (μg) | Total number of mice | Number of mice with positive conversion | Positive conversion rate | $ED_{50}$ (μg) |
|---|---|---|---|---|---|
| HPV66 | 0.900 | 8 | 7 | 96% | 0.057 |
| | 0.300 | 8 | 8 | 94.44% | |
| | 0.100 | 8 | 7 | 81.82% | |
| | 0.033 | 8 | 2 | 20.00% | |
| | 0.011 | 8 | 0 | 0.00% | |
| HPV56 | 0.900 | 8 | 2 | 53.85% | 0.747 |
| | 0.300 | 8 | 3 | 31.25% | |
| | 0.100 | 8 | 2 | 10.53% | |
| | 0.033 | 8 | 0 | 0.00% | |
| | 0.011 | 8 | 0 | 0.00% | |

TABLE 6

$ED_{50}$ of HPV56N0 VLP for inducing the generation of antibodies against HPV66 and HPV56 (seroconversion) in mice

| Type | Dose (μg) | Total number of mice | Number of mice with positive conversion | Positive conversion rate | $ED_{50}$ (μg) |
|---|---|---|---|---|---|
| HPV66 | 0.900 | 8 | 0 | 11.11% | >0.9 |
|  | 0.300 | 8 | 1 | 6.25% |  |
|  | 0.100 | 8 | 0 | 0.00% |  |
|  | 0.033 | 8 | 0 | 0.00% |  |
|  | 0.011 | 8 | 0 | 0.00% |  |
| HPV56 | 0.900 | 8 | 7 | 96.88% | 0.021 |
|  | 0.300 | 8 | 8 | 96% |  |
|  | 0.100 | 8 | 8 | 94.12% |  |
|  | 0.033 | 8 | 8 | 88.89% |  |
|  | 0.011 | 8 | 0 | 0.00% |  |

TABLE 7

$ED_{50}$ of H66N5-56T4 VLP for inducing the generation of antibodies against HPV66 and HPV56 (seroconversion) in mice

| Type | Dose (μg) | Total number of mice | Number of mice with positive conversion | Positive conversion rate | $ED_{50}$ (μg) |
|---|---|---|---|---|---|
| HPV66 | 0.900 | 8 | 2 | 53.85% | 0.747 |
|  | 0.300 | 8 | 3 | 31.25% |  |
|  | 0.100 | 8 | 4 | 10.53% |  |
|  | 0.033 | 8 | 0 | 0.00% |  |
|  | 0.011 | 8 | 0 | 0.00% |  |
| HPV56 | 0.900 | 8 | 1 | 50.00% | 0.900 |
|  | 0.300 | 8 | 4 | 35.29% |  |
|  | 0.100 | 8 | 2 | 10.53% |  |
|  | 0.033 | 8 | 0 | 0.00% |  |
|  | 0.011 | 8 | 0 | 0.00% |  |

TABLE 8

$ED_{50}$ of H66N5-56T5 VLP for inducing the generation of antibodies against HPV66 and HPV56 (seroconversion) in mice

| Type | Dose (μg) | Total number of mice | Number of mice with positive conversion | Positive conversion rate | $ED_{50}$ (μg) |
|---|---|---|---|---|---|
| HPV66 | 0.900 | 8 | 7 | 95.24% | 0.100 |
|  | 0.300 | 8 | 8 | 92.86% |  |
|  | 0.100 | 8 | 4 | 50.00% |  |
|  | 0.033 | 8 | 1 | 7.69% |  |
|  | 0.011 | 8 | 0 | 0.00% |  |
| HPV56 | 0.900 | 8 | 5 | 78.57% | 0.300 |
|  | 0.300 | 8 | 5 | 50.00% |  |
|  | 0.100 | 8 | 1 | 7.14% |  |
|  | 0.033 | 8 | 0 | 0.00% |  |
|  | 0.011 | 8 | 0 | 0.00% |  |

TABLE 9

$ED_{50}$ of the mixed HPV66/HPV56 VLP for inducing the generation of antibodies against HPV66 and HPV56 (seroconversion) in mice

| Type | Dose (μg) | Total number of mice | Number of mice with positive conversion | Positive conversion rate | $ED_{50}$ (μg) |
|---|---|---|---|---|---|
| HPV66 | 0.900 | 8 | 7 | 96.88% | 0.021 |
|  | 0.300 | 8 | 8 | 96.00% |  |
|  | 0.100 | 8 | 8 | 94.12% |  |
|  | 0.033 | 8 | 8 | 88.89% |  |
|  | 0.011 | 8 | 0 | 0.00% |  |
| HPV56 | 0.900 | 8 | 8 | 100.00% | 0.018 |
|  | 0.300 | 8 | 8 | 100.00% |  |
|  | 0.100 | 8 | 8 | 100.00% |  |
|  | 0.033 | 8 | 8 | 100.00% |  |
|  | 0.011 | 8 | 1 | 12.50% |  |

The results showed that 5 weeks after vaccination of mice, $ED_{50}$ of H66N5-56T5 VLP for inducing the generation of antibodies against HPV66 in mice was comparable to that of HPV66N5 VLP alone, and was significantly superior to that of HPV56N0 VLP alone; and its $ED_{50}$ of for inducing the generation of antibodies against HPV56 in mice was slightly weaker than that of HPV56N0 VLP alone, but was significantly superior to that of HPV66N5 VLP alone. This showed that H66N5-56T5 VLP had good cross-immunogenicity and cross-protection against HPV66 and HPV56.

Example 5: Evaluation 2 of Neutralizing Antibody Titer in Serum of Mice Vaccinated with Virus-Like Particles In this experiment, virus-like particles used were H66N5-56T5-53S1 VLP, H66N5-56T5-53S2 VLP and H66N5-56T5-53S4 VLP.

In this experiment, vaccination schedule was shown in Table 10. All the mice (6-week old BalB/c female mice) were divided into 2 groups: Aluminum adjuvant group 1 (at an immunizing dose of 5 μg, using aluminum adjuvant), and Aluminum adjuvant group 2 (at an immunizing dose of 1 μg, using aluminum adjuvant). Each group was further divided into 7 subgroups. The Control subgroups 1, 2 and 3 were vaccinated with HPV66N5 VLP alone, HPV56N0 VLP alone and HPV53N5 VLP alone, respectively, the Control subgroup 4 was vaccinated with the mixed HPV66/56/53 VLP (i.e. a mixture of HPV66N5 VLP, HPV56N0 VLP and HPV53N5 VLP, at a given immunizing dose for each VLP). The Experimental subgroups 1, 2 and 3 were vaccinated with H66N5-56T5-53S1 VLP, H66N5-56T5-53S2 VLP and H66N5-56T5-53S4 VLP, respectively.

Figure 9A:
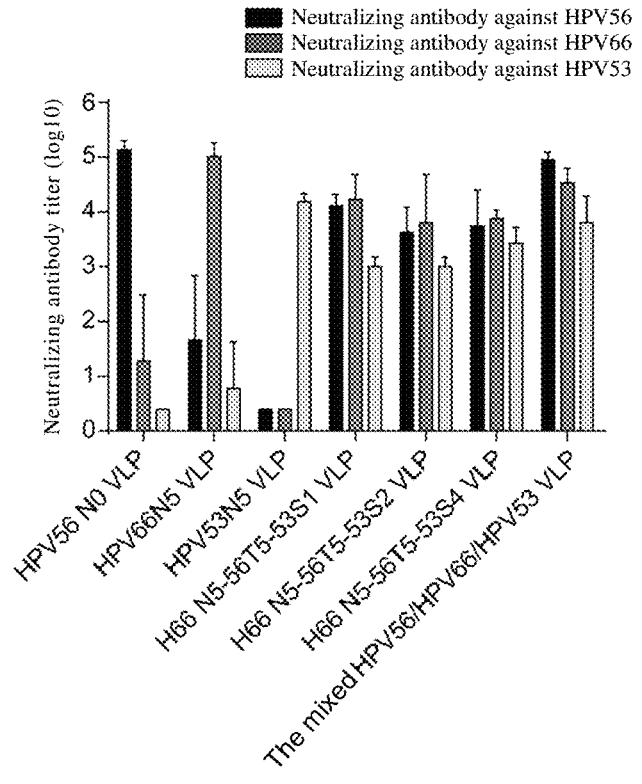
Figure 9B:
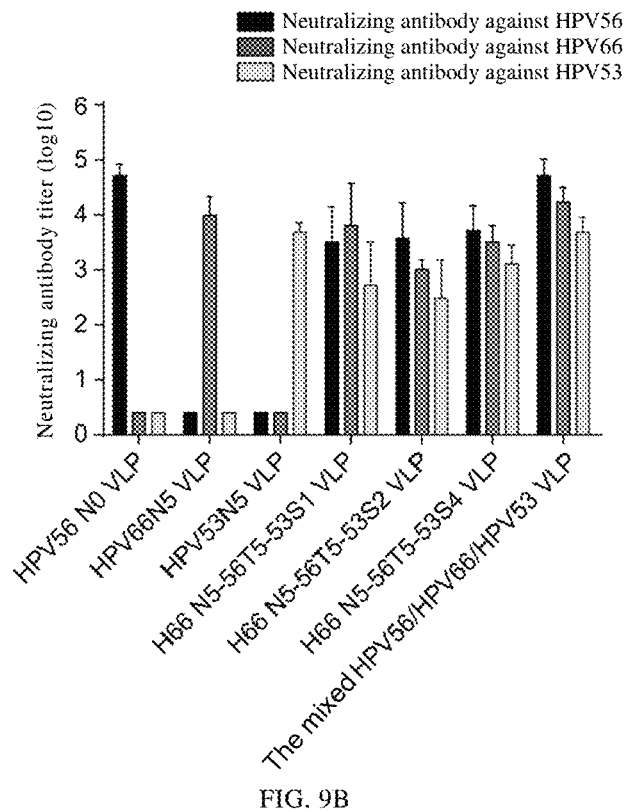

In Aluminum adjuvant groups 1-2, 5 mice/subgroup were vaccinated by intraperitoneal injection, at an immunizing dose of 5 μg and 1 μg, respectively, and an injection volume of 1 mL. All the mice were subjected to the first vaccination at Week 0, and then subjected to the booster vaccination at Weeks 2 and 4, respectively. At Week 6, blood sample was collected via orbital bleeding, and the titers of antibodies against HPV66, HPV56 and HPV53 in serum were analyzed. The analysis results were shown in FIGS. 9A-9B. The results showed that H66N5-56T5-53S1, H66N5-56T5-53S2 and H66N5-56T5-53S4 VLP could induce the generation of high-titer neutralizing antibodies against HPV66 in mice, and their protective effects were slightly weaker than that of HPV66N5 VLP alone and that of the mixed HPV66/56/53 VLP at the same dose, but were significantly superior to that of HPV56N0 VLP alone or HPV53N5 VLP alone at the same dose; and they could induce the generation of high-titer neutralizing antibodies against HPV56 in mice, and their protective effects were comparable to that of HPV56N0 VLP alone and that of the mixed HPV66/56/53 VLP at the same dose, and were significantly superior to that of HPV66N5 VLP alone or HPV53N5 VLP alone at the same dose; and they could induce the generation of high-titer neutralizing antibodies against HPV53 in mice, and their protective effects were comparable to that of HPV53N5 VLP alone and the mixed HPV66/56/53 VLP at the same dose, and were significantly superior to that of HPV66N5 VLP alone or that of HPV56N0 VLP alone at the same dose. This showed that H66N5-56T5-53S1 VLP, H66N5-56T5-53S2 VLP and H66N5-56T5-53S4 VLP had good cross-immunogenicity and cross-protection against HPV66, HPV56 and HPV53.

Figure 10:
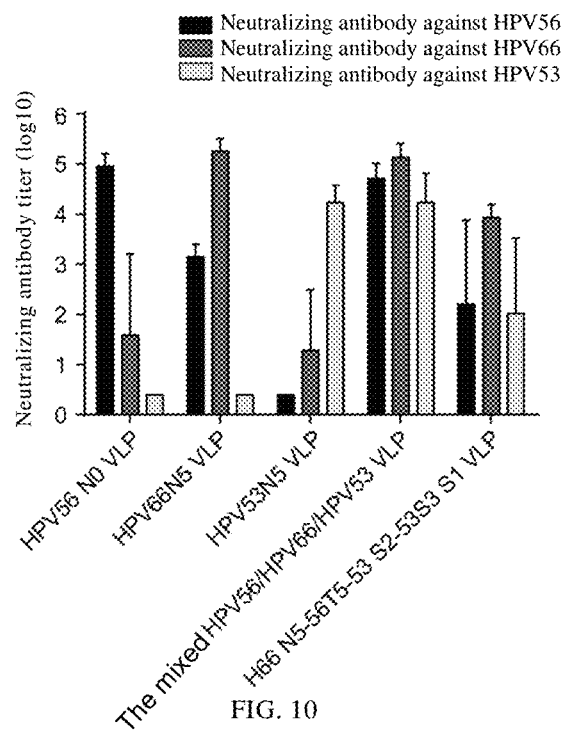

5 Mice/subgroup were vaccinated by intraperitoneal injection, at an immunizing dose of 5 μg, and an injection volume of 1 mL. All the mice were subjected to the first vaccination at Week 0, and then subjected to the booster vaccination at Weeks 2 and 4, respectively. At Week 6, blood sample was collected via orbital bleeding, and the titers of antibodies against HPV66, HPV56 and HPV53 in serum were analyzed. The analysis results were shown in FIG. 10. The results showed that H66N5-56T5-53S2-53S3 VLP could induce the generation of high-titer neutralizing antibodies against HPV66 in mice, and its protective effect was comparable to that of HPV66N5 VLP alone and that of the mixed HPV66/56/53 VLP at the same dose, and was significantly superior to that of HPV56N0 VLP alone or that of

TABLE 10

Vaccination schedule

| Group | Antigen for vaccination | Adjuvant | Immunizing dose | Number | Vaccination procedure (week) |
| --- | --- | --- | --- | --- | --- |
| Aluminum adjuvant group 1 | HPV66N5 VLP | aluminum adjuvant | 5 μg | 5 | 0, 2, 4 |
| | HPV56N0 VLP | aluminum adjuvant | 5 μg | 5 | 0, 2, 4 |
| | HPV53N5 VLP | aluminum adjuvant | 5 μg | 5 | 0, 2, 4 |
| | The mixed HPV66/56/53 VLP | aluminum adjuvant | 5 μg for each VLP | 5 | 0, 2, 4 |
| | H66N5-56T5-53S1 VLP | aluminum adjuvant | 5 μg | 5 | 0, 2, 4 |
| | H66N5-56T5-53S2 VLP | aluminum adjuvant | 5 μg | 5 | 0, 2, 4 |
| | H66N5-56T5-53S4 VLP | aluminum adjuvant | 5 μg | 5 | 0, 2, 4 |
| Aluminum adjuvant group 2 | HPV66N5 VLP | aluminum adjuvant | 1 μg | 5 | 0, 2, 4 |
| | HPV56N0 VLP | aluminum adjuvant | 1 μg | 5 | 0, 2, 4 |
| | HPV53N5 VLP | aluminum adjuvant | 1 μg | 5 | 0, 2, 4 |
| | The mixed HPV66/56/53 VLP | aluminum adjuvant | 1 μg for each VLP | 5 | 0, 2, 4 |
| | H66N5-56T5-53S1 VLP | aluminum adjuvant | 1 μg | 5 | 0, 2, 4 |
| | H66N5-56T5-53S2 VLP | aluminum adjuvant | 1 μg | 5 | 0, 2, 4 |
| | H66N5-56T5-53S4 VLP | aluminum adjuvant | 1 μg | 5 | 0, 2, 4 |

Example 6: Evaluation 3 of Neutralizing Antibody Titer in Serum of Mice Vaccinated with Virus-Like Particles In this experiment, the virus-like particle used was H66N5-56T5-53S2-53S3 VLP.

In this experiment, vaccination schedule was shown in Table 11. All the mice (6-week old BalB/c female mice) were divided into 2 groups: Experimental group (at an immunizing dose of 5 μg, using aluminum adjuvant), and Control group (at an immunizing dose of 5 μg, using aluminum adjuvant). Each Control group was further divided into 4 subgroups. The Control subgroups 1, 2 and 3 were vaccinated with HPV66N5 VLP alone, HPV56N0 VLP alone and HPV53N5 VLP alone, respectively; the Control subgroup 4 was vaccinated with the mixed HPV66/56/53 VLP (i.e. a mixture of HPV66N5 VLP, HPV56N0 VLP and HPV53N5 VLP, at a given immunizing dose for each VLP). The Experimental subgroup was vaccinated with H66N5-56T5-53S2-53S3 VLP.

HPV53N5 VLP alone at the same dose; and it could induce the generation of high-titer neutralizing antibodies against HPV56 in mice, and its protective effects was slightly weaker than that of HPV56N0 VLP alone, that of HPV66N5 VLP alone and that of the mixed HPV66/56/53 VLP at the same dose, but was significantly superior to that of HPV53N5 VLP alone at the same dose; and it could induce the generation of high-titer neutralizing antibodies against HPV53 in mice, and its protective effects was slightly weaker than that of HPV53N5 VLP alone and that of the mixed HPV66/56/53 VLP at the same dose, but was significantly superior to that of HPV66N5 VLP alone or that of HPV56N0 VLP alone at the same dose. This showed that H66N5-56T5-53S2-53S3 VLP had good cross-immunogenicity and cross-protection against HPV66, HPV56 and HPV53. H66N5-56T5-53S2-53S3 VLP could be used as effective vaccines for preventing HPV66 infection, HPV56 infection and HPV53 infection, and could be used in place of a mixed vaccine comprising HPV66 VLP, HPV56 VLP and HPV53 VLP.

TABLE 11

Vaccination schedule

| Group | Antigen for vaccination | Adjuvant | Immunizing dose | Number | Vaccination procedure (week) |
|---|---|---|---|---|---|
| Control group | HPV66N5 VLP | aluminum adjuvant | 5 gg | 5 | 0, 2, 4 |
| | HPV56N0 VLP | aluminum adjuvant | 5 Pg | 5 | 0, 2, 4 |
| | HPV53N5 VLP | aluminum adjuvant | 5 Pg | 5 | 0, 2, 4 |
| | The mixed HPV66/56/53 VLP | aluminum adjuvant | 5pg for each VLP | 5 | 0, 2, 4 |
| Experimental group | H66N5-56T5-53S2-53S3 VLP | aluminum adjuvant | 5 Pg | 5 | 0, 2, 4 |

Although the specific embodiments of the present invention have been described in details, those skilled in the art would understand that, according to the teachings disclosed in the specification, various modifications and changes can be made thereto, and that such modifications and changes are within the scope of the present invention. The scope of the present invention is given by the appended claims and any equivalents thereof.

The invention claimed is:

1. A mutated HPV66 L1 protein, wherein as compared with a wild type HPV66 L1 protein,
  (I) the mutated HPV66 L1 protein has the following mutations:
    (1) N-terminal truncation of any number of amino acids from 1 to 20; and
    (2) (a) substitution of amino acid residues at positions of the wild type HPV66 L1 protein which correspond to positions 265-283 of SEQ ID NO: 1 with amino acid residues at the corresponding positions of a L1 protein of a second type of wild-type HPV; or
    (b) substitution of amino acid residues at positions of the wild type HPV66 L1 protein which correspond to positions 347-357 of SEQ ID NO: 1 with amino acid residues at the corresponding positions of a L1 protein of a second type of wild-type HPV;
  or,
  (II) the mutated HPV66 L1 protein has the mutations as defined in (1) and (2) (b), and further has the following mutation:
    (3) substitution of amino acid residues at positions of the wild type HPV66 L1 protein which correspond to positions 51-60 of SEQ ID NO: 1 with amino acid residues at the corresponding positions of a L1 protein of a third type of wild-type HPV, or
    (4) substitution of amino acid residues at positions of the wild type HPV66 L1 protein which correspond to positions 114-150 of SEQ ID NO: 1 with amino acid residues at the corresponding positions of a L1 protein of a third type of wild-type HPV, or
    (5) substitution of amino acid residues at positions of the wild type HPV66 L1 protein which correspond to positions 259-283 of SEQ ID NO: 1 with amino acid residues at the corresponding positions of a L1 protein of a third type of wild-type HPV;
  or,
  (III) the mutated HPV66 L1 protein has the mutations as defined in (1), (2) (b) and (4), and further has the following mutation:
    (6) substitution of amino acid residues at positions of the wild type HPV66 L1 protein which correspond to positions 172-181 of SEQ ID NO: 1 with amino acid residues at the corresponding positions of a L1 protein of a third type of wild-type HPV,
  wherein said corresponding positions are determined by optimal alignment of the sequences being compared, and wherein the L1 protein of the second type of wild type HPV comprises different amino acid sequence at region corresponding to positions 265-283 or 347-357 of SEQ ID NO.1, the L1 protein of the third type of wild type HPV comprises different amino acid sequences at regions corresponding to positions 51-60, 114-150, 259-283 or 172-181 of SEQ ID NO.1.

2. An isolated nucleic acid, encoding the mutated HPV66 L1 protein according to claim 1.

3. A vector comprising the isolated nucleic acid according to claim 2.

4. An isolated host cell comprising the isolated nucleic acid according to claim 2 and/or a vector comprising the isolated nucleic acid according to claim 2.

5. An HPV virus-like particle, comprising or consisting of the mutated HPV66 L1 protein according to claim 1.

6. A composition, comprising:
  (i) the mutated HPV66 L1 protein according to claim 1, or
  (ii) an isolated nucleic acid encoding the mutated HPV66 L1 protein as described in (i), or
  (iii) a vector comprising the isolated nucleic acid as described in (ii), or
  (iv) an isolated host cell comprising the isolated nucleic acid as described in (ii) and/or the vector comprising the isolated nucleic acid as described in (iii), or
  (v) an HPV virus-like particle comprising or consisting of the mutated HPV66 L1 protein as described in (i).

7. A pharmaceutical composition or vaccine, comprising the HPV virus-like particle according to claim 5, and optionally a pharmaceutically acceptable carrier and/or excipient.

8. A method for preparing the mutated HPV66 L1 protein according to claim 1, comprising expressing the mutated HPV66 L1 protein in a host cell, and then recovering the mutated HPV66 L1 protein from a culture of the host cell.

9. A method for preparing a vaccine, comprising combining the HPV virus-like particle according to claim 5 with a pharmaceutically acceptable carrier and/or excipient.

10. A method for preventing HPV infection or a disease caused by HPV infection, comprising administering to a subject a prophylactically effective amount of the HPV virus-like particle according to claim 5 or the pharmaceutical composition or vaccine comprising the HPV virus-like particle according to claim 5 and optionally a pharmaceutically acceptable carrier and/or excipient.

11. The mutated HPV66 L1 protein according to claim 1, wherein the mutated HPV66 L1 protein is characterized by one or more of the following items:
  (i) the mutated HPV66 L1 protein has 3, 5, 8, 10, 12, 15 or 18 amino acids truncated at N-terminal, as compared with the wild type HPV66 L1 protein;
  (ii) the second type of wild-type HPV is HPV56;
  (iii) the amino acid residues at the corresponding positions as described in (2) (a) are amino acid residues at positions 265-283 of a wild type HPV56 L1 protein;
  (iv) the amino acid residues at the corresponding positions as described in (2) (b) are amino acid residues at positions 347-357 of a wild type HPV56 L1 protein;
  (v) the third type of wild-type HPV is HPV53;
  (vi) the amino acid residues at the corresponding positions as described in (3) are amino acid residues at positions 51-59 of a wild type HPV53 L1 protein;
  (vii) the amino acid residues at the corresponding positions as described in (4) are amino acid residues at positions 113-149 of a wild type HPV53 L1 protein;
  (viii) the amino acid residues at the corresponding positions as described in (5) are amino acid residues at positions 258-282 of a wild type HPV53 L1 protein;

(ix) the amino acid residues at the corresponding positions as described in (6) are amino acid residues at positions 171-180 of a wild type HPV53 L1 protein;
(x) the wild type HPV66 L1 protein has an amino acid sequence as set forth in SEQ ID NO: 1;
(xi) the wild type HPV56 L1 protein has an amino acid sequence as set forth in SEQ ID NO: 2;
(xii) the wild type HPV53 L1 protein has an amino acid sequence as set forth in SEQ ID NO: 3.

12. The mutated HPV66 L1 protein according to claim 1, wherein the mutated HPV66 L1 protein has an amino acid sequence selected from the group consisting of: SEQ ID NO: 7, 8, 9, 10, 11 and 63.

13. The isolated nucleic acid according to claim 2, wherein the isolated nucleic acid according to the invention has a nucleotide sequence selected from the group consisting of: SEQ ID NO: 18, 19, 20, 21, 22 and 64.

14. The pharmaceutical composition or vaccine according to claim 7, wherein the HPV virus-like particle is present in an amount effective for preventing HPV infection or a disease caused by HPV infection.

15. The pharmaceutical composition or vaccine according to claim 14, wherein the HPV infection is infection by one or more HPV types, and/or, the disease caused by HPV infection is selected from the group consisting of cervical cancer and condyloma acuminatum.

16. The pharmaceutical composition or vaccine according to claim 15, wherein the HPV infection is selected from: HPV66 infection, HPV56 infection, HPV53 infection and any combination thereof.

17. The method according to claim 8, wherein the host cell is *E. coli*.

18. The method according to claim 17, wherein the method comprises the steps of: expressing the mutated HPV66 L1 protein in *E. coli*, and then obtaining the mutated HPV66 L1 protein by purifying a lysate supernatant of the *E. coli*.

19. The method according to claim 10, wherein the HPV infection is infection by one or more HPV types, and/or, the disease caused by HPV infection is selected from the group consisting of cervical cancer and condyloma acuminatum.

20. The method according to claim 19, wherein the HPV infection is selected from: HPV66 infection, HPV56 infection, HPV53 infection and any combination thereof.

* * * * *